United States Patent [19]

Wakabayashi et al.

[11] Patent Number: 4,673,684

[45] Date of Patent: Jun. 16, 1987

[54] AMIDE DERIVATIVES AND 5-LIPOXYGENASE INHIBITORS CONTAINING THE SAME AS AN ACTIVE INGREDIENT

[75] Inventors: Toshio Wakabayashi; Makoto Takai; Shuji Ichikawa; Jun-ichiro Arai; Seiitsu Murota, all of Tokyo, Japan

[73] Assignee: Terumo Corporation, Tokyo, Japan

[21] Appl. No.: 719,131

[22] Filed: Apr. 2, 1985

[30] Foreign Application Priority Data

| Apr. 4, 1984 | [JP] | Japan | 59-67286 |
| Jul. 6, 1984 | [JP] | Japan | 59-141175 |
| Jul. 6, 1984 | [JP] | Japan | 59-141176 |
| Sep. 25, 1984 | [JP] | Japan | 59-200297 |
| Oct. 31, 1984 | [JP] | Japan | 59-229105 |
| Nov. 20, 1984 | [JP] | Japan | 59-245695 |

[51] Int. Cl.$^4$ .................. A61K 31/445; C07D 211/46; C07D 405/12
[52] U.S. Cl. .................................... 514/327; 514/321; 514/826; 546/197; 546/221
[58] Field of Search ............... 546/221, 197; 514/327, 514/321

[56] References Cited

U.S. PATENT DOCUMENTS

| 2,745,837 | 5/1956 | Papa et al. | 546/216 |
| 2,751,388 | 6/1956 | Levy | 546/216 |
| 4,261,990 | 4/1981 | Bowman | 546/242 |
| 4,550,116 | 10/1985 | Soto et al. | 546/216 |

*Primary Examiner*—Norma S. Milestone
*Attorney, Agent, or Firm*—Cushman, Darby & Cushman

[57] ABSTRACT

According to the invention, there are provided novel amide derivatives and 5-lipoxygenase inhibitors containing the same as an effective ingredient.

The above-mentioned compounds of the invention have been demonstrated to posses 5-lipoxygenase-inhibiting activities. These compounds can inhibit the production of leucotrienes such as $LTC_4$ and $LTD_4$ which are allergy-inducing factors by inhibiting the activity of 5-lipoxygenase. Accordingly, the amide derivatives can be used as 5-lipoxygenase inhibitors effective for allergic asthma, allergic rhinitis and the like.

9 Claims, No Drawings

AMIDE DERIVATIVES AND 5-LIPOXYGENASE INHIBITORS CONTAINING THE SAME AS AN ACTIVE INGREDIENT

BACKGROUND OF THE INVENTION

1. Field of the Invention

The present invention relates to novel amide derivatives and 5-lipoxygenase inhibitors containing the same as an active ingredient. The amide derivatives provided by the invention possess activities inhibiting 5-lipoxygenase which is an enzyme. Leucotrienes such as leucotriene $C_4(LTC_4)$ and leucotriene $D_4(LTD_4)$ which are allergy-inducing factors are biosynthesized in vivo from arachidonic acid by the action of 5-lipoxygenase. Therefore, the amide derivatives of the invention, which possess 5-lipoxygenase-inhibiting activities, will inhibit biosynthesis of the above-mentioned allergy-inhibiting factors thereby being useful as antiallergic agents which can effectively be used for allergic asthma, allergic rhinitis, etc.

2. Description of the Prior Art

It has recently been found that action of 5-lipoxygenase on arachidonic acid results in formation of leucotrienes which are allergy-inducing factors (Science vol. 220, page 568, 1983, published by the American Association for the Advancement of Science).

As described above, leucotrienes such as $LTC_4$ and $LTD_4$ which are 5-lipoxygenase products from arachidonic acid are important factors participating in onset of diseases such as allergic asthma and allergic rhinitis, and therefore, development of drugs that are of 5-lipoxygenase-inactivating activities and capable of inhibiting its action is strongly desired.

SUMMARY OF THE INVENTION

As a results of studies on the synthesis of amide derivatives and their 5-lipoxygenase-inhibiting activities, we have found that the amide derivatives according to the present invention possess high 5-lipoxygenase-inhibiting activities. The invention has been completed based upon such finding.

It is an object of the invention to provide novel amide derivatives and 5-lipoxygenase inhibitors containing the same as an active ingredient.

DETAILED DESCRIPTION OF THE INVENTION

According to the present invention, there are provided amide derivatives having the general formula:

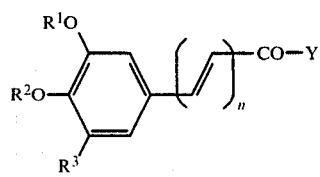
(I)

In the formula (I), $R^1$ represents hydrogen atom or a lower alkyl group, $R^2$ represents hydrogen atom, a lower alkyl group or toluoyloxy group, or $R^1$ and $R^2$ when taken together represents a lower alkylene group, $R^3$ represents hydrogen atom or a lower alkoxy group, $R^2$ and $R^3$ both being hydrogen atom when $R^1$ represents hydrogen atom, and n is an integer of 1 or 2; Y represents an amino group having any of the formulae (1)–(10) below:

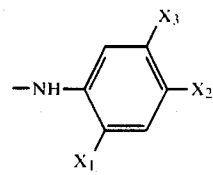
(1)

wherein $X^1$ represents hydrogen atom or carboxyl group, $X^2$ represents hydrogen atom or hydroxyl group and $X^3$ represents hydrogen atom or a halogen atom,

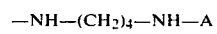
(2)

wherein A represents a lower aliphatic acyl group, benzoyl group which may be substituted with amino group, an acyl group derived from a higher unsaturated fatty acid or a group having the formula

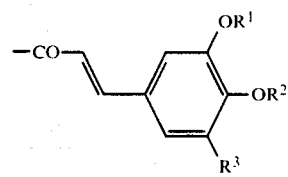

wherein $R^1$, $R^2$ and $R^3$ are as defined above,

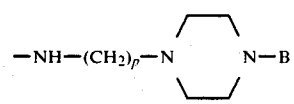
(3)

wherein B represents a lower alkyl group, benzoyl group which may be substituted with amino or diphenylmethyl group phenyl moiety of which may be substituted with a halogen atom or a lower alkoxyl group and p is an integer from 2 to 4,

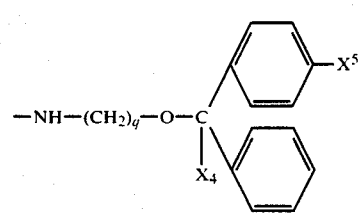
(4)

wherein $X^4$ represents hydrogen atom or a lower alkoxyl group, $X^5$ represents hydrogen atom, a halogen atom or a lower alkoxyl group and g is an integer of 2 or 3,

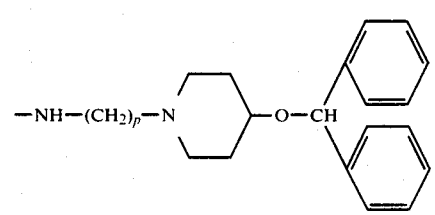
(5)

wherein p is as defined above,

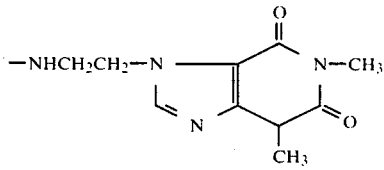

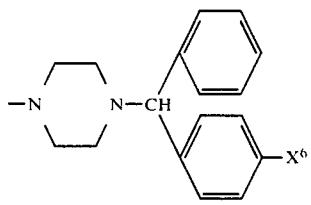

wherein $X^6$ represents hydrogen atom, a halogen atom or a lower alkoxyl group,

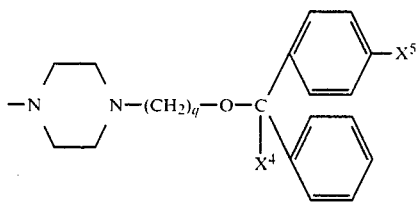

wherein $X^4$, $X^5$ and q are as defined above,

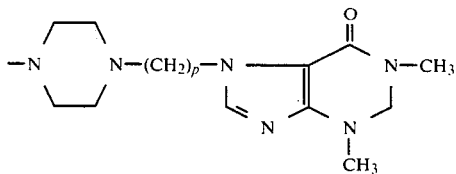

wherein p is as defined above, and

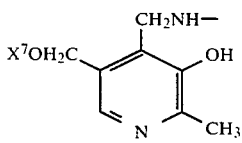

wherein $X^7$ represents hydrogen atom, an aliphatic acyl group, toluoyl group or 5-(3,4-dihydroxyphenyl)pentadienoyl group.

Further according to the invention, 5-lipoxygenase inhibitors containing as an active ingredient an amide derivative having the above-described general formula (I) are provided.

In the definitions of the above formula, the lower alkyl group means an alkyl group containing 1-4 carbon atoms such as methyl, ethyl, n-propyl, isopropyl, n-butyl or isobutyl. The lower alkyl group means an alkoxyl group containing 1-4 carbon atoms such as methoxy, ethoxy, n-propoxy, isopropoxy, n-butoxy or isobutoxy. The lower alkylene group means an alkylene group containing 1-3 carbon atoms such as methylene, ethylene, trimethylene or 1-methylethylene. The halogen atom preferably means chlorine, bromine or iodine. The lower aliphatic acyl group means an aliphatic acyl group containing 2-4 carbon atoms, and acetyl group is particularly preferable. The acyl group derived from a higher unsaturated fatty acid means a carboxylic acid residue containing 16-20 carbon atoms and having 2-6 double bonds. As preferred examples are mentioned carboxylic acid residue of 5,8,11,14,17-eicosapentaenic acid, 4,7,10,13,16,19-docosahexaenic acid, 9,19-octadecadienic acid (linolic acid), 6,9,12-octadecatrienic acid (γ-linolenic acid) and 9,12,15-octadecatrienic acid (α-linolenic acid).

The amide derivatives having the above formula (I) are novel compounds which are produced, for example, by reacting a carboxylic acid having the formula

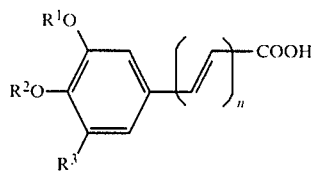

wherein $R^1$, $R^2$, $R^3$ and n are as defined above or a reactive derivative thereof such as a compound having the formula

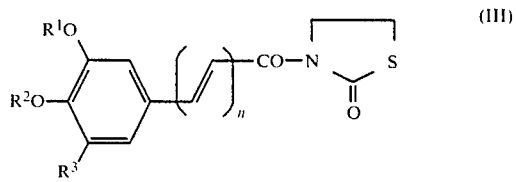

wherein $R^1$, $R^2$, $R^3$ and n are as defined above with an amine having the formula $$H-Y \qquad (IV)$$

wherein Y is as defined above and, if required, subjecting the reaction product to a deprotection reaction.

The amide derivatives of the invention are useful as 5-lipoxygenase inhibitors or antiallergic agents. The dosage will generally be in the range from 30 to 200 mg and preferably from 50 to 600 mg per day in adults, although it is variable depending upon of the patient. It may be divided into one to three doses per day as required depending upon conditions of the patient. The administration may be by any suitable route. Intravenous injection is applicable, though oral administration is particularly desirable.

The compounds of the invention may be blended with pharmaceutical carriers or excipients and formulated into a variety of forms such as tablets, sugar-coated tablets, powders, capsules, granules, suspension, emulsion or injectable solution. As examples of the carrier or excipient are mentioned calcium carbonate, starch, glucose, lactose, dextrin, arginic acid, mannitol, talc, magnesium stearate and the like.

Examples and Test Example will be given below to describe the invention in more details. It is to be understood that the invention will be limited in no way by these examples.

EXAMPLE 1

To a solution of 2.12 g (7.41 mmol) of N-(p-chlorobenzhydryl)piperazine in triethylamine (11 ml) was added in an argon atmosphere 868 mg (7.48 mmol)

of 2-chloroethylamine hydrochloride. The mixture was refluxed for 8 hours.

Separately, to a solution of 402 mg (1.42 mmol) of 3-(3-methoxy-4-β-methoxyethoxymethoxyphenyl)-2-propenic acid in dry 1,2-dichloroethane (20 ml) were added in an argon atmosphere 19 mg (0.156 mmol) of dimethylaminopyridine and 487 mg (2.36 mmol) of N,N'-dicyclohexylcarbodiimide. The mixture was reacted at room temperature for 15 min. To the reaction mixture was added 3.2 ml of the triethylamine solution of N-(p-chlorobenzhydryl)-N'-(2-aminoethyl)piperazine prepared above. The mixture was reacted at room temperature for 21 hours, followed by filtration of precipitates thus formed. To the filtrate was then added water, and the mixture was extracted with chloroform. The organic layer was concentrated under reduced pressure, and the residue obtained was subjected to silica gel column chromatography. There was obtained from a fraction eluted with chloroform 65 mg (0.109 mmol) of N-(p-chlorobenzhydryl)-N'[2-{3-(3-methoxy-4-β-methoxyethoxymethoxyphenyl)-2-propenoyl}-aminoethyl]piperazine.

To a solution of 65 mg (0.109 mmol) of the amide compound obtained above in methanol (5 ml) was added 32 mg (0.168 mmol) of p-toluenesulfonic acid monohydrate. The mixture was refluxed in an argon atmosphere for 2.5 hours. To the reaction mixture was added water, followed by addition of an aqueous solution of sodium carbonate to adjust the pH to 10. The mixture was then extracted with ethyl acetate. The organic layer was concentrated under reduced pressure, and the residue obtained was subjected to silica gel thin layer chromatography. Development with chloroform-methanol (20:1) yielded 40 mg (0.0787 mmol) of N-(p-chlorobenzhydryl)-N'-[2-{3-(3-methoxy-4-hydroxyphenyl)-2-propenoyl}-aminoethyl]piperazine. Spectrophotometric data of the product support the structure shown below.

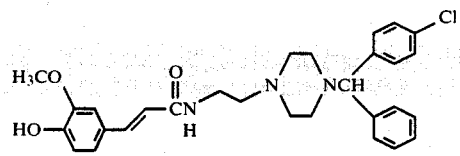

IR $\nu_{max}$ $^{CHCl_3}$ (cm$^{-1}$): 3550, 3400, 1670, 1625, 1605.

$^1$H-NMR (deutero acetone) δ: 2.43(10H, bs), 3.38(2H, q, J=6Hz), 3.85 (3H, s), 4.27 (1H, s), 6.05 (1H, d, J=14Hz).

EXAMPLE 2

To a solution of 504 mg (2 mmol) of benzhydrylpiperazine in triethylamine (3 ml) was added in an argon atmosphere 232 mg of 2-chloroethylamine hydrochloride. The mixture was refluxed for 8 hours. To the resulting solution wa added a solution of 738 mg (2 mmol) of N-3-(3-methoxy-4-β-methoxyethoxymethoxyphenyl)-2-propenoyl-thiazolidine-2-thione in tetrahydrofuran (5 ml). The mixture was reacted at room temperature for 1 hour. To the reaction mixture was added 2N aqueous solution of sodium hydroxide, and the mixture was extracted with chloroform. The organic layer was concentrated under reduced pressure, and the residue obtained was subjected to silica gel column chromatography. There was obtained from a fraction eluted with chloroform - methanol (50:1) 290 mg (0.51 mmol) of N-benzhydryl-N'-[2-{3-(3-methoxy-4-β-methoxyethoxymethoxyphenyl)-2-propenoyl}aminoethyl]piperazine.

Then, to a solution of 227 mg (0.4 mmol) of the amide product prepared above was added in an argon atmosphere 76 mg (0.44 mmol) of p-toluene sulfonic acid, and the mixture was heated under reflux for 1 hour. To the reaction mixture, after cooled, was added saturated solution of sodium hydrogen carbonate, and the mixture was extracted with ethyl acetate. The organic layer was concentrated under reduced pressure, and the residue was subjected to Sephadex LH-20 column chromatography. There was obtained from a fraction eluted with methanol 169 mg (0.37 mmol) of N-benzhydryl-N'-[2-{3-(3-methoxy-4-β-hydroxyphenyl)-2-propenoyl}aminoethyl]piperazine.

Spectrophotomeric data of the product support the structure shown below.

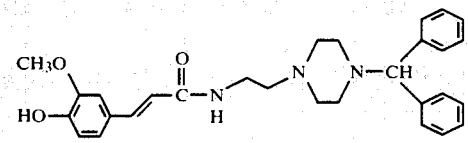

IR $\nu_{max}$ $^{CHCl_3}$ (cm$^{-1}$): 3550, 3400, 1660

EXAMPLE 3

To a solution of 880 mg (10 mmol) of 1,4-diaminobutane in tetrahydrofuran (20 ml) was added in an argon atmosphere a solution of 370 mg (1 mmol) of N-3-(3-methoxy-4-β-methoxyethoxymethoxyphenyl)-2-propenoylthiazoline-2-thione in tetrahydrofuran (10 ml) at room temperature over 30 min., followed by addition of 2N-aqueous solution of sodium hydroxide. The mixture was extracted with chloroform.

The organic layer was washed with water and dried over anhydrous magnesium sulfate. Then, the solvent was removed by concentration under reduced pressure. To a solution of the residue thus obtained in tetrahydrofuran (10 ml) was added in an argon atmosphere at room temperature a solution of 390 mg (1.05 mmol) of α-linolenic acid thiazolidinethionamide in tetrahydrofuran (4 ml). The mixture was reacted at room temperature for 90 min.

To the reaction mixture was added 20 ml of 2N-aqueous solution of sodium hydroxide, and the mixture was extracted with dichloromethane. The organic layer was concentrated under reduced pressure, and the residue thus obtained was subjected to silica gel column chromatography. There was obtained from a fraction eluted with chloroform - methanol (99:1) 378 mg (0.61 mmol) of N-[3-(3-methoxy-4-β-methoxyethoxymethoxyphenyl)-2-propenoyl]-N'-[9,12,15-octadecatrienoyl]-1,4-diaminobutane.

A solution of 310 mg (0.5 mmol) of the compound prepared above in a mixed solvent of 1,4-dioxane - acetic acid - water (5:4:1) (5 ml) was reacted by heating under reflux for 8 hours in an argon atmosphere. The solvent was removed by concentration under reduced pressure, and the residue thus obtained was subjected to Sephadex LH-20 column chromatography. There was obtained from a fraction eluted with methanol: 186 mg (0.35 mmol) of N-[3-(3-methoxy-4-hydroxyphenyl)-2-propenoyl]-N'-[9,12,15-octadecatrienoyl]-1,4-diaminobutan. Spectrophotometric data of the product support the structure shown below.

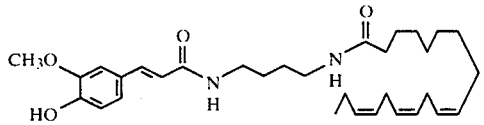

IR $\nu_{max}^{KBr}$ (cm$^{-1}$): 3400, 1645, 1600

EXAMPLE 4

To a solution of 44 mg (0.5 mmol) of 1,4-diaminobutane in tetrahydrofuran (10 ml) was added in an argon atmosphere at room temperature a solution of 370 mg (1 mmol) of N-3-(3-methoxy-4-β-methoxyethoxymethoxyphenyl)-2-propenoyl-thiazoline-2-thione in tetrahydrofuran (5 ml). The mixture was reacted at room temperature for 2 hours. To the reaction mixture was added 20 ml of 1N-aqueous solution of sodium hydroxide, and the mixture was extracted with dichloromethane. The organic layer was concentrated under reduced pressure, and the residue thus obtained was subjected to silica gel column chromatography. There was obtained from a fraction eluted with chloroform-methanol (97:3) 297 mg (0.48 mmol) of N,N'-bis-{3-(3-methoxy-4-β-methoxyethoxymethoxyphenyl)-2-propenoyl}-1,4-diaminobutane.

A solution of 268 mg (0.45 mmol) of the compound prepared above in a mixed solvent of 1,4-dioxane-acetic acid-water (5:4:1) (5 ml) was reacted by heating under reflux for 8 hours in an argon atmosphere. The solvent was removed by concentration under reduced pressure, and the residue thus obtained was subjected to Sephadex LH-20 column chromatography. There was obtained from a fraction eluted with methanol 164 mg (0.37 mmol) of N,N'-bis-{3-(3-methoxy-4-hydroxyphenyl)-2-propenoyl}-1,4-diaminobutane.

Spectrophotometric data of the product support the structure shown below.

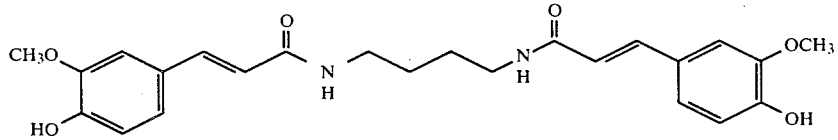

IR $\nu_{max}^{KBr}$ (cm$^{-1}$): 1650

EXAMPLE 5

To a solution of 146 mg (0.442 mmol) of N-caffeoyl-pyridoxsamine in pyridine (1 ml) was added in an argon atmosphere 0.5 ml (5.29 mmol) of acetic anhydride. The mixture was reacted at room temperature for 18 hours. The reaction mixture was concentrated under reduced pressure, and the residue thus obtained was subjected to silica gel column chromatography. There was obtained from a fraction eluted with chloroform - methanol (10:1)184 mg (0.369 mmol) of tetracetylated N-caffeoyl-pyridoxamine.

To a solution of 184 mg (0.369 mmol) of the amide compound prepared above in tetrahydrofuran (8 ml) and water (2 ml) at 0° C. was added piperidine (1.52 ml). The mixture was reacted for 25 hours, and water was added to the reaction mixture. The mixture was extracted with ethyl acetate, and the organic layer was concentrated under reduced pressure. The residue thus obtained was subjected to silica gel column chromatography. There was obtained from a fraction eluted with chloroform -methanol (10:1) 48 mg (0.129 mmol) of N-caffeoyl-o-acetylpyridoxane. Spectrophotometric data of the product support the structure shown below.

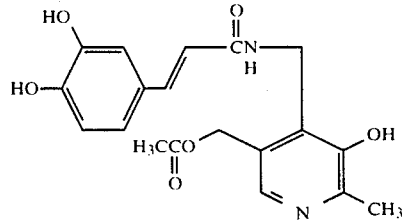

IR $\nu_{max}^{KBr}$ (cm$^{-1}$): 3400, 1745, 1655, 1600

$^1$H-NMR (deutero pyridine) δ: 1.97 (3H, s), 2.72 (3H, s), 4.78 (2H, d, J=6Hz), 5.35 (2H, s), 6.70 (1H, d, J=15Hz), 7.12 (2H, s), 7.45 (1H, s), 8.02 (1H, d, J=15Hz), 8.33 (1H, s), 9.80 (1H, t, J=6Hz)

EXAMPLE 6

To a solution of 430 mg (4.877 mmol) of 1,4-diaminobutane in tetrahydrofuran (12 ml) at room temperature was added in an argon atmosphere 250 mg (0.546 mmol) of N-3-[3,4-di(β-methoxyethoxymethoxy)phenyl]-propenoyl-thiazolidine-2-thione in tetrahydrofuran (2 ml). The mixture was reacted at room temperature for 20 min. To the reaction mixture was added 15 ml of 0.7N-aqueous solution of sodium hydroxide, and the mixture was extracted four times with chloroform. Organic layer of the extract was washed with water and dried over anhydrous sodium sulfate. Then, the solvent was removed by distillation under reduced pressure to give 234 mg of an extraction residue. To a solution of the residue in tetrahydrofuran (6 ml) at room temperature was added in an argon atmosphere a solution of 235 mg (0.547 mmol) of 4,7,10,13,16,19-docosahexaenoic acid thiozolidinethionamide in tetrahydrofuran (2 ml). The mixture was reacted at room temperature for 40 min., followed by addition of 10 ml of 0.7N-aqueous solution of sodium hydroxide. The mixture was extracted three times with dichloromethane. Organic layer of the extract was washed with water and dried over anhydrous sodium sulfate. Then, the solvent was removed by distillation under reduced pressure to give 480 mg of residue from the extraction. The residue was subjected to silica gel column chromatography. There was obtained from a fraction eluted with chloroform - methanol (97:3) 352 mg (0.478 mmol) of N-3-[3,4-di(β-methoxyethoxymethoxy)-phenyl[propenoyl-N'-4,7,10,13,16,19-docosahexaenoyl-1,4-diaminobutane.

A solution of 235 mg (0.319 mmol) of the compound prepared above in a mixed solvent of 8 ml of acetic acid, 2 ml of water and 4 ml of 1,4-dioxane was heated under reflux for 11 hour 30 min. Removal of the solvent from the reaction mixture by distillation under reduced pressure yielded 195 mg of a residue. The residue was subjected to Sephadex (LH 20) column chromatography.

There was obtained from a fraction eluted with methanol 77 mg (0.137 mmol) of N-[3-(3,4-dihydroxyphenyl)-2-propenoyl]-N'-[4,7,10,13,16,19-docosahexaenoyl]1,4-diaminobutane. Splectrophotometric data of the product support the structure shown below.

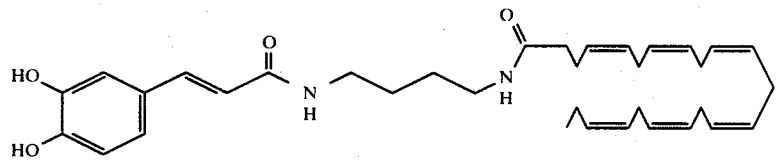

IR $\nu_{max}{}^{CHCl_3}$ (cm$^{-1}$): 3520, 3430, 3255, 1665, 1600, 1520, 1430

$^1$H-NMR (mixed solvent of deutero chloroform-deutero-pyridine 4:1) δ: 0.92 (3H, t, J=7.5Hz), 1.40–1.63 (4H), 2.70 -2.93 (10H), 3.10–3.47 (4H), 5.23–5.47 (12H), 6.32 (1H, d, J=5.5Hz), 6.89 (2H, bs), 7.10 (1H, bs), 7.59 1H, d, J=5.5Hz)

EXAMPLE 7

To a solution of 26 mg (0.295 mmol) of 1,4-diaminobutane in tetrahydrofuran (6 ml) at room temperature was added in an argon atmosphere a solution of 300 mg (0.66 mmol) of N-3-[3,4-di(β-methoxyethoxymethoxy)-phenyl]-propenoyl-thiazolidine-2-thione in tetrahydrofuran (2 ml). The mixture was reacted at room temperature for 2 hours. To the reaction mixture was added 20 ml of 1N-aqueous solution of sodium hydroxide, and the mixture was extracted three times with dichloromethane. Organic layer of the extract was washed with water and dried over anhydrous sodium sulfate. Then, the solvent was removed by distillation under reduced pressure to give 295 mg of an extraction residue. The residue was subjected to silica gel column chromatography. There was obtained from a fraction eluted with chloroform-methanol (97:3) 218 mg of N,N'-bis[3,4-di(β-methoxyethoxymethoxy)-phenyl]-2-propenoyl]-1,4-diaminobutane.

To a solution of 216 mg (0.282 mmol) of the product prepared above in methanol (20 ml) at room temperature was added in an argon atmosphere 5 mg (0.028 mmol) of p-toluenesulfonic acid. The mixture was reacted by heating under reflux for 5 hour 30 min. The reaction mixture was concentrated under reduced pressure, and precipitates thus formed were separated by filtration to give 68 mg of a crude product. The product was recrystallized from methanol-acetone (6:1) to give 46 mg (0.112 mmol) of N,N'-bis-[(3,4-dihydroxyphenyl)-2-propenoyl]-1,4-diaminobutane. Spectrophotometric data of the product support the structure shown below.

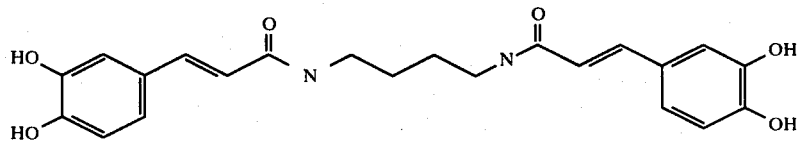

IR $_{max}{}^{KBr}$ (cm$^{-1}$): 1655.

$^1$H-NMR (deuterodimethylsulfoxide) δ:1.33–1.63 (4H), 3.03–3.33 (4H), 6.42 (2H, d, J=15.5Hz), 6.87 (4H, bs), 7.06 (2H, bs), 7.36 (2H, d, J=155Hz)

EXAMPLE 8

To a solution of 198 mg (0.79 mmol) of benzhydrylpiperazine in 5 ml of tetrahydrofuran was added in an argon atmosphere a solution of 205 mg (0.45 mmol) of N-3-{3,4-di(β-methoxyethoxymethoxy)phenyl}-2-propenoyl-thiazolidine-2-thione in 5 ml of tetrahydrofuran. The mixture was reacted at room temperature for 10 min. To the reaction mixture was added 20 ml of 2N-aqueous solution of sodium hydroxide, and the mixture was extracted with ethyl acetate. The organic layer was concentrated under reduced pressure, and the residue thus obtained was subjected to silica gel column chromatography. There was obtained from a fraction eluted with chloroform - methanol (100:1) 241 mg (0.41 mmol) of N-benzhydryl-N'-[3-{3,4-di(β-methoxyethoxymethoxy)-phenyl}-2-propenoyl]piperazine.

To a solution of 170 mg (0.29 mmol) of the amide compound prepared above in 5 ml of methanol was added in an argon atmosphere 52 mg (0.30 mmol) of p-toluenesulfonic acid. The mixture was heated under reflux for 3 hours. To the reaction mixture was added 20 ml of saturated aqueous solution of sodium hydrogen carbonate, and athe mixture was extracted with ethyl acetate. The organic layer was concentrated under reduced pressure, and the residue thus obtained was recrystallized from methanol to give 95 mg (0.23 mmol) of N-benzhydryl-N'-{(3,4-dihydroxyphenyl)-2-propenoyl}-piperazine. Spectrophotometric data of the product support the structure shown below.

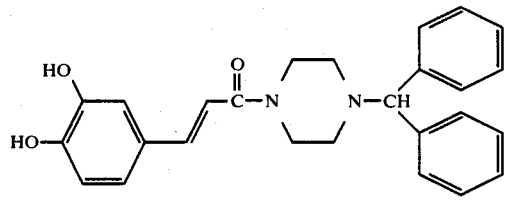

IR $\nu_{max}{}^{KBr}$ (cm$^{-1}$) 3475, 3125, 1645, 1600, 1570, 1530.

$^1$H-NMR (deutero pyridine) δ: 2.33 (4H, m), 3.70 (4H, m), 4.28 (1H, s), 6.90–7.57 (14H, m), 8.02 (1H, d, J=16Hz)

EXAMPLE 9

A mixture of 271 mg (1.07 mmol) of benzhydrylpiperazine, 4 ml (28.7 mmol) of triethylamine and 193 mg (1.66 mmol) of 2-chlorethylamine hydrochloride was heated in an argon atmosphere at 95° C. for 9 hours.

The reaction solution was concentrated under reduced pressure. To a solution of the residue thus obtained, which had been cooled to 0° C., was added a solution of 0.8 mg (5.6 mmol) of trifluoroacetic anhydride in methylene chloride (2 ml). The mixture was reacted at 0° C. for 4 hours. Water was added to the reaction solution, and the mixture was extracted with chloroform. The organic layer was concentrated under reduced pressure and the residue thus obtained was subjected to silica gel column chromatography. There was obtained from a fraction eluted with chloroform 99 mg (0.26 mmol) of N-benzhydryl-N'-(2-trifluoroacetylaminoethyl)-piperidine.

To a solution of 99 mg of the piperidine derivative prepared above in 5 ml of methanol was added in an argon atmosphere was added 1 ml of 3N-aqueous solution of potassium carbonate. The mixture was heated under reflux for 30 min. Water was added to the reaction solution, and the mixture was extracted with n-butanol. The organic layer was concentrated under reduced pressure, followed by dissolution in 5 ml of tetrahydrofuran. To the solution was added a solution of 120 mg (0.26 mmol) of N-3-{3,4-di($\beta$-methoxyethoxymethoxy)phenyl}-2-propenoyl-thiazolidine-2-thione in tetrahydrofuran (5 ml in an argon atmosphere. The mixture was reacted at room temperature for 30 min., followed by addition of 2N-aqueous solution of sodium hydroxide. The mixture was extracted with chloroform, and the organic layer was concentrated under reduced pressure. The residue thus obtained was subjected to silica gel column chromatography. There was obtained from a fraction eluted with chloroform - methanol (50:1) 140 mg (0.13 mmol) of N-benzhydryl-N'-[2-[3-{3,4-di($\beta$-methoxyethoxymethoxy)-phenyl}-2-propenoyl]aminoethyl]piperazine.

To a solution of 80 mg (0.13 mmol) of the amide product prepared above in 2 ml of methanol was added in an argon atmosphere 47 mg (0.27 mmol) of p-toluenesulfonic acid. The mixture was heated under reflux for 3 hours. To the reaction solution after cooled was added saturated solution of sodium hydrogen carbonate. The mixture was extracted with ethyl acetate, and the organic layer was concentrated under reduced pressure. The residue thus obtained was subjected to Sephadex LH-20 column chromatography. There was obtained from a fraction eluted with methanol 36 mg (0.078 mmol) of N-benzhydryl-N'-[2-{3-(3,4-dihydroxyphenyl)-2-propenoyl}-aminoethyl]piperazine.

Spectrophotometric data of the product support the structure shown below.

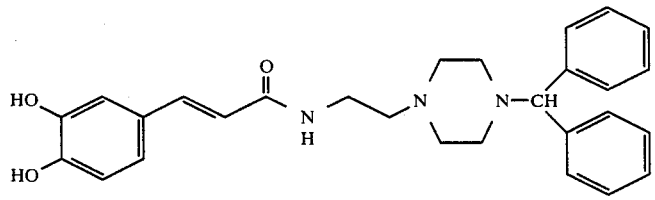

IR $\nu_{max}^{KBr}$ (cm$^{-1}$) 3400, 1660, 1595, 1510.
$^1$H-NMR (deutero pyridine) δ:2.40 (10H, bs), 3.63 (2H, m), 4.22 (1H, s), 6.68 (1H, d, J=16Hz), 6.90–7.53 (13H, m), 7.92 (1H, d, J=16Hz)

EXAMPLE 10

To a solution of 720 mg (2.02 mmol) of 3-{3,4-di-($\beta$-methoxyethoxymethoxy)phenyl}-2-propionic acid in 20 ml of dry acetonitrile were added in an argon atmosphere 287 mg (2.0 mmol) of 5-chloro-2-hydroxyaniline, 511 mg (2.0 mmol) of 2-chloro-1-methylpyridinium iodide and 0.6 ml (4.3 mmol) of triethylamine. The mixture was reacted overnight at room temperature. Water was added to the reaction solution, and the mixture was extracted with chloroform. The organic layer was concentrated under reduced pressure, and the residue thus obtained was subjected to silica gel column chromatography. There was obtained from a fraction eluted with benzene - ethyl acetate (5:2) 150 mg (0.31 mmol) of N-[3-{3,4-di($\beta$-methoxyethoxy)phenyl}-2-propenoyl]-5-chloro-2-hydroxyaniline.

To a solution of 110 mg (0.23 mmol) of the amide product in 5 ml of methanol was added in an argon atmosphere 6 mg (0.03 mmol) of p-toluenesulfonic acid. The mixture was heated under reflux for 5 hours. The reaction solution was concentrated under reduced pressure, and the residue thus obtained was subjected to Sephadex LH-20 column chromatography. There was obtained from a fraction eluted with methanol 54 mg (0.18 mmol) of N-{3-(3,4-dihydroxyphenyl)-2-propenoyl}-5-chloro-2-hydroxyaniline.

Spectrophotometric data of the product support the structure shown below.

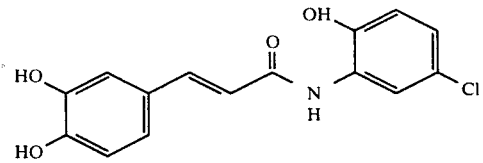

IR $\nu_{max}^{KBr}$ (cm$^{-1}$) 3335, 1655, 1600, 1580, 1525.
$^1$H-NMR (deutero acetone) δ:6.53–7.16 (6H, m), 7.50 (1H, d, J=16Hz), 7.72 (1H, d, J=2Hz).

EXAMPLE 11

To a solution of 1.21 g (3.40 mmol) of 3-{3,4-di-($\beta$-methoxyethoxymethoxy)phenyl}-2-propenic acid in dry acetonitrile (30 ml) were added in an argon atmosphere 1.73 g (6.76 mmol) of 2-chloro-1-methylpyridinium iodide and 2.40 ml (17.2 mmol) of triethylamine and 799 mg (7.32 mmol) of o-aminophenol, successively. The mixture was reacted at room temperature for 60 hours, followed by addition of water. The mixture was extracted with ethyl acetate, and the organic layer was successively washed with 1N-aqueous hydrochloric acid, water, aqueous solution of sodium carbonate and water. The organic layer was concentrated under reduced pressure, and the residue thus obtained was subjected to silica gel column chromatography. There was obtained 188 mg (0.420 mmol) of N-[3-{3,4-di($\beta$-methoxyethoxymethoxy)phenyl}-2-propenoyl]-o-aminophenol.

To a solution of 188 mg (0.420 mmol) of the amide compound prepared above in methanol (20 ml) was added 52 mg (0.273 mmol) of p-toluenesulfonic acid hydrate. The mixture was refluxed in an argon atmosphere for 30 min. Water was added to the reaction solution, and the mixture was extracted with ethyl acetate. The organic layer was concentrated under reduced pressure, and the residue thus obtained was subjected to Sephadex LH-20 column chromatography. There was obtained from a fraction eluted with methanol 85 mg (0.313 mmol) of N-{3-(3,4-dihydroxyphenyl)-2-propenoyl}-o-aminophenol.

Spectrophotometric data of the product support the structure shown below.

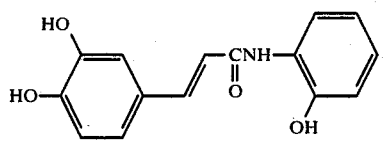

IR $\nu_{max}^{KBr}$ (cm$^{-1}$) 3300, 1660. 1600.

$^1$H-NMR (deutero acetone) δ: 6.63–7.17 (7H, m), 7.42–7.77 (2H, m), 8.40 (4H, bs).

EXAMPLE 12

To a solution of 505 mg (1.4 mmol) of 3-{3,4-di(β-methoxyethoxymethoxy)phenyl}-2-propenic acid in dry 1,2-dichloroethane (20 ml) were added in an argon atmosphere 20 mg (0.16 mmol) of dimethylaminopyridine and 487 mg (2.36 mmol) of N,N'-dicyclohexylcarbodiimide. The mixture was reacted at room temperature for 15 min. To the reaction mixture was added 3.2 ml of the triethylamine solution of N-(p-chlorobenzhydryl)-N'-(2-aminoethyl)piperadine employed in Example 1. The mixture was reacted at room temperature for 20 hours. The reaction solution was treated in the same way as in Example 1 to give 80 mg (0.12 mmol) of N-(p-chlorobenzhydryl)-N'-[2-{3,4-di(β-methoxyethoxymethoxy)phenyl}-2-propenoyl}-aminoethyl]piperazine.

To a solution of 80 mg (0.12 mmol) of the amide product prepared above in 5 ml of methanol was added 32 mg (0.17 mmol) of p-toluenesulfonic acid hydrate. The mixture was heated under reflux in an argon atmosphere for 2.5 hours.

To the reaction solution was added saturated solution of sodium hydrogen carbonate, and the mixture was extracted with ethyl acetate. The resulting organic layer was concentrated under reduced pressure, and the residue was subjected to Sephadex LH-20 column chromatography. There was obtained from a fraction eluted with methanol 40 mg (0.08 mmol) of N-(p-chlorobenzhydryl)-N'-[2-{3-(3,4-dihydroxyphenyl)-2-propenoyl}aminoethyl]piperazine.

Spectrophotometric data of the product support the structure shown below.

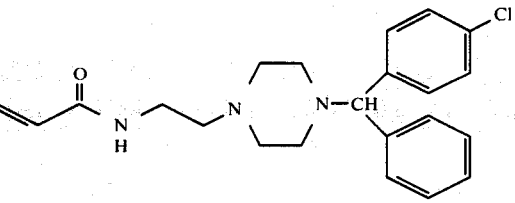

IR $\nu_{max}^{KBr}$ (cm$^{-1}$) 3550, 3400, 1670.

EXAMPLE 13

To a solution of 360 mg (1.17 mmol) of 5-(3-methoxy-4-β-methoxyethoxymethoxyphenyl)-2,4-pentadienic acid in dry acetonitrile (5 ml) were added in an argon atmosphere 365 mg (1.43 mmol) of 2-chloro-1-methylpyridinium iodide, 0.400 ml (2.87 mmol) of triethylamine and 0.180 ml (1.39 mmol) of methyl anthranylate, successively. The mixture was refluxed for 7 hours. The reaction solution was concentrated under reduced pressure. Water was added to the residue thus obtained, and the mixture was extracted with chloroform. The organic layer was dried over sodium sulfate and then concentrated under reduced pressure. The residue thus obtained was subjected to purification procedures using silica gel thin layer chromatography (chloroform : ethanol=20:1) to yield 160 mg (0.362 mmol) of methyl N-5-(3-methoxy-4-β-methoxyethoxymethoxyphenyl)-2,4-pentadienoylanthranilate.

To a solution of 112 mg (0.254 mmol) of the amide compound prepared above in a solution of MeOH (2 ml) and water (0.5 ml) was added 138 mg (3.45 mmol) of sodium hydroxide. The mixture was reacted at room temperature for 6 hours. The reaction solution was adjusted with 1N-aqueous hydrochloric acid to a pH of 3, followed by extraction with ethyl acetate. The organic layer was concentrated under reduced pressure. To the residue was added 5 ml of 80% aqueous acetic acid. The mixture was reacted in an argon atmosphere at 100° C. for 7 hour 30 min. The reaction solution was concentrated under reduced pressure, and the residue thus obtained was subjected to Sephadex LH-20 column chromatography. There was obtained from a fraction eluted with methanol 74 mg (0.218 mmol) of N-5-(3-methoxy-4-hydroxyphenyl)-2,4-pentadienoylanthranilic acid. Spectrophotometric data of the product support the structure shown below.

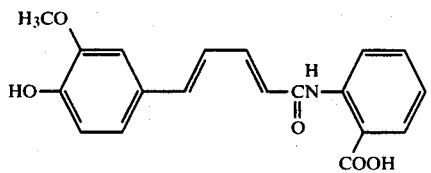

IR $\nu_{max}^{KBr}$ (cm$^{-1}$) 3450, 1685, 1610, 1590.

$^1$H-NMR (deutero dimethylsulfoxide) δ: 3.86 (3H, s), 6.19 (1H, d, J=14Hz), 6.80–7.54 (8H, m), 8.06 (1H, d, J=6 Hz), 8.62 (1H, d, J=8Hz).

EXAMPLE 14

To a solution of 407 mg (1.32 mmol) of 5-(3-methoxy-4-β-methoxyethoxymethoxyphenyl)-2,4-pentadienic acid in dry acetonitrile (4 ml) were added in an argon atmosphere 389 mg of 2-chloro-1-methylpyridinium iodide and 0.450 ml (3.23 ml) of triethylamine. The mixture was reacted at room temperature for 30 min., followed by addition of a solution of 54 mg (0.613 mmol) of 1,4-diaminobutane in dry acetonitrile (2 ml). The resulting mixture was reacted at room temperature for 2 hour 45 min., followed by addition of water. The mixture was extracted with chloroform, and the organic layer was washed with water and dried over anhydrous sodium sulfate. The dried mass was concentrated under reduced pressure, and the residue thus obtained was subjected to silica gel column chromatography. There was obtained from a fraction eluted with chloroform 287 mg (0.429 mmol) of N,N'-di{5-(3-methoxy-4-β-methoxyethoxymethoxyphenyl)-2,4-pentadienoyl}-1,4-diaminobutane.

To a solution of 126 mg (0.188 mmol) of the amide compound prepared above in methanol (8 ml) was added 4 mg (0.0232 mmol) of p-toluenesulfonic acid, and the mixture was refluxed for 7 hours. The reaction mixture was concentrated under reduced pressure, and the residue thus obtained was recrystallized from methanol to give 51 mg (0.104 mmol) of N,N'-di{5-(3-methoxy-4-hydroxyphenyl)-2,4-pentadienoyl}-1,4-diaminobutane. Spectrophotometric data of the product support the structure shown below.

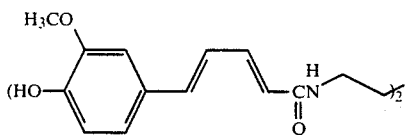

IR $\nu_{max}^{KBr}$ (cm$^{-1}$): 3420, 3300, 1650, 1600, 1590
$^1$H-NMR (deutero-dimethylsulfoxide) δ: 1.50 (2H, bs), 3.32 (2H, bs), 3.85 (3H, s), 6.08 (1H, d, J=15Hz), 6.68–7.40 (6H, m), 8.00 (1H, bs), 9.28 (1H, bs).

EXAMPLE 15

To a solution of 15.2 g (0.10 mol) of vanillin in 200 ml of dichloroethane were added in an argon atmosphere 13 ml (0.114 mol) of β-methoxyethoxymethyl chloride and 21 ml (0.121 mol) of diisopropylethylamine. The mixture was heated under reflux for 3 hours, followed by addition of water. The mixture was extracted with chloroform, and the organic layer was dried over anhydrous sodium sulfate and then concentrated under reduced pressure. The residue thus obtained was subjected to silica gel column chromatography. There was obtained from a fraction eluted with benzene - ethyl acetate (10:1) 22 g (0.092 mol) of 3-methoxy-4-β-methoxyethoxymethoxybenzaldehyde.

In 100 ml of dry tetrahydrofuran was dissolved 1.133 g (47 mmol) of the aldehyde prepared above. Separately, to 150 ml of dry tetrahydrofuran were added in an argon atmosphere 2 g (50 mmol) of 60 % sodium hydride and then 11 ml (50 mmol) of triethyl 4-phosphonocrotonate. The mixture was reacted at room temperature for 30 min. To the reaction solution was added the tetrahydrofuran solution of the aldehyde prepared above. The mixture was reacted at room temperature for 3 hours, followed by addition of saturated aqueous solution of ammonium chloride. The resulting mixture was extracted with ethyl acetate.

The organic layer was concentrated under reduced pressure, and the residue thus obtained was subjected to silica gel column chromatography. There was obtained from a fraction eluted with benzene - acetone (9:1) 9.0 g (27 mmol) of ethyl 5-(3-methoxy-4-β-methoxyethoxymethoxyphenyl)-2,4-pentadienate.

Then, to a solution of 8.8 g (26 mmol) of the ester prepared above in 100 ml of methanol were added in an argon atmosphere 25 ml of water and 10.4 g (260 mmol) of sodium hydroxide. The mixture was reacted at room temperature for 1 hour. 6N-hydrochloric acid was added to the reaction solution to adjust the pH to 4, followed by addition of 200 ml of water. The resulting mixture was extracted with ethyl acetate, and the organic layer was concentrated under reduced pressure to give 7.6 g (24.7 mmol) of 5-(3-methoxy-4-β-methoxyethoxymethoxyphenyl)-2,4-pentadienic acid.

Then, to a solution of 2.08 g (6.74 mmol) of the carboxylic acid prepared above in dry dichloroethane (40 ml) were added 996 mg (8.36 mmol) of 2-mercaptothiazoline, 109 mg (0.892 mmol) of dimethylaminopyridine and 1.82 g (8.83 mmol) of N,N'-dicyclohexylcarbodiimide. The mixture was reacted in an argon atmosphere at room temperature for 14 hours. Precipitates then formed were removed by filtration, and the filtrate was concentrated under reduced pressure. The residue thus obtained was subjected to silica gel column chromatography. There was obtained from a fraction eluted with chloroform 2.62 g (6.40 mmol) of N-5-(3-methoxy-4-β-methoxyethoxymethoxyphenyl)-2,4-pentadienoyl-2-thiothiazolidine.

To a solution of 542 mg (1.32 mmol) of the amide compound prepared above in 10 ml of tetrahydrofuran was added in an argon atmosphere a solution of 603 mg (2.39 mmol) of benzhydrylpiperazine in tetrahydrofuran (10 ml). The mixture was reacted at room temperature for 10 min., followed by addition of 40 ml of 2N-aqueous solution of sodium hydroxide. The resulting mixture was extracted with ethyl acetate, and the organic layer was concentrated under reduced pressure. The residue thus obtained was subjected to silica gel column chromatography. There was obtained from a fraction eluted with chloroform - methanol (100:1) 616 mg (1.14 mmol) of 1-benzhydryl-4-{5-(3-methoxy-4-β-methoxyethoxymethoxyphenyl)-2,4-pentadienoyl}piperazine.

To a solution of 120 mg (0.221 mmol) of the amide compound prepared above was added in an argon atmosphere 46 mg (0.242 mmol) of p-toluenesulfonic acid hydrate. The mixture was refluxed for 1 hour. The reaction solution was concentrated under reduced pressure, followed by addition of water. The resulting mixture was adjusted with aqueous solution of sodium carbonate to a pH of 10, followed by extraction with ethyl acetate. The organic layer was concentrated under reduced pressure, and the residue thus obtained was subjected to silica gel thin layer chromatography. Development with chloroform-methanol (40:1) yielded 86 mg (0.189 mmol) of 1-benzhydryl-4-{5-(3-methoxy-4-hydroxyphenyl)-2,4-pentadienoyl }piperazine. Spectrophotometric data of the product support the structure shown below.

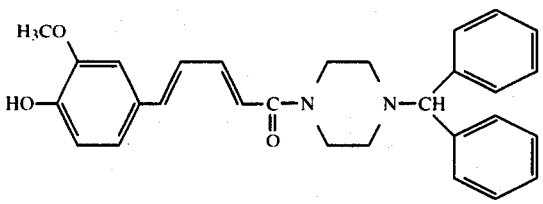

IR $\nu_{max}^{KBr}$: (cm$^{-1}$) 3450, 1640, 1585.

$^1$H-NMR (deutero-chloroform) 67 :2.40 (4H, bs), 3.63 (4H, bs), 3.83 (3H, s), 4.23 (1H, s), 6.35 (1H, d, J=15Hz), 6.70–7.25 (16H, m).

EXAMPLE 16

To a solution of 2.12 g (7.41 mmol) of N-(p-chlorobenzhydryl)piperazine in triethylamine (11 ml) was added in an argon atmosphere 868 mg (7.48 mmol) of 2-chloroethylamine hydrochloride. The mixture was refluxed for 8 hours. To a solution of 496 mg (1.21 mmol) of N-{5-(3-methoxy-4-β-methoxyethoxymethoxyphenyl)-2,4-pentadienoyl }-2-thiothiazolidine in dry dimethylformamide (5 ml) was added 1.50 ml of the solution prepared above. The mixture was reacted in an argon atmosphere at room temperature for 24 hours. The reaction solution was concentrated under reduced pressure, and the residue thus obtained was subjected to silica gel column chromatography. There was obtained from a fraction eluted with chloroform - methanol (20:1) 148 mg (0.239 mmol) of N-(p-chlorobenzhydryl)-N'-[2-{5-(3-methoxy-4-β-methoxyethoxymethoxyphenyl)-2,4-pentadienoyl}aminoethyl]-piperazine.

To a solution of 148 mg (0.239 mmol) of the amide compound prepared above in methanol (5 ml) was added 61 mg (0.321 mmol) of p-toluenesulfonic acid hydrate. The mixture was refluxed in an argon atmosphere for 2.5 hours, followed by addition of water. The resulting mixture was adjusted with an aqueous solution of sodium carbonate to a pH of 10, followed by extraction of ethyl acetate. The organic layer was concentrated under reduced pressure, and the residue thus obtained was subjected to silica gel thin layer chromatography. Development with chloroform - methanol (20:1) yielded 54 mg (0.102 mmol) of N-(p-chlorobenzhydryl)-N'-[2-{5-(3-methoxy-4-hydroxyphenyl)-2,4-pentadienoyl}aminoethyl]piperazine. Spectrophotometric data of the product support the structure shown below.

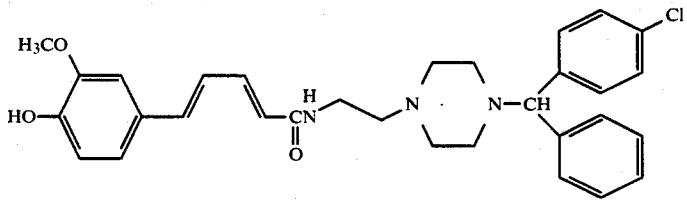

IR $\nu_{max}^{CHCl_3}$ $(cm-1)$ 3550, 3400, 1670, 1625, 1605

$^1$H-NMR (deutero-chloroform) δ: 2.47 (10H, bs), 3.45 (2H, bs), 3.83 (3H, s), 4.20 (1H, s), 5.73 (1H, bs), 6.05 (1H, d, J=15 Hz).

EXAMPLE 17

To a solution of 214 mg (0.888 mmol) of pyridoxamine dihydrochloride in dry dimethylformamide (6 ml) was added in an argon atmosphere 0.720 ml (5.17 mmol) of triethylamine. The mixture was reacted at room temperature for 7 hours, followed by addition of a solution of 322 mg (0.786 mmol) of N-{5-(3-methoxy-4-β-methoxyethoxymethoxyphenyl)-2,4-pentadienoyl}-2-thiothiazolidine in dry dimethylformamide (6 ml). The mixture was reacted at room temperature for 15 hours. The reaction mixture was concentration under reduced pressure, and water was added to the residue then obtained. The resulting mixture was extracted with ethyl acetate, and the organic layer was concentrated under reduced pressure. The residue thus obtained was subjected to silica gel column chromatography. There was obtained from a fraction eluted with chloroform-methanol (20:1) 172 mg (0.375 mmol) of N-{5-(3-methoxy-4-β-methoxyethoxymethoxyphenyl)-2,4-pentadienoyl}pyridoxamine.

To a solution of 172 mg (0.375 mmol) of the amide compound prepared above in methanol (5 ml) was added 73 mg (0.384 mmol) of p-toluenesulfonic acid hydrate. The mixture was refluxed in an argon atmosphere for 2.5 hours, followed by addition of water. The resulting mixture was adjusted with an aqueous solution of sodium carbonate to a pH of 10, followed by extraction with ethyl acetate. The organic layer was concentrated under reduced pressure, and the residue thus obtained was recrystallized from methanol to give 41 mg (0.111 mmol) of N-{5-(3-methoxy-4-hydroxyphenyl)-2,4-pentadienoyl}pyridoxine. Spectrophotometric data of the product support the structure shown below.

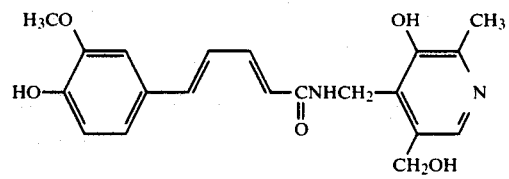

IR $\nu_{max}^{KBr}$ (cm$^{-1}$): 3400, 1640, 1580.

1H-NMR deutero-dimethylsulfoxide) δ: 2.33 (3H, s), 3.80 (3H, s), 4.37 (2H, d, J=6Hz), 4.58 (2H, d, J=5Hz), 6.08 (1H, d, J=14Hz), 6.63–7.33 (6H, m), 7.87 (1H, s).

EXAMPLE 18

To a solution of 557 mg (6.32 mmol) of 1,4-diaminobutane in dry dimethylformamide (10 ml) was added in an argon atmosphere a solution of 426 mg (1.04 mmol) of N-{5-(3-methoxy-4-β-methoxyethoxymethoxyphenyl)-2,4-pentadienoyl}-2-thiothiazolidine in dry dimethylformamide (10 ml). The mixture was reacted at room temperature for 1 hour 45 min. and then concentrated under reduced pressure. To the residue thus obtained were added 10 ml of pyridine and 5 ml of acetic anhydride. The mixture was reacted at room temperature for 21 hours and then concentrated under reduced pressure. The residue thus obtained was subjected to silica gel column chromatograpy. There was obtained from a fraction eluted with chloroform - methanol (20:1) 192 mg (0.457 mmol) of N-{5-(3-methoxy-4-β-methoxyethoxymethoxyphenyl)-2,4-pentadienoyl}-N'-acetyl-1,4-diaminobutane.

To a solution of 192 mg (0.457 mmol) of the amide compound prepared above in methanol (6 ml) was added 14 mg (0.074 mmol) of p-toluenesulfonic acid hydrate. The mixture was refluxed in an argon atmosphere for 1 hour. The reaction solution was concentrated under reduced pressure, and water was added to the residue thus obtained. The resulting mixture was adjusted with sodium carbonate to a pH of 10, followed by extraction with n-butanol. The organic layer was concentrated under reduced pressure, and the residue thus obtained was recrystallized from methanol to give 55 mg (0.166 mmol) of N-{5-(3-methoxy-4-hydroxyphenyl)-2,4-pentadienoyl}-N'-acetyl-1,4-diaminobutane. Spectrophotometric data of the produce support the structure shown below.

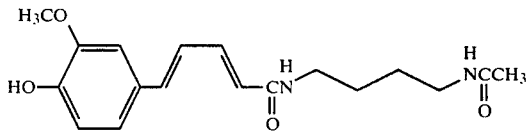

IR $\nu_{max}^{KBr}$ (cm$^{-1}$): 3450, 1645, 1590.

$^1$H-NMR (deutero-dimethylsulfoxide) δ: 1.47 (4H, bs), 1.83 (3H, s), 3.22 (4H, bs), 3.80 (3H, s), 5.98 (1H, d, J=14Hz), 6.57 -7.18 (6H, m).

EXAMPLE 19

To a solution fo 880 mg (10 mmol) of 1,4-diaminobutane in tetrahydrofuran (20 ml) was added in an argon atmosphere a solutin fo 410 mg (1 mmol) of N-{5-(3-methoxy-4-β-methoxyethoxymethoxyphenyl)-2,4-pentadienoyl}-2-thiothiazolidine in tetrahydrofuran (10 ml) at room temperature over 30 min. The mixture was treated in the same way as in Example 3 to react with 390 mg (1.05 mmol) of α-linolenic acid thiazolidinethionamide. The reaction product was treated in the same way as in Example 3 to hydrolyze N-{5-(3-methoxy-4-β-methoxyethoxymethoxyphenyl)-2,4-pentadienoyl}-N'-9,12,15-octadecatrieneo yl-1,4-diaminobutane with 1,4-dioxane - acetic acid-water (5:4:1). The reaction product was treated in the same way as in Example 3 to give 195 mg (0.35 mmol) of N-{5-(3-methoxy-4-hydroxyphenyl)-2,4-pentadienoyl}-N'- 9,12,15-octadecatrienoyl-1,4-diaminobutane. Spectrophotometric data of the product support the structure shown below.

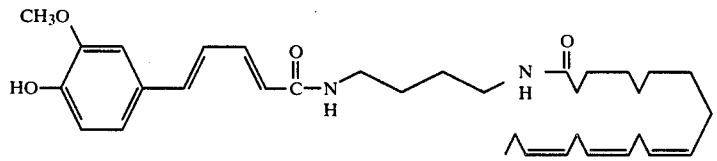

IR$\nu_{max}^{KBr}$ (cm$^{-1}$): 3400, 1645, 1600

EXAMPLE 20

To a solution of 221 mg (0.457 mmol) of N-5-{3,4-di(β-methoxyethoxymethoxy)phenyl}-2,4-pentadienoyl-2-thiothiazolidine in dry dimethylformamide (10 ml) was added in an argon atmosphere a solution of 420 mg (4.76 mmol) of 1,4-diaminobutane in dry dimethylformamide (10 ml). The mixture was reacted at room temperature for 2 hours. The reaction solution was concentrated under reduced pressure. To the residue thus obtained were added pyridine (2 ml) and acetic anhydride (2 ml). The mixture was reacted at room temperature for 3 hours. The reaction solution was concentrated under reduced pressure, and the residue thus obtained was subjected to silica gel column chromatography. There was obtained from a fraction eluted with chloroform - methanol 98 mg (0.198 mmol) of N-[5-{3,4-di(β-methoxyethoxymethoxy)phenyl}-2,4-pentadienoyl]-N'-acetyl-1,4-diaminobutane.

A solution of 75 mg (0.152 mmol) of the amide compound prepared above in 80% aqueous acetic acid (5 ml) was reacted at 110° C. for 1 hour. The reaction solution was concentrated under reduced pressure, and the residue thus obtained was subjected to silica gel column chromatography. There was obtained from a fraction eluted with chlorofor-methanol (5:1) 39 mg (0.123 mmol) of N-{5-(3,4-dihydroxyphenyl)-2,4-pentadienoyl}-N'-acetyl-1,4-diaminobutane. Spectrophotometric data of the product support the structure shown below.

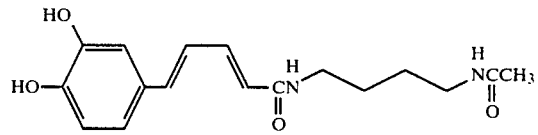

IR$\nu_{max}^{KBr}$ (cm$^{-1}$): 3400, 1655, 1595

$^1$H-NMR (deutero-acetone, pyridine) δ: 1.48 (4H, bs), 1.93 (3H, s), 3.32 (4H, bs), 6.2 (1H, d, J=15 Hz), 6.78–7.97 (6H, m).

EXAMPLE 21

A solution of 165 mg (0.341 mmol) of N-5-{3,4-di(β-methoxyethoxymethoxy)phenyl}-2,4-pentadienoyl-2-thiothiazolidine in tetrahydrofuran (4 ml) was added in an argon atmosphere to a solution of 12 mg (0.136 mmol) of 1,4-diaminobutane in dimethylformamide (4 ml). The mixture was reacted at room temperature for 4 hours. The reaction solution was concentrated under reduced pressure, and the residue thus obtained was subjected to silica gel column chromatography. There was obtained from a fraction eluted with chloroform - methanol (20:1) 97 mg (0.151 mmol) of N,N'-di[5-{3,4-di(β-methoxyethoxymethoxy)phenyl}-2,4-pentadienoyl]-1,4-diaminobutane.

To a solution of 97 mg (0.151 mmol) of the amide compound prepared above in methanol (10 ml) was added 4 mg (0.0232 mmol) of p-toluenesulfonic acid. The mixture wa refluxed in an argon atmosphere for 9 hours. The reaction solution was recrystallized at −20° C. to give 17 mg (0.0366 mmol) of N,N'-di[5-(3,4-dihydroxyphenyl)-2,4-pentadienoyl]-1,4-diaminobutane. Spectrophotometric data of the product support the structure shown below.

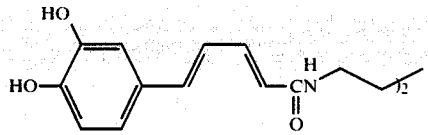

aenoyl-1,4-diaminobutane. Spectrophotometric data of the product support the structure shown below.

IR$\nu_{max}$ $CHCl_3$ (cm$^{-1}$): 3455, 3285, 1650, 1600, 1515.

$^1$H-NMR (deutero pyridine) δ: 0.93 (3H, t, J=7.5 Hz), 1.57-2.70 (10H), 2.94 (10H, bt, J=5.5 Hz), 3.30-3.67 (4H), 5.49 (12H, bt, J=5.5 Hz), 6.34 (1H, d, J=15 Hz), 6.80-7.67 (6H).

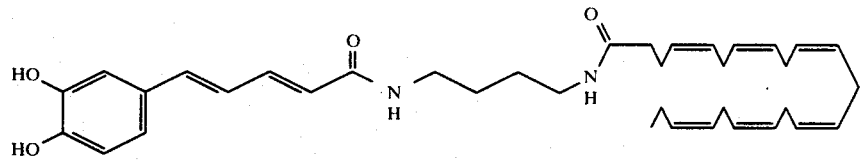

IR$\nu_{max}$ $^{KBr}$ (cm$^{-1}$): 3500, 3350, 1640, 1620, 1595.

$^1$H-NMR (deutero dimethylsulfoxide) δ: —1.48 (2H, bs), 3.16 (2H, s), 6.08 (1H, d, J=15 Hz), 6.72-7.35 (6H, m), 7.98 (1H, t, J=6H), 8.97 (1H, bs), 9.24 (1H, bs).

EXAMPLE 22

To a solution of 518 mg (5.88 mmol) of 1,4-diaminobutane in tetrahydrofuran (20 ml) at room temperature was added in an argon atmosphere a solution of 281 mg (0.65 mmol) of N-5-[3,4-di(β-methoxyethoxymethoxy)phenyl]-2,4-pentadienoyl-2-thiothiazolidine in tetrahydrofuran (5 ml). The mixture was reacted at room temperature for 12 min., followed by addition of 25 ml of 2N-aqueous solution of sodium hydroxide. The resulting mixture was extracted three times with chloroform. The organic layer of the extract was washed with water and dried over anhydrous magnesium sulfate, and then the solvent was removed by distillation under reduced pressure to give 289 mg of an extraction residue.

To a solution of 289 mg of the residue in tetrahydrofuran (6 ml) at room temperature was added in an argon atmosphere a solution of 281 mg (0.65 mmol) of 4,7,10,13,16,19-docosahexaenic acid thiazolidinethionamide in tetrahydrofuran (2 ml). The mixture was reacted at room temperature for 2 hour 20 min., followed by addition of 25 ml of 2N-aqueous solution of sodium hydroxide. The resulting mixture was extracted three times with dichloromethane. Organic layer of the extract was washed with water and dried over anhydrous sodium sulfate, and then the solvent was removed by distillation under reduced pressure to give 488 mg of an extraction residue. The residue was subjected to silica gel chlumn chromatography. There was obtained from a fraction eluted with chloroform - methanol (99:1) 321 mg (0.42 mmol) of N-5-[3,4-di(β-methoxyethoxymethoxy)-phenyl]-2,4-pentadienoyl-N'-4,7,10,13,16,19-docosahexaenoyl-1,4-diaminobutane.

A solution of 245 mg (0.32 mmol) of the compound above dissolved in an argon atmosphere in a mixed solvent of 1,4-dioxane, acetic acid and water (5:4:1) (10 ml) was reacted with heating under reflux for 31 hours. The solvent was removed by distillation under reduced pressure to give 201 mg of a residue. The residue was subjected to Sephadex LH-20 column chromatography. There was obtained 110 mg of a crude product from a fraction eluted with methanol. The crude product was purified by preparative silica gel thin layer chromatography to give 72 mg (0.12 mmol) of N-5-(3,4-dihydroxyphenyl)-2,4-pentadienoyl-N'-4,7,10,13,16,19-docosahex-

EXAMPLE 23

To a solution of 423 mg (4.80 mmol) of 1,4-diaminobutane in tetrahydrofuran (17 ml) at room temperature was added in an argon atmosphere 245 mg (0.51 mmol) of N-5-[3,4-di(β-methoxyethoxymethoxy)-phenyl]-2,4-pentadienoyl-2-thiothiazolidine in tetrahydrofuran (4 ml). The mixture was reated at room temperature for 35 min., followed by addition of 20 ml of 2N-aqueous solution of sodium hydroxide. The resulting mixture was extracted three times with chloroform, and the organic layer of the extract was washed with water and dried over anhydrous magnesium sJbvHlfate. The solvent was removed by distillation under reduced pressure to give 285 mg of a residue.

To a solution of 285 mg of the residue in tetrahydrofuran (6 ml) at room temperature was added in an argon atmosphere 197 mg (0.53 mmol) of d-linolenic acid thiazolidinethionamide in tetrahydrofuran (2 ml). The mixture was reacted at room temperature for 90 min., followed by addition of 20 ml of 2N-aqueous solution of sodium hydroxide. The resulting mixture was extracted three times with dichloromethane, and the organic layer of the extract was washed with water and dried over anhydrous magnesium sulfate. The solvent was then removed by distillation under reduced pressure to give 375 mg of an extraction residue. The residue was subjected to silica gel column chromatography. There was obtained from a fraction eluted with chloroform -methanol (99:1) 223 mg (0.31 mmol) of N-5-[3,4-di(β-methoxyethoxymethoxy)phenyl]-2,4-pentadienoyl-1,4-diaminobutane.

A solution of 188 mg (0.26 mmol) of the aboveprepared compound dissolved in an argon atmosphere in a mixed solvent of 1,4-dioxane, acetic acid and water (5:4:1) (10 ml) was reacted with heating under reflux for 30 hours. The solvent was removed by distillation under reduced pressure to give 146 mg of a residue. The residue was subjected to Sephadex LH-20 column chromatography. There was obtained 59 mg of a crude product from a fraction eluted with methanol. The crude product was recrystallized from methanol - water (2:1) to give 54 mg (0.10 mmol) of N-5-(3,4-dihydroxyphenyl)2,4-pentadienoyl-N'-9,12,15-octadecatrienoyl-1,4-diaminobutane. Slpectrophotometric data of the product support the structure shown below.

IR$\nu_{max}$ $^{KBr}$ (cm$^{-1}$): 3410, 3290, 1643, 1603, 1545.

$^1$H-NMR (deutero pyridine) δ: 0.91(3H, t, J=7.5 Hz), 1.13-1.43 (10 H), 1.57-2.47 (10 H), 2.89 (4H, bt, J=5.5 Hz), 3.30-3.67 (4H), 5.33-5.57 (6H), 6.34 (1H, d, J=15 Hz), 6.83-7.67 (6H).

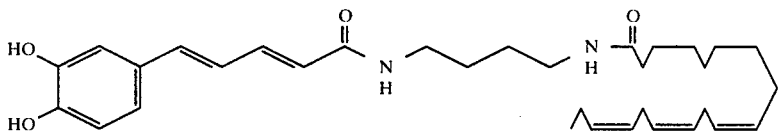

EXAMPLE 24

To a solution of 275 mg (0.719 mmol) of 5-{3,4-di(β-methoxyethoxymethoxy)phenyl}-2,4-pentadienic acid in dry acetonitrile (4 ml) were added in an argon atmosphere 551 mg (2.16 mmcl) of 2-chloro-1-methylpyridinium iodide, 0.400 ml (2.87 mmol) of triethylamine and 0.120 ml (0.927 mmol) of methyl anthranilate. The mixture was refluxed for 7 hours. The reaction solution was concentrated under reduced pressure, and water was added to the residue thus obtained. The resulting mixture was extracted with chloroform, and the organic layer was dried over anhydrous sodium sulfate and then concentrated under reduced pressure. The residue thus obtained was subjected to silica gel column chromatography. There was obtained from a fraction eluted with hexane-ethyl acetate (1:1) 104 mg (0.202 mmol) of methyl N-5-{3,4-di(β-methoxyethoxymethoxy)phenyl}-2,4-pentadienoylanthranilate.

To a solution of 104 mg (0.202 mmol) of the amide compound prepared above in a solution of MeOH (4 ml) and water (1 ml) was added 122 mg (3.05 mmol) of sodium hydroxide. The mixture was reacted at room temperature for 1 hour 30 min. The reaction solution was neutralized with 1N-aqueous hydrochloric acid, followed by extraction with ethyl acetate. The organic layer was concentrated under reduced pressure, and the residue thus obtained was subjected to purification procedures using silica gel thin layer chromatography to give 87 mg (0.174 mmol) of N-5-{3,4-di(β-methoxyethoxymethoxy)phenyl}-2,4-pentadienoylanthranilic acid.

A solution of 87 mg (0.174 mmol) of the carboxylic acid prepared above in 5 ml of 80% aqueous acetic acid was reacted in anJbvHargon atmosphere at 130° C. for 4 hours. Water was added to the reaction solution, and precipitates then formed were collected. The presipitates were subjected to Sephadex LH-20 column chromatography. There was obtained from a fraction eluted with methanol 34 mg (0.105 mmol) of N-5-(3,4-dihydroxyphenyl)-2,4-pentadienoylanthranilic acid. Spectrophotometric data of the product support the structure shown below.

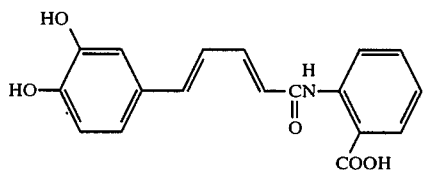

IR$\nu_{max}$ $^{KBr}$ (cm$^{-1}$): 3430, 1675, 1610, 1590.

$^1$H-NMR (deutero pyridine) δ: 6.32 (1H, d, J=15 Hz), 6.90–7.97 (8H, m), 8.50 (1H, d, J=7 Hz), 9.33 (1H, d, J=7 Hz).

EXAMPLE 25

To a solution of 286 mg (0.591 mmol) of N-5-{3,4-di(β-methoxyethoxymethoxy)phenyl}-2,4-pentadienoyl-2-thiothiazolidine in dimethylformamide (6 ml) was added 83 mg (0.761 mmol) of p-aminophenol. The mixture was reacted at room temperature for 36 hours. The reaction solution was concentrated under reduced pressure, and water was added to the residue then obtained. The resulting mixture was extracted with ethyl acetate, and the organic layer was concentrated under reduced pressure. The residue thus obtained was subjected to silica gel column chromatography. There was obtained from a fraction eluted with chloroform-methanol (100:1) 107 mg (0.226 mmcl) of N-5-{3,4-diβ-methoxyethoxy -methoxy)phenyl}-2,4-pentadienoylaminophenol.

To a solution of 57 mg (0.120 mmol) of the amide compound prepared above was added 4 mg (0.0232 mmol) of p-toluenesulfonic acid. The mixture was refluxed for 18 hours. The reaction solution was concentrated under reduced pressure, and the residue thus obtained was subjected to purification procedures using Silica gel thin layer chromatography (chloroform:methanol=8:1) to give 15 mg (0.0505 mmol) of N-5-(3,4-dihydroxyphenyl)-2,4-pentadienoylaminophenol. Spectrophotometric data of the product support the structure shown below.

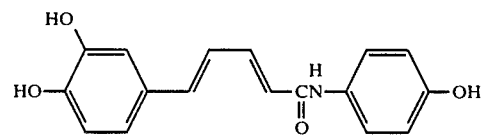

IR$\nu_{max}$ $^{KBr}$ (cm$^{-1}$): 3350, 1655, 1600.

$^1$H-NMR (deutero pyridine) δ: 6.57 (1H, d, J=15 Hz), 6.87–7.20 (7H, m), 7.43 (1H, s), 7.77–8.10 (3H, m).

EXAMPLE 26

To a solution of 470 mg (1.87 mmol) of benzhydrylpiperidine in 5 ml of tetrahydrofuran was added in an argon atmosphere a solution of 396 mg (0.82 mmol) of N-5-{3,4-di(β-methoxyethoxymethoxy)phenyl-2,4-pentadienoyl}-2-thio-thiazolidine in 5 ml of tetrahydrofuran. The mixture was reacted at room temperature for 10 min. To the reaction solution was added 20 ml of 2N-aqueous solution of sodium hydroxide, and the mixture was extracted with ethyl acetate. The organic jlayer was concentrated under reduced pressure, and the residue thus obtained was subjected to silica gel column chromatography. There was obtained from a fraction eluted with chloroform-methanol (100:1) 497 mg (0.81 mmol) of 1-benzhydryl-4-[5-{3,4-di(β-methoxyethoxymethoxy)phenyl}-2,4-pentadienoyl]piperidine.

To a solution of 472 mg (0.77 mmol) of the amide compound prepared above in 5 ml of methanol was added in an argon atmosphere 138 mg (0.80 mmol) of p-toluene-sulfonic acid. The mixture was heated under reflux for 3 hours. To the reaction solution was added 20 ml of saturated aqueous solution of sodium hydrogen carbonate, and the mixture was extracted with ethyl acetate. The organic layer was concentrated under reduced pressure, and the residue thus obtained was recrystallized from methanol to give 270 mg (0.61 mmol) of 1-benzhydryl-4-{5-(3,4-dihydroxyphenyl)-2,4-pentadienoyl}piperidine. Spectrophotometric data of the product support the structure shown below.

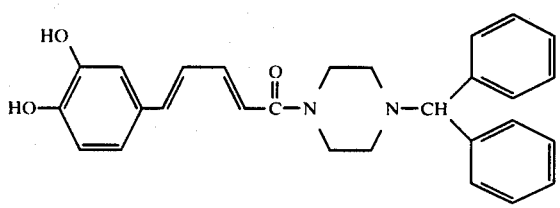

IR$\nu_{max}$ $^{KBr}$ (cm$^{-1}$): 3475, 3100, 1635, 1615, 1595, 1565.

$^1$H-NMR (deutero pyridine) δ: 2.33 (4H, m), 3.70 (4H, m), 4.28 (1H, s), 6.62 (1H, d, J=16 Hz), 6.90–8.10 (16 H, m).

EXAMPLE 27

To a solution of 393 mg (1.33 mmol) of N-benzhydryl-n'-(2-aminoethyl)piperazine in dry dimethylformamide (6 ml) was added in an argon atmosphere a solution of 677 mg (1.40 mmol) of N-[5-55 3,4-di(β-methoxyethoxymethoxy)-phenyl}-2,4-pentadienoyl]-2-thiothiazolidine in dry dimethylformamide (6 ml). The mixture was reacted at room temperature for 3 hours and then concentrated under reduced pressure. The residue thus obtained was subjected to silica gel column chromatography to give 289 mg (0.438 mmol) of N-benzhydryl-N'-[2-[5-{3,4-di(β-methoxyethoxymethoxy)-phenyl}-2,4-pentadienoyl]aminoethyl]-piperazine.

To a solution of 289 mg (0.438 mmol) of the amide compound prepared above in methanol (10 ml) was added 127 mg (0.668 mmol) of p-toluenesulfonic acid hydrate. The mixture was refluxed in an argon atmosphere for 7 hours. Water was added to the reaction mixture, and the mixture was adjusted with an aqueous solution of sodium carbonate to a pH of 9, followed by extraction with ethyl acetate. The organic layer was concentrated under reduced pressure, a the residue obtained was recrystallized from dichloromethane to give 101 mg (0.209 mmol) of N-benzhydryl-N'-[2-{5-(3,4-dihydroxyphenyl)-2,4-pentadienoyl}aminoethyl]-piperazine. Spectrophotometric data of the product support the structure shown below.

IR$\nu_{max}$$^{KBr}$ (cm$^{-1}$): 3400, 1655, 1600.

$^1$H-NMR (deutero pyridine) δ: 2.43 (10H, bs), 3.63 (2H, bs), 4.30 (1H, s), 6.32 (1H, d, J=15 Hz).

EXAMPLE 28

In the same way as in Example 1, 382 mg (1 mmol) of 5-{3,4-di(β-methoxyethoxymethoxy)phenyl}-2,4-pentadienic acid was reacted with N-(p-chlorobenzhydryl)-N'-(2-aminoethyl)piperazine. The amide product thus prepared was hydrolyzed with p-toluenesulfonic acid and treated in the same way as in Example 1 to give 47 mg (0.09 mmol) of N-(p-chlorobenzhydryl)-N'-[2-{5-(3,4-dihydroxyphenyl)-2,4-pentanoyl)}aminoethyl]piperazine.

Spectrophotometric data of the product support the structure shown below.

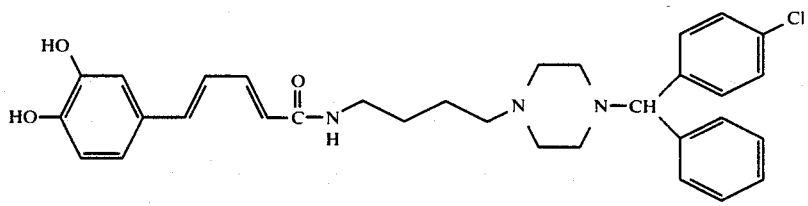

IR$\nu_{max}$$^{KBr}$ (cm$^{-1}$): 3550, 3400, 1670.

EXAMPLE 29

To 10 ml of acetonitrile was added in an argon atmosphere 468 mg (2 mmol) of 5-(3,4-dimethoxyphenyl)-2,4-pentadienic acid and then 0.28 ml (2 mmol) of triethylamine. To the resulting solution were added 511 mg (2 mmol) of 2-chloro-1-methylpyridinium iodide, 302 mg (2 mmol) of methyl anthranylate and 0.28 ml (2 mmol) of triethylamine. The mixture was heated under reflux for 8 hours. Water was added to the reaction solution and the mixture was extracted with ethyl acetate. The organic layer was concentrated under reduced pressure, and the residue thus obtained was subjected to silica gel column chromatography. There was obtained from a fraction eluted with benzene-ethyl acetate (19:1) 140 mg (0.38 mmol) of methyl N-{5-(3,4-dimethoxyphenyl)-2,4-pentadienoyl}anthranilate.

To a solution of 120 mg (0.33 mmol) of the amide product prepared above were added in an argon atmosphere 4 ml of water and then 0.5 g (12.5 mmol) of sodium hydroxide. The mixture was reacted at room temperature for 1.5 hours. To the reaction solution was added 1N-hydrochloric acid to adjust the pH to 1, and crystals then formed was separated by filtration and recrystallized from methanol. There was obtained 82 mg (0.23 mmol) of N-{5-(3,4-dimethoxyphenyl)-2,4-pentadienoyl}anthranilic acid. Spectrophotometric data of the product support the structure shown below.

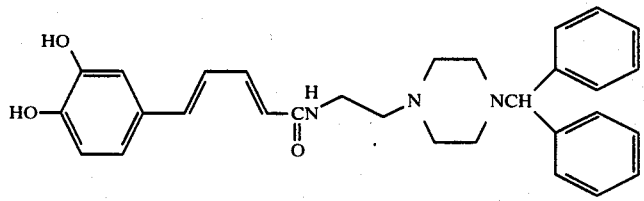

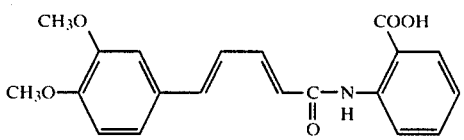

IR$\nu_{max}^{KBr}$ (cm$^{-1}$): 3300, 3275, 1670, 1600, 1570, 1520, 1505.

$^1$H-NMR (deutero acetone:deutero dimethylsulfoxide (1:1)} δ:3.78 (3H, s), 3.82 (3H, s), 6.17 (1H, d, J=15 Hz), 6.87–7.70 (8H, m), 7.95 (1H, d, d, J=8, 2 Hz), 8.63 (1H, d, d, J=8, 1 Hz).

EXAMPLE 30

To 200 ml of dry tetrahydrofuran was added in an argon atmosphere 4.31 g (0.108 mmol) of 60% sodium hydride. To the reaction solution cooled to 0° C. was added 25 ml (0.113 mmol) of triethyl 4-phosphono-crotonate, and the mixture was reacted at 0° C. for 30 min., followed by addition of 10 g (0.06 mol) of 3,4-dimethoxybenzaldehyde. The mixture was reacted at 0° C. for 1 hour and at room temperature for additional one hour, followed by addition of saturated aqueous solution of ammonium chloride. The mixture was extracted with ethylacetate, and the organic layer was concentrated under reduced pressure. The residue thus obtained was subjected to silica gel column chromatography. There was obtained from a fraction eluted with chloroform 9.6 g (0.0234 mol) of ethyl 5-(3,4-dimethoxyphenyl)-2,3-pentadienoate.

To a solution of 9.6 g (23.4 mmol) of the ester product prepared above in 100 ml of methanol were added in an argon atmosphere 25 ml of water and 10 g (250 mmol) of sodium hydroxide. The mixture was reacted at room temperature for 2 hours.

To the reaction solution was added 6N-hydrochloric acid to adjust the pH to 1, and precipitates then formed were separated by filtration and recrystallized from acetone. There was obtained 7.5 g (19.6 mmol) of 5-(3,4-dimethoxyphenyl)-2,4-pentadienic acid.

To a solution of 1.05 g (4.48 mmol) of the carboxylic acid thus obtained were added 716 mg (6.01 mmol) of 2-mercaptothiazoline, 62 mg (0.508 mmol) of dimethylaminopyridine and 1.22 g (5.91 mmol) of N,N'-dichlohexylcarbodiimide. The mixture was reacted at room temperature for 19 hours. Precipitates then formed were removed by filtration, and water was added to the filtrate, followed by extraction with chloroform. The organic layer was concentrated under reduced pressure, and the residue thus obtained was subjected to silica gel column chromatography. There was obtained from a fraction eluted with chloroform 1.12 g (3.34 mmol) of N-{5-(3,4-dimethoxyphenyl)-2,4-pentadienoyl}-2-thiothiazolidine.

To a solution of 2.12 g (7.41 mmol) of N-(p-chlorobenzhydryl)piperazine in triethylamine (11 ml) was added in an argon atmosphere 868 mg (7.48 mmol) of 2-chloroethylamine hydrochloride. The mixture was refluxed for 8 hours. Three (3.0) ml of the solution thus formed was added to a solution of 496 mg (1.48 mmol) of the N-{5-(3,4-dimethoxyphenyl)-2,4-pentadienoyl}-2-thiothiazolidine in dry tetrahydrofuran (10 ml). The mixture was reacted at room temperature for 60 hours, followed by addition of 1N-aqueous solution of sodium hydroxide. The mixture was extracted with chloroform, and the organic layer was washed with water. The organic layer was then concentrated under reduced pressure, and the residue thus obtained was subjected to silica gel column chromatography. There was obtained from a fraction eluted with chloroform-methanol (100:1) 228 mg (0.436 mmol) of N-(p-chlorobenzhydryl)-N'-[2-{5-(3,4-dimethoxyphenyl)-2,4-pentadienoyl}-aminoethyl]piperazine. Spectrophotometric data of the product support the structure shown below.

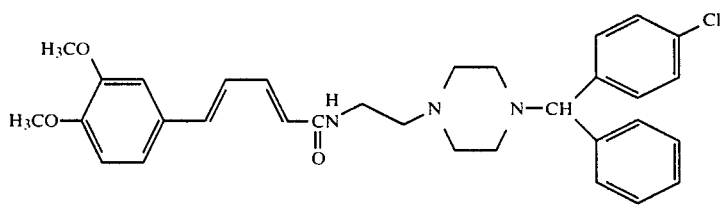

IR$\nu_{max}^{CHCl_3}$ (cm$^{-1}$): 3400, 1665, 1620, 1600.

$^1$H-NMR (deutero chloroform) δ:2.43 (10H, bs), 3.43(2H, bs), 3.85 (6H, s), 4.20 (1H, s), 5.97 (1H, d, J=15 Hz).

EXAMPLE 31

To a solution of 234 mg (1 mmol) of 5-(3,4-dimethoxyphenyl)-2,4-pentadienic acid in acetonitrile were added in an argon atmosphere 256 mg (1 mmol) of 2-chloro-1-methylpyridinium iodide, 0.28 ml (2 mmol) of triethylamine and 109 mg (1 mmol) of p-aminophenol. The mixture was reacted at room temperature for 15 hours. Water was added to the reaction solution, and the mixture was extracted with chloroform. The organic layer was concentrated under reduced pressure, and the residue thus obtained was subjected to silica gel column chromatography. There was obtained from a fraction eluted with chloroform-methanol (20:1) 210 mg (0.65 mmol) of N-{5-(3,4-dimethoxyphenyl)-2,4-pentadienoyl}-4-aminophenol. Spectrophotometric data of the product support the structure shown below.

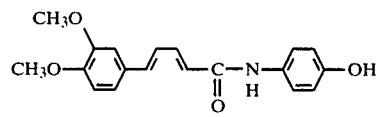

IR$\nu_{max}^{KBr}$ (cm$^{-1}$): 3400, 3225, 1650, 1610, 1590, 1510.

$^1$H-NMR {deutero dimethylsulfoxide-deutero acetone (1:1} δ:3.78 (3H, s), 3.82 (3H, s), 6.23 (1H, d, J=15 Hz), 6.67 (2H, d, J=9 Hz), 6.70–7.50 (6H, m), 7.47 (2H, d, J=9 Hz), 8.96 (1H, s), 9.63 (1H, s).

EXAMPLE 32

To a solution of 214 mg (0.89 mmol) of pyridoxamine dihydrochloride in dry dimethylformamide (6 ml) was added in an argon atmosphere 0.72 ml (5.17 mmol) of triethylamine. The mixture was reacted at room temperature for 7 hours, followed by addition of a solution of 268 mg (0.8 mmol) of N-{5-(3,4-dimethoxyphenyl)-2,4-pentadienoyl}-2-thiothiazolidine in dimethylformamide (6 ml). The resulting mixture was reacted at room temperature for 15 hours. The reaction mixture was then concentrated under reduced pressure, and water was added to the residue then obtained. The mixture was extracted with ethylacetate, and the organic layer was concentrated under reduced pressure. The residue thus obtained was subjected to silica gel column chromatography. There was obtained from a fraction eluted with chloroform - methanol (20:1) 161 mg (0.42 mmol) of N-{5-(3,4-dimethoxyphenyl)2,4-pentadienoyl} pyridoxamine. Spectrophotometric data of the product support the structure shown below.

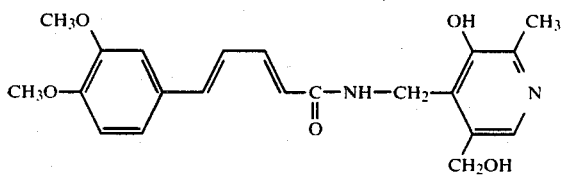

IR$\nu_{max}^{KBr}$ (cm$^{-1}$): 1650.

EXAMPLE 33

In the same way as in Example 3, 371 mg (0.65 mmol) of N-{5-(3,4-dimethoxyphenyl)-2,4-pentadienoyl}-N'-9,12,15-octadecatrienoyl-1,4-diaminobutane was prepared from 335 mg (1 mmol) of N-{5-(3,4-dimethoxyphenyl)-2,4-pentadienoyl}-2-thiothiazolidine, and 880 mg (10 mmol) of 1,4-diaminobutane, 390 mg of α-linolenic acid thiazolidinamide.

Spectrophotometric data of the product support the structure shown below.

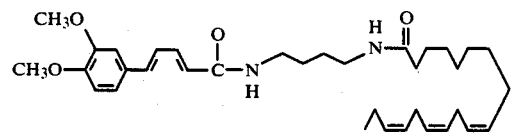

IR$\nu_{max}^{KBr}$ (cm$^{-1}$): 3400, 1650.

EXAMPLE 34

To a solution of 532 mg (1.984 mmol) of N-(3-bromopropyl)phthalimide in benzene (10 ml) was added in an argon atmosphere 745 mg (2.952 mmol) of benzohydrylpiperazine. The mixture was refluxed for 15 hours. Water was added to the reaction solution, and the mixture was adjusted with an aqueous solution of sodium carbonate to a pH of 10, followed by extraction with chloroform. The organic layer was concentrated under reduced pressure, and the residue thus obtained was subjected to silica gel column chromatography. There was obtained from a fraction eluted with chloroform 764 mg of N-benzohydryl-N'-(3-phthalylaminopropyl)-piperazine.

To a solution of 220 mg (0.5 mmol) of the piperazine derivative prepared above in ethanol (5 ml) was added 60 mg (1 mmol) of 80% aqueous solution of hydrazine hydrate. The mixture was heated under reflux for 2 hours. The reaction solution was concentrated under reduced pressure, and to the residue obtained was added dry dimethylformamide (5 ml). To the resulting solution was added a solution of 192 mg (0.5 mmol) of N-[3-{3-methoxy-4-(β-methoxyethoxymethoxy)-phenyl}-2-propenoyl]-2-thiothiazoline in dry dimethylformamide (5 ml). The mixture was reacted at room temperature for 3 hours. The solvent was removed by distillation under reduced pressure, and the residue thus obtained was subjected to silica gel column chromatography. There was obtained from a fraction eluted with chloroform-methanol (50:1) 187 mg (0.32 mmol) of N-benzhydryl-N'-[[3-{3-methoxy-4-(β-methoxyethoxymethoxy)phenyl}-2-propenoyl]n-aminopropyl]piperazine.

To a solution of 172 mg (0.3 mmol) of the amide compound prepared above in methanol (5 ml) was added 80 mg (0.42 mmol) of r-toluenesulfonic acid monohydrate. The mixture was heated under reflux for 1 hour. The solvent was removed by distillation under reduced pressure, and water was added to the residue obtained. The mixture was adjusted with an aqueous solution of sodium hydrogen carbonate to a pH of 10, followed by extraction with ethyl acetate. The organic layer was concentrated under reduced pressure, and the residue thus obtained was subjected to Sephadex LH-20 column chromatography. There was obtained from a fraction eluted with methanol 110 mg (0.22 mmol) of N-benzhydryl-N'-[}3-(3-methoxy-4-hydroxyphenyl)-2-propenoyl}-amino propyl]piperazine. Spectrophotometric data of the product support the structure shown below.

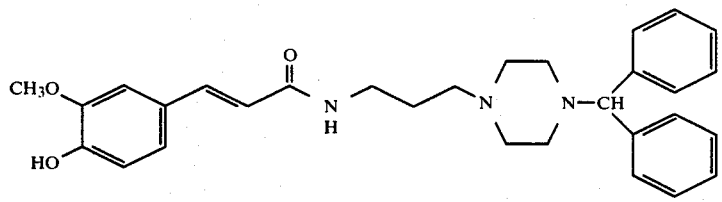

IR$\nu_{max}^{KBr}$ (cm$^{-1}$): 3400, 1660, 1620, 1595.

EXAMPLE 35

To a solution of 1.1 g (13.0 mmol) of putrescine in dry tetrahydrofuran (10 ml) was added in an argon atmosphere dropwise slowly a solution of 500 mg (1.30 mmol) of N-3-[3-methoxy-4-(β-methoxy)ethoxymethoxy]phenyl-2-butenoyl-2-mercaptothiazoline in dry tetrahydrofuran (10 ml). The mixture was sirred at room temperature for 30 min. The reaction solution was concentrated under reduced pressure, followed by arition extraction with n-butanol and 2N-aqueous solution of sodium hydroxide. The organic layer was washed with water and then concentrated under reduced pressure. The residue thus obtained, 232.5 mg (1.70 mmol) of anthranilic acid, 20.6 mg (0.17 mmol) of N,N-dimethylaminopyridine, and 348.6 mg (1.70 mmol) of dicyclohexyldiimide were dissolved in dry 1,2-dichloroethane (15 ml). The solution was stirred in an argon atmosphere at room temperature for 13 hours. The reaction solution was filtered, and the filtrate was concentrated under reduced pressure. The residue thus obtained was subjected to silica gel column chromatography. There was obtained from a fraction eluted with chloroformJbvHmethanol (20:1) 154.5 mg (0.33 mmol) of N-3-[3-methoxy-4-(β-methoxy)ethoxymethoxy]phenyl-2-butenoyl-N'-(2-amino)benzoylputrescine.

To a solution 154.5 mg (0.33 mmol) of the putrescine derivative thus obtained in methanol (15 ml) was added 186.6 mg (0.98 mmol) of paratoluenesulfonic acid. The mixture was heated in an argon atmosphere under reflux for 2 hour 30 min. The reaction solution was concentrated under reduced pressure, followed by partition extraction with ethyl acetate and saturated aqueous solution of sodium hydrogen carbonate. The organic layer was washed with water and saturated saline solution, and then concentrated under reduced pressure. The residue thus obtained was subjected to Sephadex column chromatography. Elution with methanol solvent yielded 95.2 mg (0.25 mmol) of N-3-[3-methoxy-4-hydroxy]pyenyl-2-butenoyl-N'-(2-amino)benzoylptolesine. Spectrophotometric data of the product support the structure shown below.

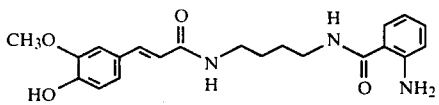

IR$\nu_{max}^{cm-1}$ (KBr): 3350, 1655, 1620, 1590.
$^1$H-NMR ((CD$_3$)$_2$CO) δ ppm: 1.57 (4H, m), 3.00–3.67 (4H, m), 3.75 (3H, s), 6.40 (1H, d, (J=15 Hz)), 6.37–7.40 (11H, m), 7.38 (1H, d(J=15 Hz)).

EXAMPLE 36

To 473 mg (1.86 mmol) of N-(2-bromoethyl)phthalimide was added 0.400 mg (0.73 mmol) of ethyl N-piperazinocarboxylate in an argon atmosphere. The mixture was reacted at 100° C.–110° C. for 1 hour. After cooled, water was added to the reaction mixture, followed by adjustment of the pH with an aqueous solution of sodium carbonate to 10. The resulting mixture was extracted with chloroform and the organic layer was concentrated under reduced pressure. The residue thus obtained was subjected to silica gel column chromatography. There was obtained from a fraction eluted with chloroform 493 mg (1.34 mmol) of N-ethoxycarbonyl-N'-(2-phthalylaminoethyl)piperazine.

To a solution of 660 mg (1.99 mmol) of the amide compound prepared above in 95% aqueous ethanol was added 150 mg (2.40 mmol) of aqueous solution of 80% hydrazine hydrate. The mixture was refluxed for 3.5 hours. After completion of the reaction, the reaction mixture was concentrated under reduced pressure, and dimethylformamide (2 ml) was added to the residue. To the resulting solution was added a solution of 725 mg (1.89 mmol) of N-[3-[3-methoxy-4-(β-methoxyethoxymethoxy)phenyl]propenoyl]-2-thiothiazoline in dimethylformamide (10 ml). The mixture was reacted at room temperature for 12 hours, and then concentrated under reduced pressure to give a residue. The residue was subjected to silica gel column chromatography. There was obtained from a fraction eluted with chloroform 252 mg (0.541 mmol) of N-ethoxycarbonyl-N'-[2-[3-[3-methoxy-4-(β-methoxy-ethoxymethoxy)phenyl]-2-propenoyl]aminoethyl]piperazine.

To a solution 252 mg (0.541 mmol) of the amide compound prepared above in a solution of methanol (2 ml) and water (1 ml) was added 541 mg (9.64 mmol) of potassium hydroxide. the mixture was refluxed for 17 hours. After cooled, water was added to the reaction mixture, and the mixture, was extracted with n-butanol. The organic layer was washed with water and then concentrated under reduced pressure. The residue thus obtained was subjected to Sephadex column chromatography. There was obtained from a fraction eluted with methanol 152 mg (0.386 mmol) of N-[2-[3-[3-methoxy-4-(β-methoxyethoxymethoxy)phenyl]-2-propenoyl]aminoethyl]piperazine.

To a solution of 152 mg (0.386 mmol) of the amide compound prepared above in dry dichlorethane (5 ml) were added in an argon atmosphere 62 mg (0.452 mmol) of anthranilic acid, 94 mg (0.456 mmol) of N,N'-dicyclohexylcarbodiimide and 10 mg (0.082 mmol) of dimethylaminopyridine. The mixture was reacted at room temperature for 17 hours. Precipitates then formed were filtered, and the filtrate was concentrated under reduced pressure. The residue thus obtained was subjected to silica gel column chromatography. There was obtained from a fraction eluted with chloroform-methanol (20:1) 173 mg (0.338 mmol) of N-(o-aminobenzoyl)-N'-[2-[3-[3-methoxy-4-(β-methoxyethoxymethoxy)phenyl]-2-propenoyl]aminoethyl]piperazine.

To a solution of 173 mg (0.338 mmol) of the amide compound prepared above in methanol (3 ml) was added 140 mg (0.736 mmol) of p-toluenesulfonic acid. The mixture was refluxed for 2 hours. After cooled, water was added to the reaction mixture, followed by adjustment of the pH with an aqueous solution of sodium carbonate to 10. The resulting mixture was extracted with ethyl acetate, and the organic layer was concentrated under reduced pressure. The residue thus obtained was subjected to Sephadex column chromatography. There was obtained from a fraction eluted with methanol 98 mg (0.231 mmol) of N-(o-aminobenzoyl)-N'-[2-[3-[3-methoxy-4-hydroxyphenyl)-2-propenoyl]aminoethyl]piperazine. Spectrophotometric data of the product support the structure shown below.

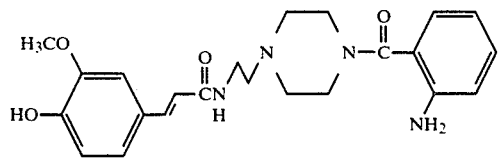

IR$\nu_{max}^{KBr}$ (cm$^{-1}$): 3350, 1660, 1620, 1590.
$^1$H-NMR (deutero methanol) δ:2.53 (6H, m), 3.57 (6H, m), 3.80 (3H, s), 6.40 (1H, d, J=16 Hz), 6.57–7.23 (7H, m), 7.47 (1H, d, J=16 Hz).

EXAMPLE 37

To a solution of 220 mg (0.5 mmol) of N-benzhydryl-N'-(3-phthalylaminopropyl)piperazine in ethanol (5 ml) was added in an argon atmosphere 60 mg (1 mmol) of 80 % aqueous solution of hydrazine hydrate. The mixture was heated under reflux for 2 hours. The reaction solution was concentrated under reduced pressure, and dry dimethylformamide (5 ml) was added to the residue obtained. To the resulting solution was added a solution of 230 mg (0.5 mmol) of N-[3-{3,4-di(β-methoxyethoxymethoxy)phenyl}-2-propenoyl]-2-thiothiazoline in dry dimethylformamide (5 ml). The mixture was reacted at room temperature for 3 hours, followed by removal of the solvent by distillation under reduced pressure. The residue thus obtained was subjected to silica gel column chromatography. There was obtained from a fraction eluted with chloroform - methanol (50:1) 242 mg (0.37 mmol) of N-benzhydryl-N'-[[3-{3,4-di(β-methoxyethoxymethoxy)phenyl}-2-propenoyl]aminopropyl]piperazine.

To a solution of 226 mg (0.35 mmol) of the amide compound prepared above in methanol (5 ml) was added 76 mg (0.4 mmol) of p-toluenesulfonic acid monohydrate. The mixture was heated under reflux for 2 hours. The solvent was removed by concentration under reduced pressure, and water was added to the residue obtained. The mixture was adjusted with an aqueous solution of sodium carbonate to a pH of 10 and then extracted with chloroform. The organic layer was concentrated under reduced pressure, and the residue thus obtained was subjected to Sephadex LH-20 column chromatography. There was obtained from a fraction eluted with methanol 104 mg (0.22 mmol) of N-benzhydryl-N'-[{3-(3,4-dihydroxyphenyl)-2-propenoyl}-aminopropyl]piperazine. Spectrophotometric data of the product support the structure shown below.

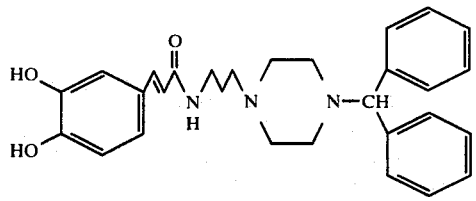

IR$\nu_{max}^{KBr}$ cm$^{-1}$: 3350, 1655, 1610, 1590.

EXAMPLE 38

To a solution of 177 mg (0.403 mmol) of N-benzhydryl-N'-(3-phthalylaminopropyl)piperazine in 95% aqueous solution of ethanol (4.20 ml) was added in an argon atmosphere 26 mg (0.416 mmol) of 80% aqueous solution of hydrazine hydrate. The mixture was refluxed for 3.5 hours. After somption of the reaction, the reaction mixture was concentrated under reduced pressure, and dry dimethylformamide (4 ml) was added to the residue obtained. To the resulting solution was added a solution of 161 mg (0.393 mmol) of N-[5-[3-methoxy-4-(β-methoxyethoxymethoxy)phenyl]-2,4-pentadienoyl]-2-thiothiazoline in dry dimethylformamide (6 ml). The mixture was reacted at room temperature for 3 hours and then concentrated under reduced pressure. The residue thus obtained was subjected to silica gel column chromatography. There was obtained from a fraction eluted with chloroform-methanol (50:1) 155 mg (0.258 mmol) of N-[3-[5-[3-methoxy-4-(β-methoxyethoxymethoxy)phenyl]-2,4-pentadienoyl]-aminopropyl-N'-benzhydrylpiperazine.

To a solution of 155 mg (0.258 mmol) of the amide compound prepared above in methanol (5 ml) was added 80 mg (0.421 mmol) of p-toluenesulfonic acid monohydrate. The mixture was refluxed for 1 hour, and then concentrated under reduced pressure. Water was added to the residue obtained, followed by adjustment of the pH with an aqueous solution of sodium carbonate to 10. The resulting mixture was extracted with ethyl acetate, and the organic layer concentrated under reduced pressure. The residue thus obtained was subjected to silica gel column chromatography. There was obtained from a fraction eluted with chloroform-methanol (50:1) 86 mg (0.168 mmol) of N-[3-[5-(3-methoxy-4-hydroxyphenyl)-2,4-pentadienoyl]aminopropyl]-N'-benzhydrylpiperazine. Spectrophotometric data of the product support the structure shown below.

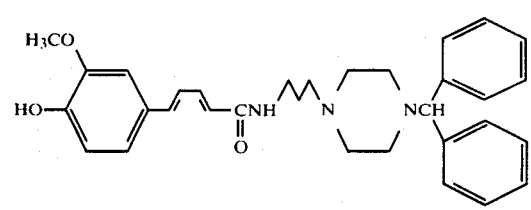

IR$\nu_{max}^{cm-1}$ (KBr): 3300, 1655, 1620, 1595.
$^1$H-NMR (deutero chloroform) δ:1.68 (2H, m), 2.47 (10H, bs), 3.38 (2H, m), 3.85 (3H, s), 4.22 (1H, s), 5.83 (1H, d, J=15 Hz), 6.28–7.67 (m, 16H).

EXAMPLE 39

To a solution of 5.65 g (21.1 mmol) of N-(3-bromopropyl)phthalimide in toluene (50 ml) was added in an argon atmosphere 5.05 g (17.6 mmol) of p-chlorobenzhydrylpiperazine. The mixture was refluxed for 7 hours. Water was added to the reaction solution, followed by adjustment of the pH with an aqueous solution of sodium carbonate to 10. The resulting mixture was extracted with chloroform. The organic layer was concentrated under reduced pressure and then subjected to silica gel column chromatography. There was obtained from a fraction eluted with chloroform 3.44 g (7.26 mmol) of N-(p-chlorobenzhydryl)-N'-(3-phthalylaminopropyl)piperazine.

To a solution of 237 mg (0.5 mmol) of the piperazine derivative prepared above in ethanol (5 ml) was added in an argon atmosphere 60 mg (1 mmol) of 80% aqueous solution of hydrazine hydrate. The mixture was heated under reflux for 2 hours. The reaction solution was concentrated under reduced pressure, and dry dimethylformamide (5 ml) was added to the residue obtained. To the resulting solution was added a solution of 205 mg (0.5 mmol) of N-[5-[3-methoxy-4-(β-methoxyethoxymethoxy)phenyl]-2,4-pentadienoyl]-2,4-pentadienoyl]-2-thiothiazoline in dry dimethylformamide (5 ml). The mixture was reacted at room temperature for 2 hours and then concentrated under reduced pressure. The residue thus obtained was subjected to silica gel column chromatography. There was obtained from a fraction eluted with chloroform-methanol (50:1) 188 mg (0.32 mmol) of N-(p-chlorobenzhydryl)-N'-[3-[5-{3-methoxy-4-(β-methoxyethoxymethoxy)phenyl}-2,4-pentadienoyl]-aminopropyl]piperazine.

To a solution of 176 mg (0.30 mmol) of the amide compound prepared above in methanol (5 ml) was added 80 mg (0.42 mmol) of p-toluenesulfonic acid monohydrate. The mixture was heated under reflux for 1 hour. The reaction solution was concentrated under reduced pressure, and water was added to the residue obtained, followed by adjustment of the pH with an aqueous solution of sodium hydrogen carbonate to 10. The resulting mixture was extracted with ethylacetate, and the organic layer was concentrated under redueced pressure. The residue thus obtained was subjected to Sephadex LH-20 column chromatography. There was obtained from a fraction eluted with methanol 115 mg (0.28 mmol) of N-(p-chlorobenzhydryl)-N'-[3-{5-(3-methoxy-4-hydroxyphenyl)-2,4-pentadienoyl)aminopropyl]piperazine. Spectrophotometric data of the product support the structure shown below.

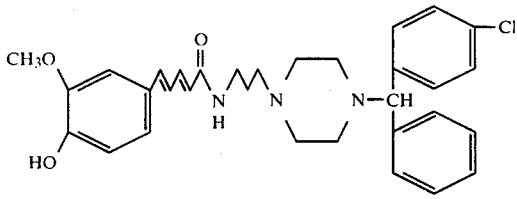

IR$\nu_{max}^{KBr}$ cm$^{-1}$: 3350, 1660, 1615, 1595.

EXAMPLE 40

To 10 ml of toluene were dissolved 0.55 g (5.5 mmol) of methylpiperazine and 1.27 g (5 mmol) of N-(2-bromethyl)phthalimide in an argon atmosphere. The mixture was heated under reflux for 2 hours. To the reaction mixture was added an aqueous solution of sodium carbonate to adjust the pH to 10. The resulting mixture was extracted with ethylacetate, and the organic layer was concentrated under reduced pressure. The residue thus obtained was subjected to silica gel column chromatography. There was obtained from a fraction eluted with chloroform - methanol (19:1) 520 mg (1.9 mmol) of N-methyl-N'-(2-phthalylaminoethyl)piperazine.

To a solution of 136 mg (0.5 mmol) of the above-prepared piperazine derivative which had been dissolved in an argon atmosphere in 5 ml of ethanol was added 60 mg (1 mmol) of 80% hydrazine hydrate. The mixture was heated under reflux for 2 hours. The reaction solution was concentrated under reduced pressure, and 5 ml of tetrahydrofuran was added to the residue obtained. To the resulting solution was added a tetrahydrofuran solution of 205 mg (0.5 mmol) of N-[5-{3-methoxy-4-(β-methoxyethoxymethoxy)phenyl-{2,4-pentadienoyl]-2-thiothiazolidine. The mixture was reacted at room temperature for 1 hour. The reaction solution was concentrated under reduced pressure, and the residue thus obtained was subjected to silica gel column chromatography. There was obtained from a fraction eluted with chloroform - methanol (25:1) 175 mg (0.40 mmol) of N-methyl-N'-[[5-{3-methoxy-4-(βmethoxyethoxymethoxy)phenyl}-2,4-pentadienoyl]-aminoethyl]piperazine.

To a solution of 170 mg (0.39 mmol) of the amide product prepared above in 5 ml of methanol was added in an argon atmosphere 152 mg (0.8 mmol) of p-toluenesulfonic acid monohydrate. The mixture was heated under reflux for 1 hour, and saturated aqueous solution of sodium hydrogen carbonate was added to the reaction solution. The mixture was extracted with n-butanol, and the organic layer was concentrated under reduced pressure. The residue thus obtained was subjected to Sephadex Lh-20 column chromatography. There was obtained from a fraction eluted with methanol 120 mg (0.35 mmol) of N-methyl-N'-[3-}5-(3-methoxy-4-hydroxyphenyl)-2,4-pentadienoyl}aminoethyl]piperazine. Spectrophotometric data of the product support the structure shown below.

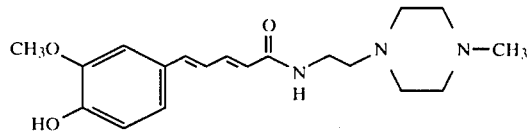

IR$\nu_{max}^{KBr}$ (cm$^{-1}$): 3400, 1650, 1590.

$^1$H-NMR (deutero methanol) δ:2.23 (3H, s), 2.48 (10H, bs), 3.50 (2H, m), 3.82 (3H, s), 5.93 (1H, d, J=14 Hz), 6.47–7.90 (6H, m).

EXAMPLE 41

To a solution of 188 mg (0.508 mmol) of N-[5-(3-methoxy-4-hydroxyphenyl)-2,4-pentadienoyl]-pyridoxamine in dry pyridine (5 ml) was added in an argon atmosphere 0.300 ml (2.27 mmol) of toluoylchloride. The mixture was reacted at room temperature for 28 hours. The reaction solution was concentrated under reduced pressure, and water was added to the residue obtained, followed by adjustment of the pH with an aqueous solution of sodium carbonate to 10. The resulting mixture was extracted with chloroform, and the organic layer was concentrated under reduced pressure and then subjected to silica gel column chromatography. There was obtained from a fraction eluted with chloroform 355 mg (0.49 mmol) of N-[5-(3-methoxy-4-toluoxyphenyl)-2,4-pentadienoyl]-O,O'-ditoluoyl-pyridoxamine.

To a solution of 355 mg (0.49 mmol) of the amide compound prepared above in a solution of tetrahydrofuran (8 ml) and water (2 ml) was added 0.520 ml (5.26 mmol) of piperidine. The mixture was reacted at room temperature for 47 hours, followed by addition of water. The resulting mixture was extracted with ethyl acetate, and the organic layer was concentrated under reduced pressure. There was obtained 109 mg (0.223 mmol) of 4-[5-(3-methoxy-4-hydroxyphenyl)-2,4-pentadienoyl]-aminomethyl-3-hydroxy-2-methyl-5-toluoxymethylpyridine. Spectrophotometric data of the product support the structure shown below.

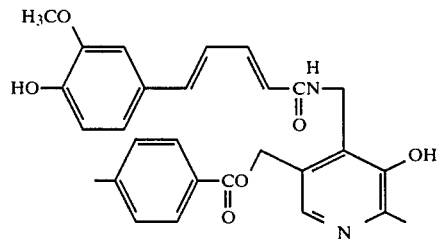

IR$\nu_{max}^{cm-1}$(KBr): 3450, 1730, 1650, 1615, 1590.

$^1$H-NMR (deutero pyridine) δ:2.22 (3H, s), 2.72 (3H, s), 3.72 (3H, s), 4.85 (2H, d, J=6 Hz), 5.58 (2H, s), 6.32 (1H, d, J=14 Hz), 6.87–7.27 (8H, m), 8.02 (2H, d, J=8 Hz), 8.38 (1H, s), 9.90 (1H, t, J=6 Hz).

EXAMPLE 42

To an ethanol solution of 331 mg (1 mmol) of N-ethoxycarbonyl-N'-(2-phthalylaminoethyl)piperazine was added in an argon atmosphere 125 mg (22 mmol) of 80% aqueous solution of hydrazine hydrate. The mixture was heated under reflux for 2 hours. The reaction mixture was concentrated under reduced pressure, and 5 ml of dimethylformamide was added to the residue then obtained. To the resulting solution was added a dimethylformamide solution of 470 mg (1.15 mmol) of N-[5-{3-methoxy-4-(β-methoxyethoxymethoxy)-phenyl}-2,4-pentadienoyl]-2-thiothiazoline. The mixture was reacted at room temperature for 8 hours. The reaction solution was concentrated under reduced pressure, and the residue thus obtained was subjected to silica gel column chromatography. There was obtained from a fraction eluted with chloroform - methanol (50:1) 200 mg (0.41 mmol) of N-ethoxycarbonyl-N'-[[5-{3-methoxy-4-(β-methoxyethoxy)phenyl}-2,4-pentadienoyl]aminoethyl]piperazine.

To a solution of 200 mg (0.41 mmol) of the amide compound prepared above in 5 ml of ethanol were added 2 ml of water and 344 mg (6 mmol) of potassium hydroxide. The mixture was heated in an argon atmosphere under reflux for 21 hours. Water was added to the reaction solution, and the mixture was extracted with n-butanol. The organic layer was concentrated under reduced pres-sure, and the residue thus obtained was subjected to Sephadex LH-20 column chromatography. There was obtained from a fraction eluted with methanol 147 mg (0.35 mmol) of N-[[5-{3-methoxy-4-(β-methoxyethoxy)phenyl-{2,4-pentadienoyl]-aminoethyl]piperazine.

To a solution of 147 mg (0.35 mmol) of the amide compound in dichlorethane (5 ml) were added 55 mg (0.4 mmol) of anthranilic acid, 82 mg (0.4 mmol) of N,N'-dicyclohexyl-carbodiimide and 10 mg (0.08 mmol) of dimethylaminopyridine. The mixture was reacted at room temperature for 17 hours. Precipitates formed were filtered, and the filtrate was concentrated under reduced pressure. The residue thus obtained was subjected to silica gel column chromatography. There was obtained from a fraction eluted with chloroform - methanol (19:1) )179 mg (0.33 mmol) of N-(o-aminobenzoyl)-N'-[[5-{3-methoxy-4-(β-methoxyethoxy)phenyl}-2,4-pentadienoyl]-aminoethyl]piperazine.

To a solution of 157 mg (0.29 mmol) of the amide compound prepared above in methanol (5 ml) was added 120 mg (0.6 mmol) of p-toluenesulfonic acid monohydrate. The mixture was heated under reflux for 1 hour. After completion of the reaction, water was added to the reaction mixture, followed by adjustment of the pH with saturated aqueous solution of sodium hydrogen carbonate to 10. The resulting mixture was extracted with n-butanol. The extract was concentrated under reduced pressure, and the residue thus obtained was subjected to Sephadex LH-20 column chromatography. There was obtained from a fraction eluted with methanol 106 mg (0.24 mmol) of N-(o-aminobenzoyl)-N'-[{5-(3-methoxy-4-hydroxyphenyl)-2,4-pentadienoyl-}aminoethyl]piperazine. Spectrophotometric data of the product support the structure shown below.

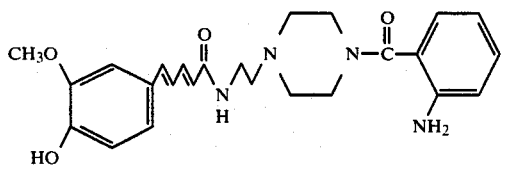

IR $\nu_{max}^{KBr}$(cm$^{-1}$): 3350, 1650, 1620, 1590.

$^1$H-NMR (deutero methanol) δ: 2.50 (6H, m), 3.53 (6H, m), 3.82 (3H, s), 6.00 (1H, d, J=16Hz), 6.42–7.25 (10H, m).

EXAMPLE 43

To a solution of 1.1 g (12.9 mmol) of putrescine in dry tetrahydrofuran (10 ml) was added in an argon atmosphere 500 mg (1.29 mmol) of N-5-[3-methoxy-4-(β-methoxy)ethoxymethoxy]phenyl-2,4-pentadienoyl-2-mercaptothiazoline in dry tetrahydrofuran (10 ml) dropwise slowly. The mixture was stirred at room temperature for 30 min. The reaction solution was concentrated under reduced pressure and then subjected to partition extraction with ethyl acetate and 2N-aqueous solution of sodium hydroxide.

The organic layer was washed with water and saturated saline solution, followed by concentration under reduced pressure. To dry 1,2-dichloromethane (15 ml) were added the residue obtained above, 264.0 mg (1.925 mmol) of anthranilic acid and 23.4 (0.192 mmol) of N,N-dimethylaminopyridine. To the mixture was added in an argon atmosphere 397.1 mg (1.925 mmol) of dicyclohexylcarbodiimide, and the mixture was stirred at room temperature for 13 hours. The reaction solution was filtered, and the filtrate was concentrated under reduced pressure. The residue thus obtained was subjected to silica gel column chromatography. There was obtained from a fraction eluted with chloroform - methanol (30 : 1) 414.0 mg (0.83 mmol) of N-5-[3-methoxy-4-(β-methoxy) ethoxymethoxy]phenyl-2,4-pentadienoyl-N'-(2-amino)benzoyl putrescine. Then, the putrescine derivative was dissolved in methanol (15 ml), and 237.4 mg (1.25 mmol) of paratoluenesulfonic acid was added to the solution. The resulting mixture was heated in an argon atmosphere under reflux for 5 hours. The reaction solution was concentrated under reduced pressure and subjected to partition extraction with ethyl acetate and saturated aqueous solution of sodium hydrogen carbonate. The organic layer was washed with water and saturated saline solution and then concentrated under reduced pressure. The residue thus obtained was subjected to Sephadex column chromatography. Use of methanol as the eluting agent yielded 236.2 mg (0.577 mmol) of N-5-(3-methoxy-4-hydroxy)phenyl-2,4-pentadienoyl-N'-(2-amino)-benzoyl putrescine. Spectrophotometric data of the product support the structure shown below.

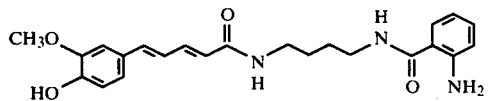

IR $\nu_{max}^{cm-1}$(KBr): 3350, 1645, 1615, 1585, 1515.

$^1$H-NMR((CD$_3$)$_2$CO) δppm: 1.67 (4H, m), 3.03–3.73 (4H, m), 3.83 (3H, s), 6.12 (1H, d (J=14Hz)), 6.16 (2H, m), 6.33–7.83 (12H, m).

EXAMPLE 44

To a solution of 200 mg (0.45 mmol) of N-benzhydryl-N'-(3-phthalylaminopropyl)piperazine in 5 ml of ethanol was added 70 mg (1.4 mmol) of 80% hydrazine hydrate. The mixture was heated in an argon atmosphere under reflux for 2 hours. The reaction solution was concentrate under reduced pressure, and 5 ml of tetrahydrofuran was added to the residue obtained. To the resulting solution was added a tetrahydrofuran solution of 400 mg (0.83 mmol) of N-[5-{3,4-di(β-methoxyethoxymethoxy)phenyl}-2,4-pentadienoyl]-2-thiothiazoline. The mixture was reacted at room temperature for 12 hours. The reaction solution was concentrated under reduced pressure, and the residue thus obtained was subjected to silica gel column chromatography. There was obtained from a fraction eluted with chloroform - methanol (50:1) 222 mg (0.33 mmol) of N-benzhydryl-N'-[[5-{3,4-di(β-methoxyethoxymethoxy)phenyl}-2,4-pentadienoyl]aminopropyl]piperazine.

To a solution of 222 mg (0.33 mmol) of the amide compound prepared above in 10 ml of methanol was added 125 mg (0.66 mmol) of p-toluenesulfonic acid monohydrate. The mixture was heated under reflux for 2 hours. Water was added to the reaction solution, followed by addition of saturated aqueous solution of sodium hydrogen carbonate to adjust the pH to 10. The resulting mixture was extracted with n-butanol. The organic layer was concentrated under reduced pressure, and the residue thus obtained was subjected to Sephadex LH-20 columnchromatography. There was obtained from a fraction eluted with methanol 126 mg (0.25 mmol) of N-benzhydryl-N'-[[5-{3,4-dihydroxyphenyl)-2,4-pentadienoyl}aminopropyl]piperazine. Spetrophotometric data of the product support the structure shown below.

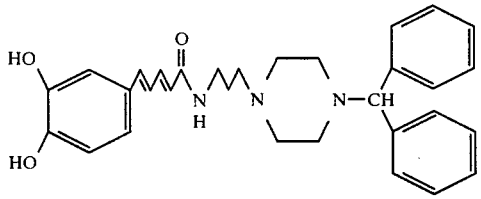

IR $\nu_{max}^{KBr}$(cm$^{-1}$): 3300, 1650, 1590.

$^1$H-NMR (deutro acetone) δ: 1.68 (2H, m), 2.42 (10H, bs), 3.33 (2H, m), 4.22 (1H, s), 6.03 (1H, d, J=15Hz), 6.20–7.60 (16H, m).

EXAMPLE 45

To a solution of 237 mg (0.5 mmol) of N-(p-chlorobenzhydryl)-N'-(3-phthalylaminopropyl)- piperazine in ethanol (5 ml) was added in an argon atmosphere 60 mg (1 mmol) of 80% aqueous solution of hydrazine hydrate. The mixture was heated under reflux for 2 hours. The reaction solution was concentrated under reduced pressure, and dry dimethylformamide (5 ml) was added to the residue then obtained. To the resulting solution was added a solution of 242 mg (0.5 mmol) of N-[5-{3,4-di(β-methoxyethoxymethoxy)-phenyl}2,4-pentadienoyl]-2-thiothiazoline in dry dimethylformamide (5 ml). The mixture was reacted at room temperature and then concentrated under reduced pressure. The residue thus obtained was subjected to silica gel column chromatography. There was obtained a fraction eluted with chloroform - methanol (50 : 1) 194 mg (0.29 mmol) of N-p-chlorobenzhydryl)-N'-[[5-{3,4-di(β-methoxyethoxymehtoxy)-phenyl}-2,4-pentadienoyl]-aminopropyl]piperazine.

To a solution of 165 mg (0.25 mmol) of the amide compound in methanol (5 ml) was added 57 mg (0.3 mmol) of p-toluenesulfonic acid monohydrate. The mixture was heated under reflux for 1 hour. The solvent was removed by distillation under reduced pressure, and water was added to the residue obtained, followed by adjustment of the pH with an aqueous solution of sodium hydrogen carbonate. The resulting mixture was extracted with ethyl acetate. The organic layer was concentrated under reduced pressure, and the residue thus obtained was subjected to Sephadex LH-20 column chromatography. There was obtained from a fraction eluted with methanol 82 mg (0.17 mmol) of N-(p-chlorobenzhydryl)-N'-[{5-(3,4-dihydroxyphenyl)-2,4-pentadienoyl}-aminopropyl]piperazine. Spectrophotometric data of the product support the structure shown below.

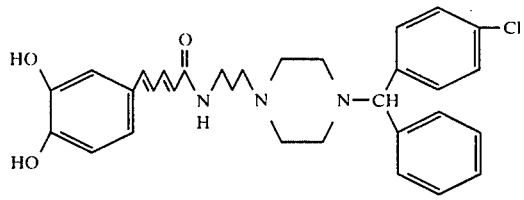

IR $\nu_{max}^{KBr}$(cm$^{-1}$): 3500, 1665, 1620, 1600.

EXAMPLE 46

To a solution of 178 mg (0.50 mmol) of N-{5-(3,4-dihydroxyphenyl)-2,4-pentadienoyl}pyridoxamine in dry pyridine (5 ml) was added under an argon atmosphere 0.30 (2.27 mmol) of toluoyl chloride. The mixture was reacted at room temperature for 24 hours. The reaction solution was concentrated under reduce pressure, and water was added to the residue obtained, followed by adjustment of the pH with an aqueous solution of sodium hydrogen carbonate to 10. The resulting mixture was extracted with chloroform, and the organic layer was concentrated under reduced pressure. The residue thus obtained was subjected to silica gel column chromatography. There was obtained from a fraction eluted with chloroform 397 mg (0.48 mmol) of N-{5-(3,4-ditoluoxyphenyl)-2,4-pentadienoyl}-0,0'-ditoluoylpyridoxamine.

To a solution of 397 mg (0.48 mmol) of the amide compound prepared above in tetrahydrofuran (8 ml) and water (2 ml) was added 0.52 (5.26 ml) of piperidine. The mixture was reacted at room temperature for 48 hours, followed by addition of water and then extraction with ethyl acetate. The organic layer was concentrated under reduced pressure to give 104 mg (0.22 mmol) of 4-{5-3,4-dihydroxyphenyl)-2,4-pentadienoyl-}aminomethyl-3-hydroxy-2-methyl-5-toluoxymethyl-pyridine. Spectrophotometric data of the product support the structure shown below.

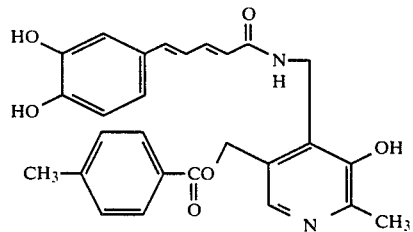

IR $\nu_{max}^{KBr}$(cm$^{-1}$): 3500, 1735, 1660, 1615, 1590.

EXAMPLE 47

To a solution of 194 mg (0.441 mmol) of N-[3-(4-benzhydryl-1-piperazinyl)propyl]phthalimide in 95% aqueous ethanol (5 ml) was added in an argon atmosphere 55 mg (1.10 mmol) of 80% aqueous solution of hydrazine hydrate. The mixture was refluxed for 3 hours. After completion of the reaction, concentration under reduced pressure produced a residue, to which was then added 5 ml of dry dimethylformamide. To the resulting solution was added a solution of 140 mg (0.417 mmol) of N-[5-(3,4-dimethoxyphenyl)-2,4-pentadienoyl]-2-thiothiazoline. The mixture was reacted at room temperature and then concentrated under reduced pressure. The residue thus obtained was subjected to silica gel column chromatography. There was obtained from a fraction eluted with chloroform - methanol (50 : 1) 103 mg (0.196 mmol) of N-[3-[5-(3,4-dimethoxyphenyl)-2,4-pentadienoyl]-aminopropyl]-N'-benzhydrylpiperazine. Spectrophotometric data of the product support the structure shown below.

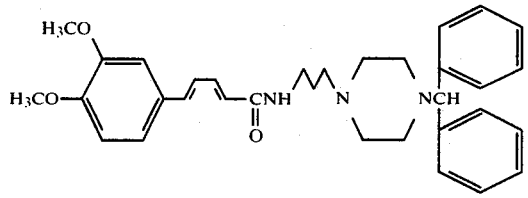

IR $\nu_{max}^{cm-1}$(KBr): 3400, 1650, 1610, 1595.

1H-NMR (deutero chloroform) δ: 1.70 (2H, m), 2.47 (10H, bs), 3.40 (2H, m), 3.87 (3H, s), 3.90 (3H, s), 4.23 (1H, s), 5.83 (1H, d, J=14Hz), 6.63-7.53 (16H, m).

EXAMPLE 48

To an ethanol solution of 331 mg (1 mmol) of N-ethoxycarbonyl-N'-(2-phthalylaminoethyl)piperazine was added in an argon atmosphere 125 mg (1 mmol) of 80 % aqueous solution of hydrazine hydrate. The mixture was heated under reflux for 2 hours. The reaction solution was concentrated under reduced pressure, and 5 ml of dimethylformamide was added to the residue obtained. To the resulting solution was added a solution of 335 mg (1 mmol) of N-{5-(3,4-dimethoxyphenyl)-2,4-pentadienoyl}-2-thiothiazoline in dimethylformamide (5 ml). The mixture was reacted at room temperature for 4 hours. The reaction solution was concentrated under reduced pressure, and the residue thus obtained was subjected to silica gel column chromatography. There was obtained from a fraction eluted with chloroform - methanol (50 : 1) 238 mg (0.57 mmol) of N-ethoxycarbonyl-N'-[5-(3,4-dimethoxyphenyl)-2,4-pentadienoyl]aminoethyl]piperidine.

To a solution of 209 mg (0.50 mmol) of the amide compound prepared above in 5 ml of ethanol were added 2 ml of water and 344 mg (6 mmol) of potassium hydroxide. The mixture was heated in an argon atmosphere under reflux for 23 hours. Water was added to the reaction solution, and the mixture was extracted with n-butanol. The organic layer was concentrated under reduced pressure, and the residue thus obtained was subjected to Sephadex LH-20 column chromatography. There was obtained a fraction eluted with methanol 145 mg (0.42 mmol) of N-[{5-(3,4-dimethoxyphenyl)-2,4-pentadienoyl}aminoethyl]-piperazine.

To a solution of 138 mg (0.40 mmol) of the amide compound prepared above in dichlorethane (5 ml) were added in an argon atmosphere 55 mg (0.40 mmol) of anthranilic acid, 82 mg (0.40 mmol) of N,N'-dicyclohexylcarbodiimide and 10 mg (0.08 mmol) of dimethylaminopyridine. The mixture was reacted at room temperature for 17 hours. Precipitates then formed were filtered, and the filtrate was concentrated under reduced pressure and then subjected to silica gel column chromatography. There was obtained from a fraction eluted with chloroform - methanol (19 : 1) 176 mg (0.38 mmol) of N-(o-aminobenzoyl)-N'-[{5-(3,4-dimethoxyphenyl)-2,4-pentadienoyl}aminoethyl]piperazine. Spectrophotometric data of the product support the structure shown below.

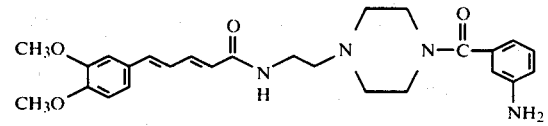

IR $\nu_{max}^{KBr}$(cm$^{-1}$): 1660, 1620, 1590.

EXAMPLE 49

In an argon atmosphere, 3.00 g (13.4 mmol) of 3,5-dimethoxy-4-hydroxycinnamic acid was suspended in a sulfuric acid - ethanol (1 : 115, 50 ml) solution. The suspension was refluxed for 5.5 hours. Water was added to the reaction solution, and the mixture was extracted with methylene chloride. The organic layer was washed with an aqueous solution of sodium hydrogen carbonate and concentrated under reduced pressure to give 3.34 g (13.24 mmol) of ethyl 3,5-dimethoxy-4-hydroxycinnamate.

To a solution of 2.00 g (7.9 mmol) of the ester prepared above in dry dichlorethane (60 ml) were added in an argon atmosphere 1.82 ml (15.9 mmol) of β-methoxyethoxymethyl chloride and 27.7 ml (15.9 mmol) of diisopropylethylamine. The mixture was refluxed for 1.5 hours. Water was added to the reaction solution, and the mixture was extracted with chloroform. The organic layer was concentrated under reduced pressure, and the residue thus obtained was subjected to silica gel column chromatography. There was obtained from a fraction eluted with chloroform 2.60 g (7.6 mmol) of ethyl 3,5-dimethoxy-4-(β-methoxyethoxymethoxy)cinnamate.

To 2.6 g (7.6 mmol) of the ester prepared above in water - methanol (1 : 4, 40 ml) was added 3.04 g (76 mmol) of sodium hydroxide. The mixture was reacted at room temperature for 1.5 hours. Water was added to the reaction solution, and the mixture was adjusted with 6N hydrochloric acid to a pH of 3. The resulting mixture was extracted with cheloroform, and the organic layer was concentrated under reduced pressure to give 2.148 g (6.9 mmol) of 3,5-dimethoxy-4-(β-methoxyethoxymethoxy)cinnamic acid.

To a solution of 2.015 g (6.45 mmol) of the acid compound prepared above in dry dichlorethane (65 ml) were added in an argon atmosphere 846 mg (7.10 mmol) of 2-mercaptothiazoline and 0.08 g (0.65 mmol) of 4-dimethylaminopyridine. The mixture was reacted at room temperature for 12.5 hours. The reaction mixture was filtered, and the filtrate was concentrated under reduced pressure. Water was added to the residue obtained, and the mixture was extracted with methylene chloride. The organic layer was washed with 1N-aqueous solution of sodium hydroxide and water and then concentrated under reduced pressure. The residue thus obtained was subjected to silica gel column chromatography to give 2.50 g (6.05 mmol) of N-[3-[3,5-dimethoxy-4-(β-methoxyethoxymethoxy)phenyl]-propenoyl]-2-thiothiazoline.

Separately, 5.73 g (20 mmol) of p-chlorobenzhydrylpiperazine and 4.57 g (18 mmol) of N-(2-bromethyl)phthalimide were dissolved in 50 ml of benzene in an argon atmosphere. The solution was heated under reflux for 15 hours. The reaction solution was concentrated under reduced pressure, and the residue thus obtained was subjected to silica gel column chromatography. Separatation was made with a mixed solvent of chloroform - methanol ((100 : 1) and recrystallization from ethanol yielded 3.80 g (8.26 mmol) of N-(p-chlorobenzhydryl)-N'-(2-phthalylaminoethyl)piperazine.

To a solution of 103 mg (0.22 mmol) of the piperazine derivative prepared above in ethanol (4 ml) was added 29 mg (0.46 mmol) of 80% aqueous solution of hydrazine hydrate. The mixture was refluxed for 2 hours. The reaction solution was concentrated under reduced pressure, and 3 ml of dry dimethylformamide was added to the residue obtained. To the solution was added a solution of 109 mg (0.26 mmol) of the N-[3-[2,3,5-dimethoxy-4-($\beta$-methoxyethoxymethoxy)phenyl]-propenoyl]-2-thiothiazoline. The mixture was reacted for 13.5 hours, and then the solvent was removed by distillation under reduced pressure. Chloroform was added to the residue obtained, insolubles were filtered, and the filtrate was concentrated under reduced pressure. The residue thus obtained was subjected to silica gel column chromatography. There was obtained from a fraction eluted with ethyl acetate 33 mg (0.05 mmol) of N-[2-[3-[3,5-dimethoxy-4-($\beta$-methoxyethoxymethoxy)phenyl]-2-propenoyl]aminoethyl-N'-p-chlorobenzhydrylpiperazine.

To a solution of 33 mg (0.05 mmol) of the amide compound prepared above in methanol (4 ml) was added 20 mg (0.11 mmol) of p-toluenesulfonic acid monohydrate. The mixture was refluxed for 6.5 hours. The reaction solution was concentrated under reduced pressure, and water was added to the residue obtained. The mixture was extracted with chloroform, and the organic layer was concentrated under reduced pressure. The residue thus obtained was subjected to Sephadex column chromatography. There was obtained from a fraction eluted with methanol 14 mg (0.03 mmol) of N-[2-[3-(3,5-dimethoxy-4-hydroxyphenyl)-2-propenoyl]aminoethyl-N'-p-chlorobenzhydrylpiperazine. Spectrophotometric data of the product support the structure shown below.

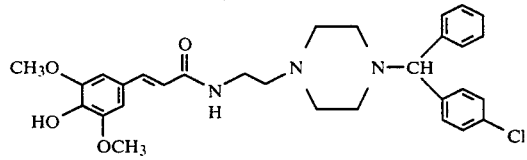

IR $\nu_{max}^{CHCl_3}$cm$^{-1}$: 3530, 1665, 1620.

1H-NMR (deutero chloroform) $\beta$: 2.43 (10H, brs), 3.83 (6H, s), 4.18 (1H, s), 6.10 (1H, d, J=15Hz), 6.63 (2H, s), 7.10–7.65.

EXAMPLE 50

In an argon atmosphere, 176 mg (0.68 mmol) of pyridoxamine dihydrochloride was suspended in 3 ml of dimethylformamide. To the suspension was added 0.5 ml (3.59 mmol) of triethylamine. The mixture was stirred at room temperature for 3.2 hours, followed by addition of a solution of 1409 mg (0.34 mmol) of N-[3-[3,5-dimethoxy-4-($\beta$-methoxyethoxymethoxy)phenyl]-2-propenoyl]-2-thiothiazoline in dry dimethylformamide (3 ml). The mixture was reacted at room temperature for 12.5 hours, and then the solvent was removed by distillation under reduced pressure. Chloroform was added to the residue obtained, insolubles were filtered, and the filtrate was concentrated under reduced pressure. The residue thus obtained was subjected to silica gel column chromatography. There was obtained from fractions eluted with chloroform - methanol (20 : 1–10 : 1) 96 mg (0.21 mmol) of 4-[3-[3,5-dimethoxy-4-($\beta$-methoxyethoxymethoxy)phenyl]-2-propenoyl]aminomethyl-3-hydroxy-5-hydroxymethyl-2-methylpyridine.

To a solution of 96 mg (0.21 mmol) of the amide compound prepared above was added 40 mg (0.21 mmol) of p-toluenesulfonic acid monohydrate. The mixture was refluxed for 5 hours. The reaction solution was concentrated under reduced pressure, and water was added to the residue obtained, followed by adjustment of the pH with an aqueous solution of sodium carbonate. Crystals then precipitated are isolated by filtration. There were obtained 170 mg (0.188 mmol) of 4-[3-(3,5-dimethoxy-4-hydroxyphenyl)-2-propenoyl]aminomethyl-3-hydroxy-5-hydroxymethyl-2-methylpyridine. Spectrophotometric data of the product support the structure shown below.

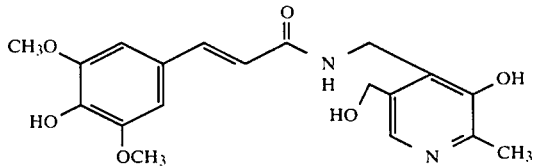

IR $\nu_{max}^{KBr}$(cm$^{-1}$): 3420, 1650, 1605.

1H-NMR (pyridine - d$_5$) $\delta$: 2.67 (3H, s), 3.67 (6H, s), 4.67–5.00 (4H), 6.63 (1H, d, J=15Hz), 6.68 (2H, s), 6.80 (1H, d,J=15Hz), 8.17 (1H, s).

EXAMPLE 51

To a solution of 1.142 g (3.66 mmol) of 3,5-dimethoxy-4-($\beta$-methoxyethoxymethoxy)cinnamic acid in dry acetonitrile (40 ml) were added in an argon atmosphere 1.2 (4.70 mmol) of 2-chloro-1-methylpyridinium iodide, 1.8 ml (12.9 mmol) of triethylamine and 620 $\mu$l (4.79 mmol) of methyl anthranilate. The mixture was refluxed for 43 hours. Water was added to the reaction solution, and the mixture was extracted with ethyl acetate. The organic layer was concentrated under reduced pressure, and the residue thus obtained was subjected to silica gel column chromatography. There was obtained from a fraction eluted with benzene - ethyl acetate (10 : 1) 1.146 g (2.58 mmol) of methyl N-[3,3,5-dimethoxy-4-($\beta$-methoxyethoxymethoxy)phenyl]propenoylanthranilate.

To a suspension of 1.122 g (2.52 mmol) of the amide compound prepared above in methanol (10 ml) was added a solution of 1.0 g (25 mmol) of sodium hydroxide in water - methanol (1 : 5, 20 ml). The mixture was reacted at room temperature for 2 hours. The reaction solution was adjusted with 1N-hydrochloric acid to a pH of 3, and crystals then precipitated were isolated by filtration. There was obtained 947 mg (2.20 mmol) of N-[3-[3,5-dimethoxy-4-($\beta$-methoxyethoxymethoxy)-phenyl]propenoylanthanilic acid.

To a solution of 893 mg (2.07 the amide compound prepared above in 1,4-dioxane (4 ml) was added 80% aqueous acetic acid (16 ml). The mixture was refluxed for 2 hours. Water was added to the reaction solution. Crystals then precipitated were isolated by filtration and recrystallized from methanol. There was obtained 176 mg (0.51 mmol) of N-[3-(3,5-dimethox-4-hydroxyphenyl)propenoyl]anthranilic acid. Spectrophotometric data of the product support the structure shown below.

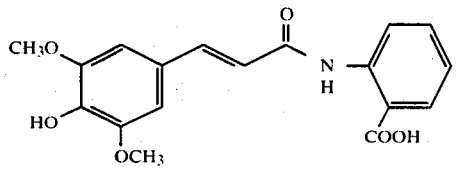

IR $\nu_{max}^{KBr}$(cm$^{-1}$): 3540, 1670, 1610, 1590.
$^1$H-NMR (pyridine - d$_5$) δ: 3.7 (6H, s), 6.83–8.67 (8H, m), 9.27–9.50 (5H, m).

EXAMPLE 52

To a solution of 5.07 g (20.1 mmol) of benzhydrylpiperazine in benzene (50 ml) was added in an argon atmosphere 5.11 g (20.1 mmol) of N-(2-bromethyl)phthalimide. The mixture was refluxed for 23.5 hours. Water was added to the reaction solution, and the mixture was adjusted with sodium carbonate to a pH of 10. The resulting mixture was extracted with ethyl acetate, and the organic layer was concentrated under reduced pressure and subjected to silica gel column chromatography. There was obtained from a fraction eluted with benzene - ethyl acetate (9 : 1) 3.4 g of N-benzhydryl-N'-(2-phthalylaminoethyl)piperazine.

To a solution of 100 mg (0.34 mmol) of the N-benzhydryl-N'-2-phthalylaminoethylpiperazine in 95% aqueous ethanol (2.2 ml) was added 34 mg (0.68 mmol) of of 80% aqueous solution of hydrazine hydrate. The mixture was heated under reflux for 2 hours. After completion of the reaction, concentration under reduced pressure yielded a residue, to which dry dimethylformamide (10 ml) was added.

Separately, to a solution of 103.9 mg (0.44 mmol) of 3,4,5-trimethoxycinnamic acid in 1,2-dichloethane (4 ml) were added in an argon atmosphere 58.4 (0.49 mmol) of 2-mercaptothiazoline, 101.1 mg (0.49 mmol) of dicyclohexylcarbodiimide and 4.9 mg (0.04 mmol) of N,N-dimethylaminopyridine. The mixture was stirred at room temperature for 2 hours. The reaction mixture was filtered, and the filtrate was concentrated and then extracted with methylene chloride and 1N-aqueous solution of sodium hydroxide. The organic layer was concentrated under reduced pressure, and the residue thus obtained was subjected to silica gel column chromatography. There was obtained from a fraction eluted with chloroform 137.9 (0.41 mmol) of N-3-(3',4',5'-trimethoxy)phenyl-2-propenoyl-2-mercaptothiazoline.
A solution of the above product in dry dimethylformamide (2.5 ml) was added to a solution of the above-prepared residue in dry dimethylformamide (10 ml), and the mixture was stirred in an argon atmosphere at room temperature for 18 hours. The reaction solution was concentrated under reduced pressure, and the residue thus obtained was subjected to silica gel column chromatography. There was obtained from a fraction eluted with chloroform - methanol (50 : 1) 102.8 mg (0.20 mmol) of N-benzhydryl-N'-[3-(3',4',5'-trimethoxy)phenyl-2-propenoyl]aminoethylpiperazine. Spectrophotometric data of the product support the structure shown below.

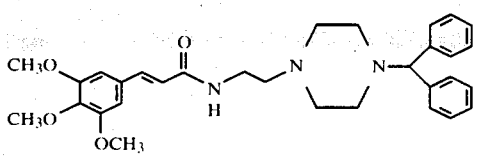

IR $\nu_{max}^{cm-1}$(CHCL$_3$): 3400, 1665, 1625, 1585, 1505.
$^1$H-NMR (deutero chloroform) δ(ppm): 2.43 (10H, m), 3.20–3.70 (3H, m), 3.80 (9H, s), 4.20 (1H, s), 6.23 (1H, d (J=16Hz), 6.60 (2H, s), 6.96–7.63 (13H, m).

EXAMPLE 53

To a solution of 10.01 g (55 mmol) of 3,5-dimethoxy-4-hydroxybenzaldehyde in dry methylene chloride (100 ml) cooled with ice were added in an argon atmosphere 12.4 ml (71 mmol) of β-methoxyethoxymethyl chloride and 12.4 12.4 ml (71 mmol) of diisopropylamine. The mixture was reacted at room temperature for 14.5 hours. The reaction solution was diluted with methylene chloride, and then the organic layer was concentrated under reduced pressure. The residue thus obtained was subjected to silica gel column chromatography. There was obtained from fractions eluted with benzene - ethyl acetate (9:1–2:1) 14.5 g (53.7 mmol) of 3,5-dimethoxy-4-(β-methoxyethoxymethoxy)benzaldehyde.

To a solution of 210 mg (5.25 mmol) of mineral oil containing 60% sodium hydride in dry tetrahydrofuran (20 ml) was added 1.3 ml (5.86 mmol) of triethyl 4-phosphonocrotonate. The mixture was reacted at 0° C. for 1 hour, followed by addition of a solution of 1.01 g (3.74 mmol) of the 3,5-dimethoxy-4-(β-methoxyethoxymethoxy)benzaldehyde in dry tetrahydrofuran (4 ml). The resulting mixture was reacted at room temperature for 2 hours. Saturated aqueous solution of ammonium chloride was added to the reaction solution, and the mixture was extracted with chloroform. The organic layer was concentrated under reduced pressure, and the residue was subjected to silica gel column chromatography. There was obtained from fractions eluted with benzene - ethyl acetate (5:1–2:1) 910 mg (2.49 mmol) of ethyl 5-[3,5-dimethoxy-4-(β-methoxyethoxymethoxy)-phenyl]-2,4-pentadienoate.

To a solution of 880 mg (2.40 mmol) of the ester compound prepared above in methanol (10 ml) was added in an argon atmosphere a solution of 962 mg (24.1 mmol) of sodium hydroxide in water - methanol (1 : 4, 40 ml). The mixture was reacted at room temperature for 23.5 hours. Water was added to the reaction solution, and the mixture was adjusted with 1N-hydrochloric acid to a pH of 3.5. The resulting mixture was extracted with chloroform, and the organic layer was concentrated under reduced pressure. There was obtained 790 mg (2.34 mmol) of 5-[3,5-dimethoxy-4-(β-methoxyethoxymethoxy)phenyl]-2,4-pentadienic acid.

To a solution of 890 mg (2.63 mmol) of the acid compound prepared above in dry dichlorethane (30 ml) were added in an argon atmosphere 345 mg (2.90 mmol) of 2-mercaptothiazoline, 32 mg (0.26 mmol) of dimethylaminopyridine and 596 mg (2.89 mmol) of N,N'-dicyclohexylcarbodiimide. The mixture was reacted at room temperature for 1.5 hours. The reaction solution was filtered, and the filtrate was concentrated under reduced pressure. The residue thus obtained was subjected to silica gel column chromatography. There was obtained from fractions eluted with methylene chloride - ethyl acetate (9 : 1) 1.056 g (2.4 mmol) of N-[5-[3,5-dimethoxy -4-(β-methoxyethoxymethoxy)phenyl]-2,4-pentadienoyl]-2-thiothiazoline.

To a solution of 120 mg (0.28 mmol) of N-(p-chlorobenzhydryl)-N'-(2-phthalylaminoethyl)piperazine in aqueous ethanol (4 ml) was added in an argon atmosphere 35 mg (0.56 mmol) of 80% aqueous solution of hydrozine hydrate. The mixture was refluxed for 2.5 hours. After completion of the reaction, the solvent was removed by distillation under reduced pressure, and dry dimethylformamide (4 ml) was added to the residue obtained. To the resulting solution was added a solution of 147 mg (0.33 mmol) of the N-[5-(3,5-dimethoxy-4-(β-methoxyethoxymethoxy)phenyl]-2,4-pentadienoyl]-2-thiothiazoline in dry dimethylformamide (4 ml). The mixture was reacted at room temperature for 4.2 hours. Then, the solvent was removed by distillation under reduced pressure, and chloroform was added to the residue obtained. Insolubles were filtered, and the filtrate was concentrated under reduced pressure. The residue thus obtained as subjected to silica gel column chromatography. There was obtained from fractions eluted with methylene chloride - ethyl acetate (10:1–1:1) 113 mg (0.18 mmol) of N-[2-[5-[3,5-dimethoxy-4-(β-methoxyethoxymethoxy)phenyl]-2,4-pentadienoyl]aminoethyl]-N'-benzhydrylpiperazine.

To a solution of 110 mg (0.18 mmol) of the amide compound above in methanol (8 ml) was added 34 mg (0.18 mmol) of p-toluenesulfonic acid monohydrate. The mixture was refluxed for 5.6 hours. The reaction solution was concentrated under reduced pressure, and water was added to the residue obtained, followed by adjustment of the pH with an aqueous solution of sodium carbonate to 9. The resulting mixture was extracted with chloroform, and the organic layer was concentrated under reduced pressure. There was obtained 90 mg (0.16 mmol) of N-[2-[5-(3,5-dimethoxy-4-hydroxyphenyl)-2,4-pentadienoyl]aminoethyl]-N'-benzhydrylpiperazine. Spectrophotometric data of the product support the structure shown below.

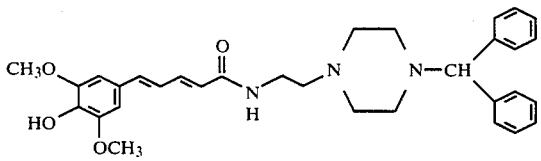

IR $\mu_{max}^{KBr}$(cm$^{-1}$): 3400, 1650, 1580.

$^1$H-NMR (methanol d$_4$) δ: 2.47 (10H, br, s), 3.77 (6H, s), 4.17 (1H, s), 6.02 (1H, d, J=14Hz), 6.60–7.60 (15H, m), 7.80 (1H, s).

EXAMPLE 54

To a solution of 206 mg (0.44 mmol) of N-(p-chlorobenzhydryl)-N-'-(2-phthalylaminoethyl)piperazine in ethanol (4 ml) was added in an argon atmosphere 60 mg (0.92 mmol) of 80% aqueous solution of hydrazine hydrate. The mixture was refluxed for 2 hours. The reaction solution was concentrated under reduced pressure, and 5 ml of dry dimethylformamide was added to the residue obtained. To the resulting solution was added to a solution of 220 mg (0.5 mmol) of N-[5-{3,5-dimethoxy-4-(β-methoxyethoxymethoxy)phenyl}-2,4-pentadienoyl]-2-thiothiazoline in dry dimethylformamide (4 ml). The mixture was reacted at room temperature for 2 hours. Then, the solvent was removed by distillation under reduced pressure, and the residue thus obtained was subjected to silica gel column chromatography. There was obtained from fractions eluted with chloroform - methanol (50:1) 185 mg (0.31 mmol) of N-(p-chlorobenzhydryl)-N'-[2-[5-{3,5-dimethoxy-4-(β-methoxyethoxymethoxy)phenyl]-2,4-pentadienoyl}aminoethyl]piperazine.

To a solution of 150 mg (0.25 mmol) of the amide compound prepared above in methanol (10 ml) was added 52 mg (0.27 mmol) of p-toluenesulfonic acid monohydrate. The mixture was heated under reflux for 2 hours. The reaction solution was concentrated under reduced pressure, and water was added to the residue obtained, followed by adjustment of the pH with an aqueous solution of sodium carbonate. The resulting mixture was extracted with chloroform, and the organic layer was concentrated under reduced pressure. There was obtained 118 mg (0.23 mmol) of N-(p-chlorobenzhydryl)-N'-[2-{5-(3,5-dimethoxy-4-hydroxyphenyl)-2,4-pentadienoyl}aminoethyl]piperazine. Spectrophotometric data of the product support the structure shown below.

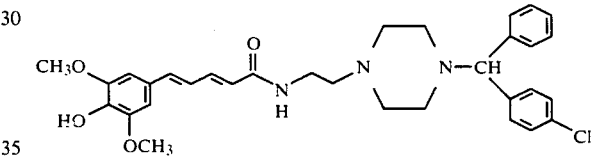

IR $\nu_{max}^{KBr}$(cm$^{-1}$): 3400, 1660, 1620.

EXAMPLE 55

To a solution of 220 mg (0.5 mmol) of N-(benzhydryl)-N'-(3-phthalylaminopropyl)piperazine in ethanol (5 ml) was added in an argon atmosphere 60 mg (1 mmol) of 80% aqueous solution of hydrazine hydrate. The mixture was heated under reflux for 2 hours. The reaction solution was concentrated under reduced pressure, and dry dimethylformamide (5 ml) was added to the residue obtained. To the resulting solution was added a solution of 220 mg (0.5 mmol) of N-[5-{3,5-dimethoxy-4-(β-methoxyethoxymethoxy)phenyl}-2,4-pentadienoyl]-2-thiothiazoline in dry dimethylformamide (4 ml). The mixture was reacted at room temperature for 2 hours. Then, the solvent was concentrated under reduced pressure, and the residue thus obtained was subjected to silica gel column chromatography. There was obtained from a fractions eluted with chloroform - methanol (50 : 1) 204 mg (0.35 mmol) of N-(benzhydryl)-N'-[3-[5-{3,5-dimethoxy-4-(β-methoxyethoxymethoxy)phenyl}-2,4-pentadienoyl]aminopropyl]piperazine.

To a solution of 204 (0.35 mmol) of the amide compound prepared above in methanol (10 ml) was added 76 mg (0.4 mmol) of p-toluenesulfonic acid monohydrate. The mixture was heated under reflux for 2 hours. The reaction solution was concentrated under reduced pressure, water was added to the residue obtained, followed by adjustment of the pH with an aqueous solution of sodium carbonate to 9. The resulting mixture was extracted with chloroform, and the organic layer was concentrated under reduced pressure. There was obtained 173 mg (0.35 mmol) of N-(benzhydryl)-N'-[2-{5-dimethoxy4-hydroxyphenyl)-2,4-pentadienoyl-}aminopropyl]piperazine. Spectrophotometric data of the product support the structure shown below.

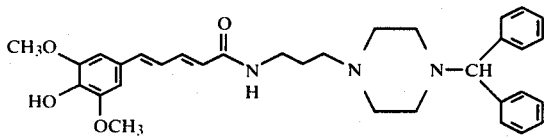

IR $\nu_{max}$KBr (cm$^{-1}$): 3350, 1660, 1615.

EXAMPLE 56

In 3 ml of dry dimethylformamide was suspended in an argon atmosphere 356 mg (1.37 mmol) of pyridoxamine dihydrochloride, and 1.0 m (7.18 mmol) of triethylamine was added to the suspension. The mixture was stirred for 4.5 hours, followed by addition of a solution of 297 mg (0.68 mmol) of N-[5-(3,5-dimethoxy-4-($\beta$-methoxyethoxymethoxy)phenyl]-2,4-pentadienoyl]-2-thiothiazoline in dry dimethylformamide (4 ml). The mixture was reacted at room temperature for 16 hours, and then the solvent was removed under reduced pressure. Chloroform was added to the residue obtained, insolubles were filtered, and the filtrate was concentrated under reduced pressure. The residue thus obtained was subjected to silica gel column chromatography. There was obtained from fractions eluted with chloroform - methanol (10 : 1) 187 mg (0.38 mmol) of 4-[5-[3,5-dimethoxy-4($\beta$-methoxyethoxymethoxy)-phenyl]-2,4-pentadienoyl]aminomethyl-3-hydroxy-5-hydroxymethyl-2-methylpyridine.

To a solution of 185 mg (0.38 mmol), of the amide compound prepared above in methanol (10 ml) was added 72 mg (0.38 mmcl) of p-toluenesulfonic acid monohydrate. The mixture was refluxed for 1.5 hours. The reaction solution was concentrated under reduced pressure, and water was added to the residue obtained, followed by adjustment of the pH with an aqueous solution of sodium carbonate to 9. Crystals then precipitated were isolated by filtration to give 130 mg (0.33 mmol) of 4-[5-(3,5-dimethoxy-4-hydroxyphenyl)-2,4-pentadineoyl]aminomethyl-3-hydroxy-5-hydroxymethyl-2-methylpyridine. Spectrophotometric data of the product support the structure shown below.

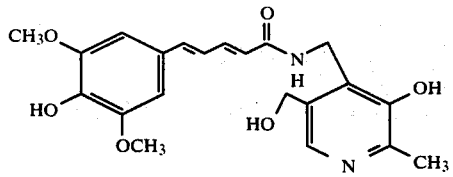

IR $\nu_{max}^{KBr}$(cm$^{-1}$): 3415, 1640, 1605, 1590.

$^1$H-NMR (pyridine-d$_5$) $\delta$: 2.68 (3H, s), 3.73 (6H, s), 4.68-5.00 (4H, m), 6.27 (1H, d, J=14HZ), 6.67-7.00 (5H, m), 8.20 (1H, s).

EXAMPLE 57

To an acetonitrile solution of 200 mg (0.06 mmol) of 5-{3,5-dimethoxy-4-($\beta$-methoxyethoxymethoxy)-phenyl}-2,4-pentadienic acid were added in an argone atmosphere 90 mg (0.6 mmol) of methyl anthranilate, 154 mg (0.6 mmol) of 2-chloro-1-methylpyridinium iodide and 0.5 ml of triethylamine. The mixture was heated under reflux for 18 hours. Water was added to the reaction solution, and the mixture was extracted with ethyl acetate. The organic layer was concentrated under reduced pressure, and the residue thus obtained was subjected to silica gel column chromatography. There was obtained from fractions eluted with benzene - ethyl acetate (10 : 1) 66 mg (0.14 mmol) of methyl N-[5-{3,5-dimethoxy-4-($\beta$-methoxyethoxymethoxy)-phenyl}-2,4-pentadienoyl]-anthranilate.

To a solution of 66 mg (0.14 mmol) of the amide compound prepared above in 4 ml of methanol were added 1 ml of water and then 100 mg of sodium hydroxide. The mixture was reacted at room temperature for 1 hour. To the reaction mixture was added 1N-hydrochloric acid to adjust the pH to 4. Crystals then produced were isolated by filtration to give 56 mg (0.12 mmol) of N-[5-{3,5-dimethoxy-4-($\beta$-methoxyethoxymethoxy)phenyl}-2,4-pentadienoyl]anthranilic acid.

To a solution of 56 mg (0.12 mmol) of the amide compound prepared above in 1 ml of dioxane was added 4 ml of 80% acetic acid. The mixture was heated under reflux for 2 hours. Water was added to the reaction solution, and crystals then formed were isolated by filtration and recrystallized from methanol. There was obtained 24 mg (0.65 mmol) of N-{5-(3,5-dimethoxy-4-hydroxyphenyl)-2,4-pentadienoyl}anthranilic acid. Spectrophotometric data of the product support the structure shown below.

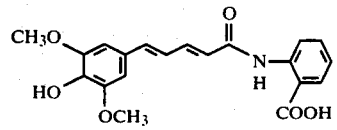

IR $\nu_{max}^{KBr}$(cm$^{-1}$): 3530, 1660, 1620, 1590.

$^1$H-NMR (deutero acetone) $\delta$: 3.83 (3H, s), 6.12 (1H, d, J=14Hz), 6.85 (2H, s), 6.90-7.67 (6H, m), 8.02 (1H., dd, J=8.2Hz), 8.75 (1H, d, d, J=8.1Hz).

EXAMPLE 58

To a solutioh of 130 mg (0.35 mmol) of the 4-[5-(3,5-dimethoxy-4-hydroxyphenyl)-2,4-pentadienoyl-]aminomethyl-3-hydroxy-5-hydroxymethyl-2-methylpyridine obtained in Example 56 in 5 ml of pyridine was added 240 mg (1.41 mmol) of toluoyl chloride. The mixture was reacted at room temperature for 24 hours. The reaction solution was poured onto ice water, and the pH was adjusted with an aqueous solution of sodium hydrogen carbonate to 9. The resulting mixture was extracted with ethyl acetate, and the organic layer was concentrated under reduced pressure. The residue thus obtained was subjected to silica gel column chromatography. There was obtained from fractions eluted with chloroform - methanol (50:1) 260 mg (0.34 mmol) of N-{5-(3,5-dimethoxy-4-toluoxyphenyl)-2,4-pentadienoyl}-O,O'-ditoluoylpyridoxamine.

To a solution of 260 mg (0.34 mmol) of the amide compound prepared above in a solution of tetrahydrofuran (8 ml) and water (2 ml) was added 0.5 ml (5.05 mmol) of piperidine. The mixture was reacted at room temperature for 48 hours. Then, water was added, and extraction was made with ethyl acetate. The organic layer was concentrated under reduced pressure, and the residue thus obtained was subjected to silica gel column chromatography. There was obtained from fractions eluted with chloroform 43 mg (0.07 mmol) of 4-{5-(3,5-dimethoxy-4-toluoxyphenyl)-2,4-pentadienoyl-}aminomethyl-3-hydroxy-2methyl-5-toluoxymethyl-pyridine. Spectrophotometric data of the product support the structure shown below.

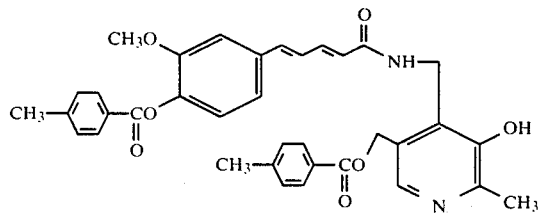

IR $\nu_{max}^{KBr}$ (cm$^{-1}$): 1735, 1720, 1655, 1615, 1600.

$^1$H-NMR (deutero pyridine) δ: 2.23 (6H, s), 2.73 (3H, s), 3.70 (6H, s), 4.86 (2H, d, j=7Hz), 5.60 (2H, s), 6.42 (1H, d, J=14Hz), 6.90–7.40 (9H, m), 8.06 (2H, d, J=8Hz), 8.30 (2H, d, J=8Hz), 8.43 (1H, s).

EXAMPLE 59

To a solution of 1.532 g (38.30 mmol) of a mineral oil containing 60% sodium hydride in dry tetrahydrofuran (100 ml) was added in an argon atmosphere 8.5 ml (38.32 mmol) of triethyl-4-phosphonocrotonate. The mixture was reacted at 0° C. for 1 hour, followed by addition of a solution of 5.012 g (25.55 mmol) of 3,4,5-trimethoxybenzaldehyde in dry tetrahydrofuran (50 ml). The mixture was reacted at room temperature for 2 hours. To the reactiuon mixture was added saturated aqueous solution of ammonium chloride, and the mixture was extracted with ethyl acetate. The organic layer was concentrated under reduced pressure, and the residue thus obtained was subjected to silica gel column chromatography. There was obtained from fractions eluted with benzene - ethyl acetate (9 : 1) 5.01 g (17.2 mmol) of ethyl 5-(3,4,5-trimethoxyphenyl)-2,4-pentadienoate.

To a solution of 1.93 g (6.61 mmol) of the ester compound prepared above in methanol (20 ml) was added a water - methanol (1 : 4) solution of 2.67 g (66.7 mmol) of sodium hydroxide. The mixture was reacted at room temperature for 22.5 hours. Water was added to the reaction solution, followed by adjustment of the pH with 1-N-hydrochloric acid to 3.5. The resulting mixture was extracted with chloroform, and the organic layer was concentrated under reduced pressure to give 1.70 g (6.44 mmol) of 5-(3,4,5-trimethoxyphenyl)-2,4-pentadienic acid.

To a solution of 1.70 g (6.44 mmol) of the acid compound prepared above in dry dichlorethane (50 ml) were added in an argon atmosphere 0.85 g (7.14 mmol) of 2-mercaptothiazoline, 80 mg (0.65 mmol) of 4-dimethylaminopyridine and 1.56 g (7.08 mmol) of N,N'-dicyclohexylcarbodiimide. The mixture was reacted at room temperature for 40 hours. The reaction mixture was filtered, and the filtrate was concentrated under reduced pressure and diluted with methylene chloride, followed by washing with water and 2N-aqueous solution of sodium hydroxide. The organic layer was concentrated under reduced pressure, and the residue thus obtained was subjected to silica gel column chromatography. There was obtained from fractions eluted with benzene - ethyl acetate (20:1–5:1) 1.90 g (5.21 mmol) of N-[5-(3,4,5-trimethoxyphenyl) 2,4-pentadienoyl]-2-thiothiazoline.

To a solution of 114 mg (0.27 mmol) of N-(p-chlorobenzhydryl)-N'-(2-phthalylaminoethyl)piperazine in ethanol (4 ml) was added in an argon atmosphere 40 mg (0.64 mmol) of 80% aqueous solution of hydrazine hydrate. The mixture was refluxed for 1.5 hours. After completion of the reaction, the solvent was removed by distillation under reduced pressure, and 3 ml of dry dimethylformamide was added to the residue obtained. To the resulting solution was added a solution of 113 mg (0.31 mmol) of the N-[5-(3,4,5-trimethoxyphenyl)-2,4-pentadienoyl]-2-thiothiazoline in dry dimethylformamide (4 ml). The mixture was reacted for 13 hours, and then the solvent was removed by distillation under reduced pressure. Chloroform was added to the residue obtained, insolubles were separated by filtration and the filtrate was concentrated under reduced pressure. The residue thus obtained was subjected to silica gel column chromatography. There was obtained from fractions eluted with ethyl acetate 105 mg (0.19 mmol) of N-[2-[5-(3,4,5-trimethoxyphenyl)-2,4-pentadienoyl]aminoethyl]-N'-benzhydrylpiperazine. Spectrophotometric data of the product support the structure shown below.

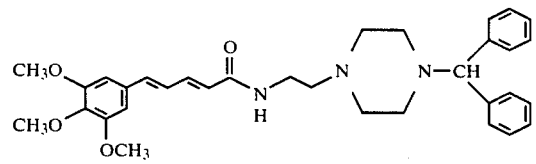

IR $\nu_{max}^{CHCL_3}$ (cm$^{-1}$): 1660, 1605, 1580.

$^1$H-NMR (deutero chloroform) δ: 2.43 (10H, br. s), 3.20–3.55 (2H, m), 4.13 (1H, br, s), 4.77 (9H, s), 5.88 (1H, d, J=14Hz), 6.1–6.3 (1H), 6.50–7.50 (13H).

EXAMPLE 60

In 20 ml of dry dimethylformamide was suspended in an argon atmosphere 1180 mg (4.56 mmol) of pyridoxamine dihydrochloride monohydrate, followed by addition of 3.2 ml (23 mmol) of triethylamine. The mixture was stirred at room temperature for 15.5 hours, followed by addition of a solution of 829 mg (12.27 mmol) of N-[5-(3,4,5-trimethoxyphenyl)-2,4-pentadienoyl]-2-thiothiazoline in dry dimethylformamide (20 ml). The mixture was reacted at room temperature for 4.5 hours. The reaction mixture was then concentrated under reduced pressure, precipitates were separated by filtration and the filtrate was extracted with ethyl acetate. The organic layer was concentrated under reduced pressure and combined residue and precipitates were subjected to silica gel column chromatography. There were obtained from fractions eluted with ethyl acetate - ethyl acetate : methanol (4 : 1) 670 mg (1.62 mmol) of 4-[5-(3,4,5-trimethoxyphenyl)-2,4-pentadienoyl]aminomethyl-3-hydroxy-5-hydroxymethyl-2-methylpyridine.

Spectrophotometric data of the product support the structure shown below.

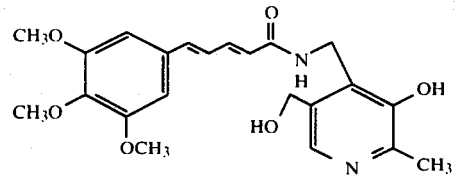

IR $\nu_{max}^{KBr}$(cm$^{-1}$) 3280, 1640, 1610, 1580. $^1$H-NMR (dimethylsulfoxide-d$_6$) δ: 2.34 (3H, s), 3.36 (3H, s), 3.80 (6H, s), 4.25–4.50 (2H, m), 4.58 (2H, m), 6.16 (1H, d J=14Hz), 6.76–7.40 (5H m).

EXAMPLE 61

To a solution of 1.85 g (46.3 mmol) of a mineral oil containing 60% sodium hydride in dry tetrahydrofuran (100 ml) was added in an argon atmosphere 10.6 ml (47.8 mmol) of triethyl 4-phosphonocrotonate. The mixture was reacted at 0° C. for 1 hour, followed by addition of 4.86 g (32.3 mmol) of piperonal. The mixture was reacted at room temperature for 1.5 hours. Saturated aqueous solution of ammonium chloride was added to the reaction solution, and the resulting mixture was extracted with ethyl acetate. The organic layer was concentrated under reduced pressure and subjected to silica gel column chromatography. There was obtained 7.23 g (29.6 mmol) of ethyl 5-(3,4-methylenedioxyphenyl)-2,4-pentadienoate. Spectrophotometric data of the product support the structure shown below.

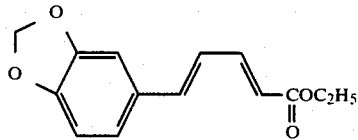

$^1$H-NMR (deutero chloroform) δ: 1.28 (3H, t, J=7Hz), 4.17 (2H, q, J=7Hz), 5.85 (1H, d, J=15 Hz), 5.90 (2H, s), 6.57–7.55 (6H, m).

To a solution of 6.8 g (27.6 mmol) of the ester compound prepared above in methanol (20 ml) was added in an argon atmosphere a solution of 11.0 g (275 mmol) of sodium hydroxide in water - methanol (1 : 6, 280 ml). The mixture was reacted at room temperature for 4.5 hours. Water was added to the reaction solution, followed by adjustment of the pH with 6N-hydrochloric acid to 3. Crystals then precipitated were isolated by filtration. There was obtained 5.478 g (25.1 mmol) of 5-(3,4-methylenedioxyphenyl)-2,4-pentadienic acid.

To a solution of 1.01 g (4.63 mmol) of the acid compound prepared above in dry dimethylformamide (7 ml) were added in an argon atmosphere 605 mg (5.08 mmol) of 2-mercaptothiazoline, 55 mg (0.45 mmol) of 4-dimethylaminopyridine and 1.06 g (5.15 mmol) of N,N'-dicylohexylcarbodiimide. The mixture was reacted at room temperature for 24 hours. The reaction solution was diluted with ethyl acetate. The organic layer was washed with water and concentrated under reduced pressure. The residue thus obtained was subjected to silica gel column chromatography. There was obtained from fractions eluted with chloroform 732 mg (2.29 mmol) of N-[5-(3,4-methylenedioxyphenyl) -2,4-pentadienoyl]-2-thiazoline.

To a solution of 55 mg (0.13 mmol) of N-(p-chlorobenzhydryl)-N'-(2-phthalylaminoethyl)piperazine in ethanol (3 ml) were added in an argon atmosphere 17 mg (0.27 mmol) of 80% aqueous solution of hydrazine hydrate. The mixture was refluxed for 1.5 hours. After completion of the reaction, the solvent was removed by distillation under reduced pressure, and 2 ml of dry dimethylformamide was added to the residue obtained. To the resulting solution was added a solution of 50 mg (0.16 mmol) of N-[5-(3,4-methylenedioxyphenyl)-2,4-pentadienoyl]-2-thiothiazoline in dry dimethylformamide. The mixture was reacted at room temperature for 1.5 hours. Then, the solvent was removed by distillation under reduced pressure, and chloroform was added to the residue obtained. Insolubles were separated by filtration, and the filtrate was concentrated under reduced pressure. The residue thus obtained was subjected to silica gel column chromatography. There was obtained from a fraction eluted with ethyl acetate 51 mg (0.10 mmol) of N-[2-[5-(3,4-methylenedioxyphenyl)-2,4-pentadienoyl]aminoethyl]-N'-benzhydrylpiperazine. Spectrophotometric data of the product support the structure shown below.

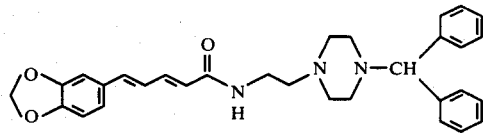

IR $\nu_{max}^{CHCl_3}$(cm$^{-1}$): 3390, 1710, 1655, 1600.

$^1$H-NMR (deutero chloroform)δ: 2.40 (10H, br. s), 3.20–3.65 (2H, m), 4.20 (1H, br, s), 5.90 (2H, s), 5.93 (1H, d, J=15Hz), 56.10–6.40 (1H), 6.50–7.60 (16H, m).

EXAMPLE 62

To a solution of 156 mg (0.355 mmol) of N-(benzhydryl)-N'-(3-phthalylaminopropyl)piperazine in 95% aqueous ethanol (4.210 ml) was added in an argon atmosphere 61 mg (0.975 mmol) of 80% aqueous solution of hydrazine hydrate. The mixture was refluxed for 3 hours. After completion of the reaction, the reaction mixture was concentrated under reduced pressure, and dry dimethylformamide (4 ml) was added to the residue obtained. To the resulting solution was added a solution of 167 mg (0.523 mmol) of N-[5-(3,4-methylenedioxyphenyl) -2,4-pentadienoyl]-2-thiothiazoline in dry dimethylformamide (8 ml). The mixture was reacted at room temperature for 66 hours. Water was added to the reaction mixture, and the mixture was extracted with ethyl acetate. The organic layer was concentrated under reduced pressure, and the residue thus obtained was subjected to silica gel column chromatography. There was obtained from a fraction eluted with chloroform-methanol (50 : 1) 153 mg (0.300 mmol) of N-[3-[5-(3,4,-methylenedioxyphenyl)-2,4-pentadienoyl]aminopropyl]-N'-benzhydrylpipeerazine. Spectrophotometric data of the product support the structure shown below.

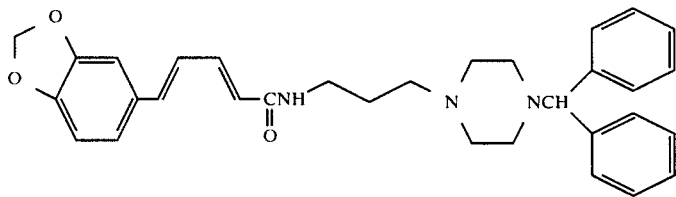

IR $\nu_{max}^{cm-1}$ (CHCl$_3$): 3250, 1660, 1610.

$^1$H-NMR (deutero chloroform)δ: 1.65 (2H, m), 2.45 (10H, bs), 3.38 (2H, m), 4.20 (1H, s), 5.90 (2H, s), 6.55–7.48 (16H, m).

EXAMPLE 63

To a solution of 2.25 g (7.83 mmol) of N-(p-chlorobenzhydryl)piperazine in dry xylene (20 ml) was added, under argon atmosphere, 1.48 g (5.25 mmol) of N-(4-bromobutyl)phthalimide, and the mixture was refluxed for 9 hours. After the reaction mixture was allowed to cool, a dilute aqueous solution of sodium carbonate was added and the mixture was extracted with chloroform. The organic layer was washed with water and concentrated under reduced pressure. The residue was subjected to silica gel column chromatography. There was obtained from fractions eluted with chloroform 1.46 g (2.99 mmol) of N-(p-chlorobenzhydryl)-N-(4-phthalylaminobutyl)piperazine.

To a solution of 555 mg (1.14 mmol) of the phthalimide compound in ethanol (5 ml) was added 85 mg (1.36 mmol) of 80% aqueous solution of hydrazine hydrate, and the mixture was refluxed for 3.5 hours. After completion of reaction,, the reaction mixture was filtered and the filtrate was distilled off under reduced pressure. To the resulting residue was added 5 ml of dry N,N-dimethylformamide, followed by a solution of 620 mg (1.36 mmol) of [3-[3,4-di-(β-methoxyethoxymethoxy)-phenyl]-2-propenoyl]thiazolidin-2-thione in dry N,N-dimethylformamide(4 ml). The whole mixture was allowed to react at room temperature for 17 hours and the solvent was removed by distillation. Chloroform was added to the residue and the insolubles were filtered off. The iltrate was concentrated by evaporation under reduced pressure and the residue was subjected to silica gel column chromatography. There was obtained from fractions eluted with chloroform-methanol (50 : 1–20 1) 661 mg (0.95 mmol) of N-[4-[3-[3,4-di-(β-methoxyethoxymethoxy)phenyl]-2-propenoyl]aminobutyl]-N'-(p-chlorobenzhydryl) piperazine. To a solution of 630 mg (0.91 mmol) of the amide compound in methanol (10 ml) was added 190 mg (1 mmol) of p-toluenesulfonic acid monohydrate, and the mixture was refluxed for 2.5 hours. The reaction mixture was concentrated by evaporation under reduced pressure and water was added to the resulting residue. The mixture was adjusted to a pH value of 10 by the addition of a saturated aqueous solution of sodium carbonate and extructed with chloroform - methanol (20 : 1). The organic layer was concentrated by evaporation under reduced pressure and the residue was subjected to Sephadex column chromatography. There was obtained from fractions eluted with methanol 446 mg (0.77 mmol) of N-[4-[3-(3,4-dihydroxy)phenyl]-2-propenoyl]aminobutyl]-N'-(p-chlorobenzhydryl)piperazine.

Spectrophotometric data of the product support the structure shown below.

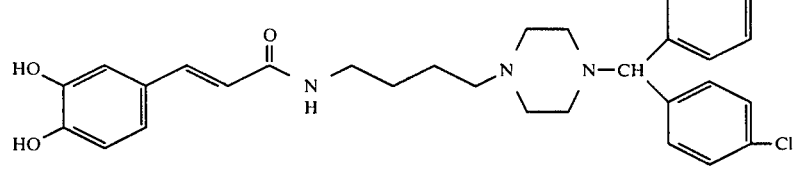

IR $\nu_{max}^{KBr}$(cm$^{-1}$): 3220, 1660, 1600.

$^1$H-NMR (CD$_3$OD)δ: 1.30–1.90 (4H, m), 2.10–2.80 (10H, m), 3.10–3.73 (2H, m), 4.15 (1H, s), 6.31 (1H, d, J=15Hz), 6.60–7.90 (13H).

EXAMPLE 64

To a solution of 1.56 g of N-4-bromobutylphthalimide in benzene (30 ml) was added, under argon atmosphere, 2.09 g of N-benzhydrylpiperazine, and the mixture was refluxed for 23 hours. A saturated aqueous solution of sodium hydrogencarbonate was added to the reaction mixture and, after extraction, the organic layer was concentrated by evaporation under reduced pressure. The residue was subjected to silica gel column chromatography. There was obtained from fractions eluted with chloroform - methanol (100 : 1–50 : 1) 2.00 g of N-benzhydryl-N'-4-phthalylaminobutylpiperazine. To a solution of 500 mg (1.10 mmol) of the piperazine compound in ethanol (10 ml) was added, under argon atmosphere, 138 mg (2.21 mmol) of 80% hydrazine hydrate, and the mixture was heated and refluxed for 2 hours. The reaction mixture was filtrated and the filtrate was concentrated by evaporation under reduced pressure. To the residue was added 5 ml of dry tetrahydrofuran, followed by a solution of 620 mg (1.36 mmol) of N-[3-[3,4-di-(methoxyethoxymethoxy)phenyl]-2-propenoyl]thiazolidine -2-thione in dry tetrahydrofuran (6 ml), and the mixture was allowed to react at room temperature overnight. The reaction mixture was concentrated by evaporation under reduced pressure and chloroform was added to the resulting residue. Insolubles were filtered off and the filtrate was concentrated by evaporation under reduced pressure.

The residue was subjected to silica gel column chromatography, eluted with chloroform - methanol (100 : 1–50 : 1), to give 750 mg (1.0 mmol) of N-[4-[3-(3,4- dimethyoxyethoxymethoxyphenyl) -2-propenoyl-]aminobutyl-N'-benzhydrylpiperazine.

To a solution of 750 mg (1.0 mmol) of the amide compound in methanol (10 ml) was added 225 mg (1.18 mmol) of p-toluenesulfonic acid monohydrate, and the mixture was heated and refluxed for 2 hours. The reaction mixture was concentrated by evaporation under reduced pressure. Water was added to the resulting residue and the mixture was adjusted to a pH value of 10 by the addition of a saturated aqueous solution of sodium carbonate, and then the whole mixture was extracted with chloroform. The organic layer was concentrated by evaporation under reduced pressure and the residue was subjected to Sephadex LH-20 column chromatography. There was obtained from fractions eluted with methanol 423 mg (0.87 mmol) of N-[4-[3-,4-(3,4-dihydroxyphenyl)-2-propenoyl]aminobutyl]N'-benzhydrylpiperazine. propenoyl]aminobutyl]N'-benzhydrylpiperazine.

Spectrophotometric data of the product support the structure shown below.

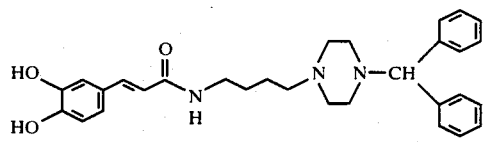

IR$\nu_{max}^{KBr}$ (cm$^{-1}$): 3220, 1660, 1600.

EXAMPLE 65

800 mg (20 mmol) of 60% sodium hydride was washed several times with n-hexane; 10 ml of dimethyl sulfoxide was added, and the mixture was heated, under argon atmosphere, at 70° C. -75° C. for 45 minutes. To the reaction mixture was added a supension of 3.6 g (20 mmol) of teophylline in 50 ml of dimethyl sulfoxide, and then the mixture was stirred at room temperature for 1 hour. To the mixture was added a solution of 5.08 g (20 mmol) of bromoethylphthalimide in dimethyl sulfoxide, and the whole mixture was allowed to react at room temperature overnight. Water was added to the reaction mixture and the precipitate formed was collected by filtration. Recrystallization of the precipitate from methanol yielded 3.95 g (11.2 mmol) of 7-(2-phthalylaminoethyl)-theophylline.

To a solution of 706 mg (2 mmol) of the theophilline derivative in 50ml of ethanol was added 500 mg (8 mmol) of 80% hydrazine hydrate, and then the mixture was refluxed, under argon atmosphere, for 2 hours. To the reaction mixture was added 100 ml of n-butanol, and the whole mixture was allowed to cool to room temperature. The resulting crystals were filtered off and the filtrate was concentrated by evaporation under reduced pressure. The residue was dissolved in 10 ml of dimethylformamide, a solution of 914 mg (2 mmol) of N-[3-[3,4-di-(β-methoxyethoxymethoxy)phenyl]-2-propenoyl]-thiazolidene-2-thione in dimethylformamide (5 ml) was added, and then the mixture was reacted at room temperature for 2 hours. The reaction mixture was concentrated by evaporation under reduced pressure and the residue was subjected to silica gel column chromatography. There was obtained from fractions eluted with chloroform - methanol (50 : 1) 861 mg (1.53 mmol) of 7-[2-[3-[3,4-di-(β-methoxyethoxymethoxy)-phenyl]-2-propenoyl]aminoethyl]theophylline.

To a solution of 861 mg (1.53 mmol) of the amide compound in 50 ml of methanol was added 760 mg (4 mmol) of p-toluenesulfonic acid monohydrate, and the mixture was heated and refluxed for 1 hour. The reaction mixture was adjusted to a pH value of 10 by the addition of a saturated aqueous solution of sodium hydrogencarbonate. Water was added to the mixture and the precipitate formed was collected by filtration. Recrystallization of the precipitate from methanol yhielded 410 mg (1.06 mmol) of of 7-[2-[3-(3,4-dihydroxy)phenyl-2-propenoyl]aminoethyl]theophilline.

Spectrophotometric data of the product support the structure shown below.

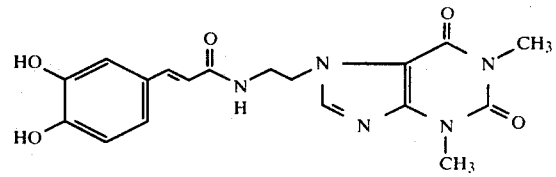

$^1$H-NMR (d$_6$-DMSO)δ: 3.22 (3H, s), 3.42 (3H, s), 3.75 (2H, m), 4.33 (2H, m), 6.17 (1H, d, J=16Hz), 6.85 (1H, bs), 6.72 (2H, bs), 7.17 (1H, d, J=16Hz), 7.85 (1H, s)
IR$\nu_{max}^{KBr}$ (cm$^{-1}$): 3350, 1702, 1650, 1640, 1600.

EXAMPLE 66

To 3.00 g (13.2 amol) of benzhydryl 2-chloroethyl ether was added, under argon atmosphere, 4 ml (27.3 mmol) of ethyl N-piperazinocarboxylate, and the mixture was reacted at 160° C. for 1 hour.

After the reaction mixture was allowed to cool, water was added and the whole mixture was adjusted to a pH value of 10 by the addition of an aqueous solution of sodium carbonate. The mixture was extracted with ethyl acetate and the organic layer was concentrated by evaporation under reduced pressure. The residue was subjected to silica gel column chromatography, eluted with ethyl acetate- hexane (1 : 1), to give 4.12 g (11.2 mmol) of N-(2-benzhydroxyethyl)-N'-ethoxycarbonyl-piperazine.

To a solution of 4.12 g (11.2 mmol) of the piperazine derivative in methanol (20 ml) and water (10 ml) was added 13.2 g (235 mmol) of of potassium hydroxide, and the mixture was refluxed for 19 hours. Water was added to the reaction mixture and the whole mixture was extracted with n-butanol. The organic layer was washed with water and concentrated by evaporation under reduced pressure. The residue was subjected to Sephadex column chromatography, eluted with methanol, to give 3.15 g (10.6 mmol) of N-(2-benzhydroxyethyl)piperazine.

To a solution of 265 mg (0.894 mmol) of the amine compound in dry dimethylformamide (5 ml) was added 620 mg (1.36 mmol) of N-[3-[3,4-bis(β-methoxyethoxymethoxy) phenyl]-2-propenoyl]thiazolidine-2-thione, and the mixture was reacted at room temperature for 18 hours. The reaction mixture was concentrated by evaporation under reduced pressure and the residue was subjected to silica gel column chromatography.

There was obtained from fractions eluted with chloroform - methanol (100 : 1) 561 (0.884 mmol) of N-[3-[3 4-bis(β-methoxyethoxymethoxy)phenyl]-2-propenoyl]N'-(2-benzhydroxyethyl)piperazine.

To a solution of 561 mg (0.884 mmol) of the amide compound in methanol (10 ml) was added 178 mg (0.936 mmol) of p-toluenesulfonic acid monohydrate, and then the mixture was refluxed for 4 hours. The reaction mixture was concentrated by evaporation under reduced pressure and water was added to the residue. The mixture was adjusted to a pH value of 10 by the addition of an aqueous solution of sodium carbonate and extracted with n-butanol. The organic layer was washed with water, concentrated by evaporation under reduced pressure and the residue was subjected to Sephadex column chromatography. There was obtained from fractions eluted with methanol 242 mg (0.528 mmol) of N-[3-(3,4-dihydroxyphenyl)-2-propenoyl]-N'-(2-benzhydroxyethyl) Spectophotometric data of the product support the structure shown below.

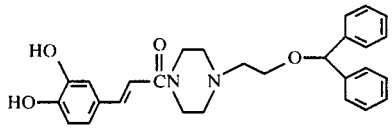

IR$\nu_{max}^{KBr}$ (cm$^{-1}$): 3100, 1640, 1600, 1585.
$^1$H-NMR (deutro methanol)δ: 2.47 (6H, m), 3.53 (6H, m), 5.30 (1H, s), 6.57-7.60 (15H, m).

EXAMPLE 67

To a solution of 3.27 g of 2-chloroethanol in dry benzene (3.5 ml) was added 0.8 g of conc. sulfuric acid and the mixture was heated, under argon atmosphere, at 50° C. To the mixture was added slowly a solution of 5.0 g of benzhydrol in dry benzene (6.5 ml) and, after 30 minutes from the addition, the whole mixture was refluxed for 1.5 hours. After the mixture was allowed to cool, the benzene layer was washed with water and dried over anhydrous sodium sulfate. The solvent was removed by distillation under reduced pressure, to give 6.7 g of benzhydryl 2-chloroethyl ether.

To a solution of 3.7 g of the ether compound in dry dimethylformamide (30 ml) was added 3.4 g of potassium phthalimide, and the mixture was reacted at 100° C. for 2 hours. The reaction mixture was filtered and the solvent was distilled off under reduced pressure. Recrystallization of the residue from methanol yielded 4.4 g of benzhydryl 2-phthalylaminoethyl ether.

To a solution of 536 g of benzhydryl 2-phthalylaminoethyl ether in ethanol (10 ml) was added 150 mg of 80% aqueous solution of hydrazine hydrate, and then the mixture was refluxed for 1.5 hours. The reaction mixture was concentrated by evaporation under reduced pressure and the residue was suspended in 20 ml of dry tetrahydrofuran. To the suspension was added 460 mg of N-[3-(3,4-di-β-methoxyethoxymethoxy)phenyl-2-propenoyl-thiazolidine-2-thione, and the mixture was stirred at room temperature for 20 hours under argon atmosphere. The reaction mixture was concentrated by evaporation under reduced pressure. 2N aqueous solution of sodium hydroxide was added to the residue and the mixture was extracted with chloroform. The organic layer was concentrated by evaporation under reduced pressure and the residue was subjected to silica gel column chromatography. There was obtained from fractions eluted with chloroform - methanol (50 : 1) 433 mg of 2-[3-(3,4-di-β-methoxyethoxymethoxyl) phenyl-2-propenoyl]aminoethylbenzhydryl ether.

To a solution of 430 mg of the amide compound in methanol (15 ml) was added 15.2 mg of p-toluenesulfonic acid monohydrate, and the mixture was refluxed for 1 hour. A saturated aqueous solution of sodium hydrogen carbonate was added to the reaction mixture, which was extracted wiith ethyl acetate. The residue was subjected to silica gel column chromatography. There was obtained from fractions eluted with chloroform - methanol (50 : 1) 162 mg of 2-[3-(3,4-dihydroxy)-phenyl-2-propenoyl]aminoethyl benzhydryl ether. Spectrophotometric data of the product support the structure shown below.

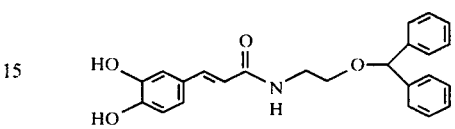

$^1$H-NMR (CD$_3$)δ(ppm): 3.63 (4H, m), 5.40 (1H, s), 6.13 (1H, d (J=15Hz), 6.40 (1H, bs), 6.63-7.80 (16H, m).
IR$\nu_{max}^{KBr}$ (cm$^{-1}$) 3300, 1650, 1600, 1510, 1280.

EXAMPLE 68

To a solution of 500 mg (1.10 mmol) of N-benzhydryl-N'-(4-phthalylaminobutyl)piperazine in ethanol (10 ml) was added 138 mg (2.21 mmol) of 80% aqueous solution of hydrazine hydrate, and the mixture was refluxed for 2.5 hours under argon atmosphere. After completion of reaction, the reaction mixture was filtered and the filtrate was concentrated by evaporation under reduced pressure. The residue was dissolved in 5 ml of dry tetrahydrofuran and, then a solution of 492 mg (1.28 mmol) of N-[3-[3-methoxy-4-(β-methoxyethoxymethoxy)phenyl]-2-propenoyl]thiazolidine-2-thione in dry tetrahydrofuran(86 ml) was added. The mixture was allowed to react at room temperature for 23.5 hours and, at the end of this period, the solvent was distilled off under reduced pressure. Chloroform was added to the residue and insolubles were filtered off. The filtrate was concentrated by evaporation under reduced pressure and the residue was subjected to silica gel column chromatography.

There was obtained from fractions eluted with chloroform - methanol (100 : 1–50 : 1) 640 mg (1.09 mmol) of N-[4-[4-methoxy-4-(β-methoxyethoxymethoxy)-phenyl]-2-propenoyl]aminobutyl]-N'-benzhydrylpiperazine. To a solution of 630 mg (1.07 mmol) of the amide compound in methanol (10 ml) was added 225 mg (1.18 mmol) of p-toluenesulfonic acid monohydrate, and the mixture was refluxed for 4.5 hopurs. The reaction mixture was concentrated by evaporation under reduced pressure and water was added to the residue.

The mixture was adjusted to a pH value of 10 by the addition of a saturated aqueous solution of sodium carbonate and extracted with chloroform. The organic layer was concentrated by evaporation under reduced pressure and the residue was subjected to Sephadex column chromatography. There was obtained from fractions eluted with methanol 461 mg (0.92 mmol) of N-[4-3-(3-methoxy-4-hydroxy) phenyl]-2-propenoyl]aminobutyl]-N'-benzhydrylpiperazine. Spectrophotometric data of the product support the structure shown below.

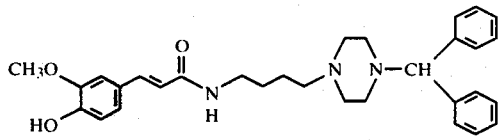

IR$\nu_{max}^{KBr}$ (cm$^{-1}$): 3220, 2660, 2600.

$^1$H-NMR (deutero chloroform)δ: 1.30–1.90 (4H, m), 2.10–2.90 (10H, br, s), 3.10–3.60 (2H, m), 3.75 (3H, s), 4.20 (1H, s), 6.27 (1H, d, J=16Hz), 7.80–6.60 (14H).

EXAMPLE 69

To a solution of 353 mg (1 mmol) of 7-(2-phthalylaminoethyl) theophylline in 20 ml of ethanol was added 250 mg (4 mmol) of 80% hydrazine hydrate, and the mixture was refluxed for 2 hours under argon atmosphere. After completion of reaction, 50 ml of n-butanol was added and the mixture was allowed to cool to room temperature. Crystals precipitated were filtered off and the filtrate was concentrated by evaporation under reduced pressure. The residue was dissolved in 5 ml of dimethylformamide and a solution of 383 mg (1 mmol) of N-[3-(3-methoxy-4-β-methoxyethoxymethoxy)phenyl-2-propenoyl] -thiazolidine-2-thione in dimethylformamide (2 ml) was added. The whole mixture was reacted at room temperature for 2 hours and, at the end of this period, it was concentrated by evaporation under reduced pressure. The residue was subjected to silica gel column chromatography, eluted with chloroform - methanol (50 : 1), to give 365 mg (0.75 mmol) of 7-[2-[3-(3-methoxy-4-β-methoxyethoxymethoxy) phenyl-2-propenoyl]aminoethyl]theophylline.

To a solution of 365 mg (0.75 mmol) of the amide in 30 ml of methanol was added 380 mg (2 mmol) of p-toluene-sulfonic acid monohydrate, and the mixture was refluxed for 1 hour. A saturated aqueous solution of sodium hydrogencarbonate was added to the reaction mixture to adjusted the pH value at 10, and water was added to give a precipitate. It was collected by filtration and recrystallized from methanol, affording 209 mg (0.52 mmol) of 7-[2-[3-(3-methoxy-4-hydroxy)phenyl-2-propenoyl]aminoethyl]theophylline. Spectrophotometric data of the product support the structure shown below.

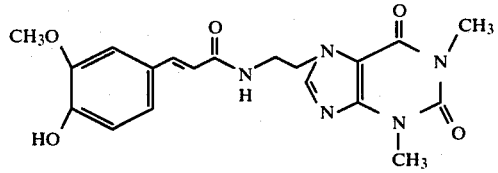

IR$\nu_{max}^{KBr}$ (cm$^{-1}$): 3300, 1705, 1660, 1645, 1610.

EXAMPLE 70

To a solution of 625 mg (2.11 mmol) of N-(2-benzhydroxyethyl)piperazine in dry dimethylformamide (2 ml) was added, under argon atmosphere, a solution of 998 mg (2.60 mmol) of N-[3-[3-methoxy-4-(β-methoxyethoxymethoxy) phenyl]-2-propenoyl]thiazolidine-2-thione in dry dimethylformamide (4 ml), and the mixture was reacted at room temperature for 2 hours. The reaction mixture was concentrated by evaporation under reduced pressure and the residue was subjected to silica gel column chromatography. There was obtained from fractions eluted with chloroform - methanol (100 : 1) 813 mg (1.45 mmol) of N-[3-[3-methoxy-4-(β-methoxyethoxymethoxy)phenyl]-2-propenoyl]-N'-(2-benzhydroxyethyl)piperazine.

To a solution of 813 mg (1.45 mmol) of the amide compound in methanol (16 ml) was added 288 mg (1.51 mmol) of p-toluenesulfonic acid monohydrate, and the mixture was reacted for 1 hour. Water was added to the reaction mixture, which was adjusted to a pH value of 10 by the addition of an aqueous solution of sodium carbonate, after which it was extracted with ethyl acetate. The organic layer was washed with water and concentrated by evaporation under reduced pressure. The residue was subjected to Sephadex column chromatography, eluted with methanol, to give 556 mg (1.18 mmol) of N-[3-methoxy-4-hydroxyphenyl) -2-propenoyl]-N'-(2-benzhydroxyethyl)piperazine. Spectrophotometric data of the product support the structure shown below.

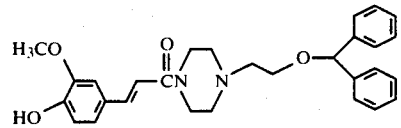

IR$\nu_{max}^{KBr}$ (cm$^{-1}$): 3300, 1645, 1600, 1590.

$^1$H-NMR (deutro methanol)δ: 2.48 (6H, m), 3.63 (6H, m), 3.80 (3H, s), 5.32 (15H, s), 6.75 - 7.72 (15H, m).

EXAMPLE 71

To a solution of 3.85 g (40.7 mmol) of 3-chloro-1-propanol in benzene (4 ml) was added conc. sulfuric acid, followed by a solution of 5 g (27.2 mmol) of benzhydrol in benzene (6 ml), and the mixture was refluxed, under argon atmosphere, for 0.8 hours. The reaction mixture was diluted with benzene, washed with water and the organic layer was dried over magnesium sulfate. The solvent was distilled off under reduced pressure and there was obtained 6.80 g (26.1 mmol) of benzhydryl 3-chloropropyl ether.

To 6.80 g (26.1 :mmol) of the ether compound was added 9.77 g (61.8 mmol) of ethyl N-piperazinocarboxylate and the mixture was reacted, under argon atmosphere, at the outer temperature of 150° C. for 23 hours. The reaction mixture was diluted with chloroform, washed, in turn, with an aqueous solution of sodium hydrogencarbonate and water, and the argon layer was dried over anhydrous solidum sulfate. The solvent was distilled off and the residue was subjected to silica gel column chromatography. There was obtained from fractions eluted with ethyl acetate - benzene (1 : 5–1 : 1) 9.47 g (24.8 mmol) of N-(3-benzhydroxypropyl)-N'-ethoxycarbonyl-piperazine.

To a solution of 9.47 g (24.8 mmol) of the piperazine derivative in methanol (20 ml) was added a solution of 28 g (0.5 mmol) of potassium hydroxide in water - methanol (1: 260 ml), and the mixture was refluxed, under argon atmosphere, for 21 hours. Water was added to the reaction mixture, which was then extracted with ethyl acetate. The organic layer was concentrated by evaporation under reduced pressure to give 7.5 g (24.4 mmol) of N-(3-benzhydroxypropyl)piperazine.

To a solution of 620 mg (2 mmol) of the piperazine derivative in dry tetrahydrofuran (5 ml) was added a solution of 766 mg (2.0 mmol) of N-[3-[3-methoxy-4-(β- methoxyethoxymethoxy)phenyl]-2-propenoyl) thiazolidine-2-thione in dry tetrahydrofuran (5 ml), and the mixture was allowed to react at room temperature overnight under argon atmosphere. The reaction mixture was concentrated by evaporation under reduced pressure, diluted with N'chloroform and washed, in turn, with 2N aqueous solution of sodium hydroxide and water. The organic layer was dried over anhydrous scdium sulfate and concentrated by evaporation under reduced pressure. The residue was subjected to silica gel column chromatography, eluted with chloroform - methanol ((50 : 1), to give 1.08 g (1.88 mmol) of N-[3-[3-methoxy-4-(β-methoxyethoxymetoxy) phenyl]-2-propenoyl]-N'-(3-benzhydroxypropyl)-piperazine.

To a solution of 1.08 g (1.88 mmol) of the amide compound in 10 ml of methanol was added 380 mg (2 mmol) of p-toluenesulfonic acid monohydrate, and the mixture was refluxed for 1 hour under argon atmosphere. The reaction mixture was concentrated by evaporation under reduced pressure, a saturated aqueous solution of sodium hydrogencarbonate was added to the residue, which was then extracted with ethyl acetate. The organic layer was dried over anhydrous sodium sulfate and concentrated by evaporation under reduced pressure. The residue was subjected to silica gel column chromatography, eluted with chloroform - methanol (20 : 1), to give 603 mg (1.24 mmol) of N-[3-(3-methoxy-4-hydroxy)phenyl-2-propenoyl]-(3-benzhydroxypropyl)piperazine.

Spectrophotometric data of the product support the structure shown below.

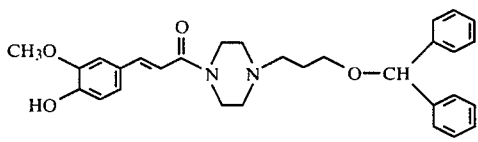

IR$\nu_{max}^{KBr}$ (cm$^{-1}$): 3400, 1640, 1585.

$^1$H-NMR (deutro methanol) δ: 1.98 (2H, m), 2.38 (6H, m), 3.58 (6H, m), 3.82 (3H, s), 5.28 (1H, s), 6.67–7.78 (15H, m).

EXAMPLE 72

To a solution of 471 mg of benzhydryl-2-phthalylaminoethyl ether in ethanol (6.5 ml) was added 132 mg of 80% aqueous solution of hydrazine hydrate, and the mixture was refluxed for 1.5 hours. The reaction mixture was concentrated by evaporation under reduced pressure and the residue was suspended in 20 ml of dry tetrahydrofuran. To the suspension was added 460.2 mg of N-3-(3-methoxy-4-β-methoxyethoxymethoxy)phenyl-2-propenoylthiazolidine-2-thione, and the mixture was stirred at room temperature for 20 hours, under argon atmosphere reaction mixture was concentrated by evaporation under reduced pressure and 2N aqueous solution of sodium, hydroxide was added to the residue. After extraction with chloroform, the The organic layer was concentrated by evaporation under reduced pressure and the residue was subjected silica gel column chromatography. There was obtained from fractions eluted with chloroform 548 mg of 2-[3-(3-methoxy-4-β-methoxy ethoxymethoxy) phenyl-2-propenoyl]aminoethyl benzhydryl ether.

To a solution of 545 mg of the amide compound in methanol (20 ml) was added 21 mg of p-toluenesulfonic acid monohydrate, and the mixture was refluxed for 1 hour. A saturated aqueous solution of sodium hydrogencarbonate was added to the reaction mixture, which was extracted with ethyl acetate. The solvent was distilled off and the residue was subjected to silica gel column chromatography. There was obtained from fractions eluted with chloroform - methanol (50 : 1) 334 mg of 2-[3-(3-methoxy-4-hydroxy)phenyl-2-propenoyl]aminoethyl benzhydryl ether. Spectrophotometric data of the product support the structure shown below.

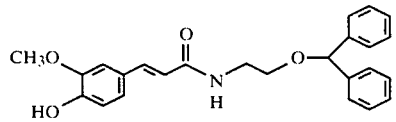

$^1$H-NMR (CDCL$_3$)δ(ppm): 3.53 (4H, m), 3.68 (1H, s), 6.30 (1H, s), 6./25 (1H, d (J=15Hz), 6.50 (1H, bs), 6.67–7.40 (14H, m), 7.50 (1H, d(J-15Hz).

IR$\nu_{max}^{KBr}$ (cm$^{-1}$): 3300, 1660, 1585, 1508, 1270.

EXAMPLE 73

To a solution of 2.6 (10 mmol) of benzhydryl 3-chloropropyl ether in dry dimethylformamide (20 ml) was added 2 g (10.8 mmol) of potassium phthalimide, and the mixture was reacted at 100° C. for 2 hours. The reaction mixture was filtered and the filtrate was concentrated under reduced pressure. The residue was recrystallized from methanol to give 3.04 g *8.2 mmol) of benzhydryl 3-phthalylaminoethyl ether. To a solution of 371 mg (1 mmol) of the ether compound in ethanol (10 ml) was added 125 mg (2 mmol) of 80% aqueous solution of hydrazine hydrate, and the mixture was refluxed for 2 hours. The reaction mixture was concentrated by evaporation under reduced pressure and the residue was suspended in 10 ml of dry tetrahydrofuran. To the suspension was added a solution of 490 mg (1.2 mmol) of N-[3-[3-methoxy-4-(β-methoxyethoxymethoxy) phenyl]-2-propenoyl]thiazolidine-2-thione 2-thione in dry tetrahydrofuran (10 ml), and the mixture was reacted at room temperature for 18 hours under argon atmosphere. The reaction mixture was concentrated by evaporation under reduced pressure and to the residue was added chloroform, washed with 2N aqueous solution of sodium hydroxide, and the organic layer was concentrated by evaporation under reduced pressure. The residue was subjected to silica gel column chromatography, eluted with chloroform, to give 378 mg (0.75 mmol) of 3-[3-[3-methoxy-4-(β-methoxyethoxymethoxy) phenyl]-2-propenoyl]aminopropyl benzhydryl ether.

To a solution of 378 mg (0.75 mmol) of the amide compound in methanol (10 ml) was added 19 mg (0.1 mmol) of p-toluenesulfonic acid monohydrate, and the mixture was heated and refluxed for 1 hour. A saturated aqueous solution of sodium hydrogencarbonate was added to the reaction mixture, which was extracted with ethyl acetate, and the organic layer was concentrated by evaporation under reduced pressure. The residue was subjected to silica gel column chromatography, eluted with chloroform - methanol (50 : 1), to give 230 mg (0.55 mmol) of 3-[3-[3-methoxy-4-hydroxyphenyl)-2-propenoyl]aminopropyl benzhydryl ether. Spectrophotometric data of the product support the structure shown below.

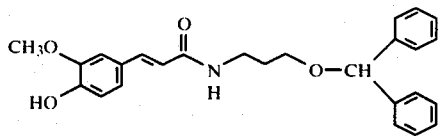

IR$\nu_{max}^{KBr}$ (cm$^{-1}$): 3300, 1655, 1610.

EXAMPLE 74

To a solution of 500 mg of N-benzhydryl-N'-(4-phthalylaminobutyl)piperazine in ethanol (10 ml) was added 138 mg (2.21 mmol) of 80% aqueous solution of hydrazine hydrate, and the mixture was heated and refluxed for 2 hours under argon atmosphere. The reaction mixture was filtered and the filtrate was concentrated by evaporation under reduced pressure. The residue was dissolved in 5 ml of dry tetrahydrofuran and a solution of 372 mg (1.2 mmol) of N-[3-(3,4-dimethoxyphenyl)-2-propenoyl]thiazolidine-2-thione in dry tetrahydrofuran (5 ml) was added. The mixture was allowed to react at room temperature overnight. The reaction mixture was concentrated by evaporation under reduced pressure and the residue was diluted with chloroform. Insolubles were filtered off and the filtrate was concentrated by evaporation under reduced pressure. The residue was subjected to silica gel column chromatography, eluted with chloroform-methanol (50 : 1), to give 500 mg (0.97 mmol) of N-[4-[3-(3,4-dimethoxyphenyl)-2-propenoyl]aminobutyl]-N'-benzhydrylpiperazine. Spectrophotometric data of the product support the structure shown below.

evaporation under reduced pressure. The residue was subjected to silica gel column chromatography, eluted with chloroform - methanol (50 : 1), to give 610 ml (1.48 mmol) of 7-[2-[3-(3,4-dimethoxyphenyl) -2-porpenoyl- ]aminoethyl]theophylline. Spectrophotometric data of the product support the structure shown below.

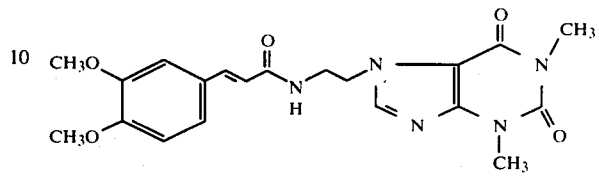

$^1$H-NMR (d6-DMSO)δ: 3.18 (3H, s), 3.32 (2H, m), 3.56 (2H, m), 3.67 (6H, s), 4.27 (2H, m), 6.23 (1H, d, J=16Hz), 7.20 (1H, d, J=16Hz, 6.80–7.03 (3H, m), 7.87 (1H, d, J=4Hz).

IR$\nu_{max}^{KBr}$ (cm$^{-1}$) 3300, 1702, 1660, 1655, 1615.

EXAMPLE 76

To a solution of 296 mg (1 mmol) of N-(2-benzhydroxyethyl) piperazine in dry dimethylformamide (2 ml) was added a solution of 372 mg (1.2 mmol) of N-[3-(3,4-dimethyoxyphenyl) -2-propenoyl]thiazolidine-2-thione in dry dimethylformamide (4 ml), and the mixture was reacted at room temperature for 2 hours under argon atmosphere. The reaction mixture was concentrated by evaporation under reduced pressure and the residue was subjected to silica gel column chromatography. There was obtained from fractions eluted with chloroform - methanol (100 : 1) 348 mg (0.72 mmol) of N-[3-(3,4-dimethoxyphenyl) -2-propenoyl]-N'-(2-benzhydroxyethyl)piperazine. Spectrophotometric data of the product support the structure shown below. .

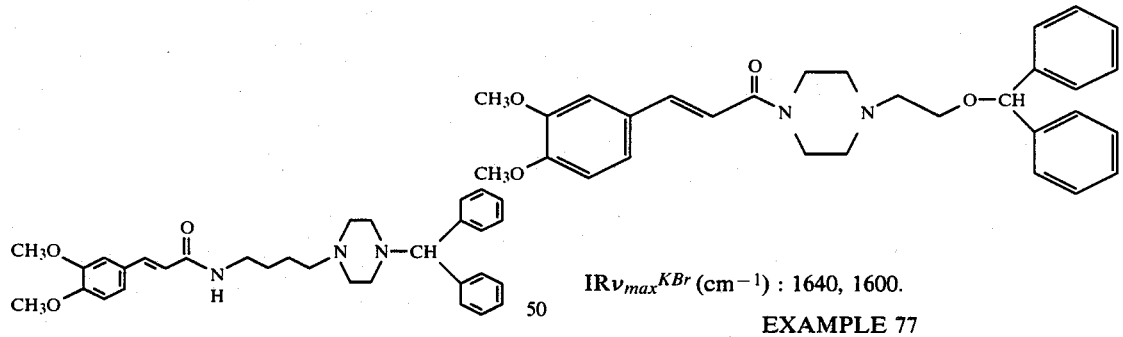

IR$\nu_{max}^{KBr}$ (cm$^{-1}$): 3300, 1660.

EXAMPLE 75

To a suspension of 706 mg (2 mmol) of 7-(2-phthalylaminoethyl theophylline in 50 ml of ethanol was added 500 mg (8 mmol) of 80% hydrazine hydrate, and the mixture was heated and refluxed for 2 hours under argon atmosphere. The reaction mixture was diluted with 100 ml of n-butanol, cooled to room temperature and the resulting crystals were filtered off. The filtrate was concentrated by evaporation under reduced pressure. The residue was dissolved in 10 ml of dimethylformamide and a solution of 620 mg (2 mmol) of N-[3-(3,4-dimethoxyphenyl) -2-propenoyl]thiazolidine-2-thione in 5 ml of dimethylformamide was added. The mixture was reacted at room temperature for 2 hours and, at the end of this time, it was concentrated by IR$\nu_{max}^{KBr}$ (cm$^{-1}$) : 1640, 1600.

EXAMPLE 77

To a solution of 472 mg of benzhydryl 2-phthalylaminoethyl ether in ethanol (65 ml) was added 132 mg of 80% aqueous solution of hydrazine hydrate, of hydrazine hydrate, and the mixture was heated and refluxed for 1.5 hours. The reaction mixture was concentrated by evaporation under reduced pressure and the residue was suspended in 20 ml of dry tetrahydrofuram. To the suspension was added 371.3 mg of N-3-(3,4-dimethoxyphenyl)-2-propenoylthiazolidine-2-thione, and the mixture was stirred at room temperature for 13 hours under argon atmosphere. The reaction mixture was concentrated by evaporation under reduced pressure, 2N aqueous sclution of sodium hydroxide was added to the residue, and the mixture was extracted with chloroform. The organic layer was concentrated by evaporation under reduced pressure and the residue was subjected to silica gel column chromatography. There was obtained from fractions eluted with chloroform 465 mg of 2-[3-(3,4-dimethoxyphenyl)-2-propenoyl]aminoethyl benzhydryl ether. Spectrophotometric data of the product support the structure shown below.

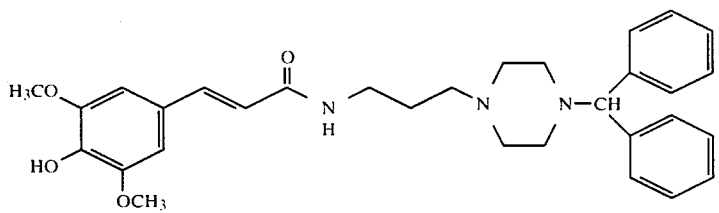

$^1$H-NMR (CDCl$_3$)δ(ppm): 3.55 (4H, m), 3.80 (6H, m), 5.32 (1H, s), 6.33 (1H, b (J=15.5 Hz)), 6.63 (1H, bs), 6.67–7.27 (12H, m), 7.53 (1H d (J=15.5Hz).

IRν$_{max}$$^{KBr}$ (cm$^{-1}$) : 3250, 1650, 1508, 1270.

EXAMPLE 78

To a solution of 0.50 g of N-benzhydryl-N'-4-phthalylaminobutylpiperazine in ethanol (10 ml) was added 137.8 mg of 80% aqueous solution of hydrazine hydrate, and the mixture was heated and refluxed for 2.5 hours under argon atmosphere. The reaction mixture was filtered and the filtrate was concentrated by evaporation under reduced pressure. To the residue was added dry tetrahydrofuran (5 ml) to give a suspension, to which a solution of 500.8 mg of N-3-(3,5-dimethoxy-4-β-methoxyethoxymethoxy) phenyl-2-propenoyl-thiazolidine-2-thione in dry tetrahydrofuran (5 ml) was added, and then the mixture was stirred, under argon atmosphere, at room temperature for 22 hours. The reaction mixture was concentrated by evaporation under reduced pressure and the residue was subjected to silica gel column chromatography. There was obtained from fractions eluted with chloroform - methanol (50 : 1, 20 : 1) 549.2 mg of N-benzhydryl-N'-3-(3,5-dimethoxy-4-β-methoxyethoxymethoxymethoxy) phenyl-2-propenoylaminobutylpiperazine. To a solution of 549.2 mg of the amide compound in methanol (815 ml) was added 253.6 mg of p-toluenesulfonic acid monohydrate, and the mixture was heated and refluxed for 1.2 hours. The reaction mixture was concentrated by evaporation under reduced pressure, a saturated aqueous solution of sodium hydrogencarbonate was added to the residue, and the mixture was extracted with chloroform. The organic layer was concentrated by evaporation under reduced pressure and the residue was subjected to silica gel column chromatography. There was obtained from fractions eluted with chloroform - methanol (50 : 1, 20 : 1) 463.8 mg of N-benzyhdryl-N'-3-(3,5-dimethoxy-4-hydroxy)phenyl-2-propenoylaminobutylpiperazine. Spectrophotometric data of the product support the structure shown below.

$^1$H-NMR (CDCl$_3$)δ(ppm) 1.50 (4H m) 2.43 (10H m) 3.67 (6H, s), 4.12 (1H, s), , 6.27 (2H, m), 6.28 (1H, d (J=15.5Hz)), 6.60 (2H, s), 6.83–7.63 (11H, m).

IRν$_{max}$$^{KBr}$(cm$^{-1}$) 3200, 2880, 2760, 1660, 1600.

EXAMPLE 79

To a solution of 424 mg (1.43 mmol) of N-(2-benzhydroxyethyl) piperazine in dry dimethylformamide (2 ml) was added 475 mg (1.15 mmol) of N-[3-[3,5-dimethoxy-4-(β-methoxyethoxymethoxy) phenyl]-2-propenoyl]thiazolidine-2-thione, and the mixture was reacted at room temperature for 2 hours under argon atmosphere. The reaction mixture was concentrated by evaporation under reduced pressure and the residue was subjected to silica gel column chromatography, eluted with chloroform-methanol (100 : 1), to give 588 mg (0.995 mmol) of N-[3[3,5-dimethoxy-4-(β-methoxyethoxymethoxy)phenyl]-2-propenoyl]-N'-(2-benzhydroxyethyl) piperazine.

To a solution of 588 mg (0.995 mmol) of the amide compound in methanol (10 ml) was added 190 mg (0.999 mmol) of p-toluenesulfonic acid monohydrate, and the mixture was refluxed for 1 hour. The reaction mixture was diluted with water and adjusted to a pH value of 10 by the addition of aqueous solution of sodium carbonate and then extracted with ethyl acetate. The organic layer was washed with water and concentrated by evaporation under reduced pressure, The residue was subjected to Sephadex column chromatography, eluted with methanol, to give 375 mg (0.746 mmol) of N-[3-(3,5-dimethoxy-4-hydroxyphenyl) -2-propenoyl]-N'-(2-benzhydroxyethyl) piperazine. Spectrophotometric data of the product support the structure shown below.

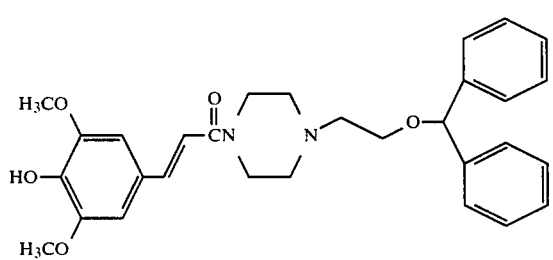

IRν$_{max}$$^{KBr}$ (cm$^{-1}$) : 3350, 1650, 1610. $^1$H-NMR (deutero methanol)δ: 2.53 (6H, m), 3.67 (6H, m), 3.83 (3H, s), 5.33 (1H, s), 6.62–7.70 (14H, m).

EXAMPLE 80

To a solution of 160 mg (0.52 mmol) of N-(3-benzhydroxypropyl) piperazine in dry tetrahydrofuran (5 ml) was added a solution of 206 mg (0.5 mmol) of N-[3-(3,5- dimethoxy-4-(β-methoxyethoxymethoxy) (3,5-dimethoxy-4(β-methoxyethoxymethoxy) phenyl-2-propenoyl]thiazolidine-2-thione in dry tetrahydrofuran, and the mixture was allowed to react at room temperature overnitht. The reaction mixture was concentrated by evaporation under reduced pressure, diluted with chloroform and washed, in turn, with 2N aqueous solution of sodium hydroxide and water. The organic layer was dried over anhydrous sodium sulfate and concentrated by evaporation under reduced pressure. The residue was subjected to silica gel column chromatography, eluted with chloroform - methanol (50 : 1), to give 270 mg (0.45 mmol) of N-[3-[3,5-dimethoxy-4-(β-methoxyethoxymethoxy) phenyl]-2-propenoyl]-N'-(3-benzhydroxypropyl)piperazine.

To a solution of 270 mg (0.45 mmol) of the amide compound in 5 ml of methanol was added 95 mg (0.5 mmol) of p-toluen esulfonic acid monohydrate,,and the mixture was heated and refluxed for 1 hour under argon atmosphere. The reaction mixture was concentrated by evaporation under reduced pressure, a saturated aqueous solution of sodium hydrcgencarbonate was added to the residue, and extracted with ethyl acetate. The organic layer was dried over anhydrous sodium sulfate and concentrated by evaporation under reduced pressure. The residue was subjected tc silica gel column chromatography, eluted with chlcroform - methanol, to give 200 mg (0.38 mmol) of N-[3-(3,5-dimethoxy-4-hydroxyphenyl) 2-propenoyl]-N'-(3-benzhydroxypropyl)piperazine. Spectrophotometric data of the product support the structure shown below.

4-(β-methoxyethoxymethoxy) phenyl]-2-propenoyl]-2-propenoyl]aminoethyl benzhydryl ether.

To a solution of 350 mg (0.67 mmol) of the amide compound in methanol (10 ml) was added 20 mg (0.1 mmol) of p-toluenesulfonic acid monohydrate, and the mixture was heated and refluxed for 1 hour. A saturated aqueous solution of sodium hydrogencarbonate was added to the reaction mixture, which was then extracted with ethyl acetate. The organic layer was concentrated by evaporation under reduced pressure and the residue was subjected to silica gel column chromatography. There was obtained from fractions eluted with chloroform - methanol (50 : 1) 182 mg (0.42 mmol) of 2-[3-(3,5-dimethoxy-4-hydroxy]phenyl-2-propenoyl) aminoethyl benzhydryl ether.

Spectrophotometric data of the product support the structure shown below.

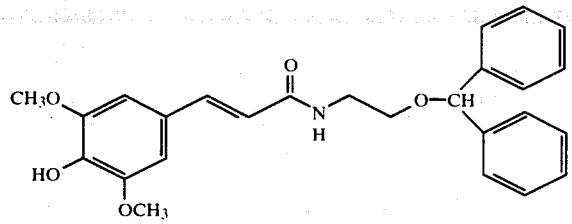

$IR\nu_{max}^{KBr}$ (cm$^{-1}$): 3400, 1660, 1600

EXAMPLE 82

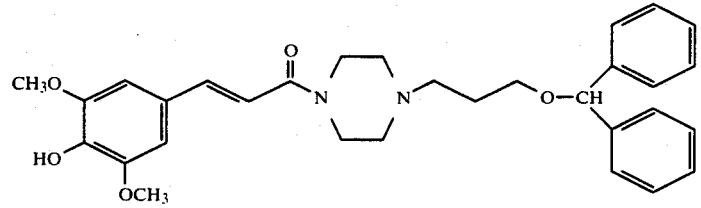

$IR\nu_{max}^{KBr}$ (cm$^{-1}$): 3400, 1642, 1600.

$^1$H-NMR (deutero methanol)δ: 1.80 (2H, m), 2.40 (6H, m), 3,67 (6H, m), 3.80 (6H, s), 5.28 (1H, s), 6.7–7.7 (14H, m).

EXAMPLE 81

To a solution of 247 mg (1 mmol) of benzhydryl 2-phthalylaminoethyl ether in ethanol (10 ml) was added 125 mg (2 mmol) of 80% aqueous solution of of hydrazine hydrate, and the mixture was refluxed for 2 hours. The reaction mixture was concentrated by evaporation under reduced pressure and the residue was suspended in 10 ml of dry tetrahydrofuran. To the suspension was added 495 mg (1.2 mmol) of N-[3-[3,5-dimethoxy-4-(β-methoxyethoxy methoxy)phenyl]-2-propenoyl]thiazolidine-2-thione, in dry tetrahydrofuran (10 ml), and the mixture was reacted at room temperature for 18 hours. The reaction mixture was concentrated by evaporation under reduced pressure, diluted with chloroform and washed with 2N aqueous solution of sodium hydroxide. The organic layer was concentrated by evaporation under reduced pressure and the residue was subjected to silica gel column chromatography. There was obtained from fractions eluted with chloroform 350 mg (0.67 mmol) of 2-[3-[3,5-dimethoxy- To a solution of 555 mg (1.14 mmol) of N-(p-chlorobenzhydryl)-N'-(4-phthalylaminobutyl) piperazine in ethanol (5 ml) was added 85 mg (1.36 mmol) of 80% hydrazine hydrate, and the mixture was heated and refluxed for 2 hours under argon atmosphere. The reaction mixture was concentrated by evaporation under reduced pressure and the residue was dissolved in 2 ml of dry dimethylformamide. To the solution was added a solution of 685 mg (1.2 mmol) of N-[5-(3,4-di-β-methoxyethoxymethoxy)phenyl-2,4-pentadienoyl]-thiazolid in dry dimethylformamide (2 ml), and the mixture was reacted at room temperature for 3 hours. The reaction mixture was concentrated by evaporation under reduced pressure and the residue was subjected to silica gel column chromatography. There was obtained from fractions eluted with chloroform - methanol (50 : 1) 563 mg (0.78 mmol) of N-(p-chlorobenzhydryl)-N'-[4-[5-[3,4-di-(β-methoxyethoxymethoxy) phenyl]-2,4-pentadienoyl]aminobutyl]piperazine.

To a solution of 563 mg (0.78 mmol) of the amide compound in methanol (10 ml) was added 152 mg (0.8 mmol) of p-toluenesulfonic acid monohydrate, and the mixture was heated and refluxed for 2 hours. The reaction mixture was concentrated by evaporation under reduced pressure, water was added to the residue, and the mixture was adjusted to a pH value of 10 by the addition of an aqueous solution of sodium carbonate. The mixture was extracted with chlorofcrm and the organic layer was concentrated by evaporation under reduced pressure. The residue was subjected to Sephadex LH-20 column chromatography, eluted with methanol, to give 284 mg (0.52 mmol) of N-(p-chlorobenzhydryl)-N'-[4-[5-(3,4-dihydreoxyphenyl) -2,4-pentadienoyl]aminobutyl]piperazine. Spectrophotometric data of the product support the structure shown below.

centrated by evaporation under reduced pressure and the residue was subjected to silica gel column chromatography. There was obtained from fractions eluted with, chloroform - methanol (10:1) 334.0 mg N-benzhydryl-N'-5-(3,4-dihydroxyphenyl)-2,4-pentadienoylaminobutylpiperazine.

Spectrophotometric data of the product support the structure shown below.

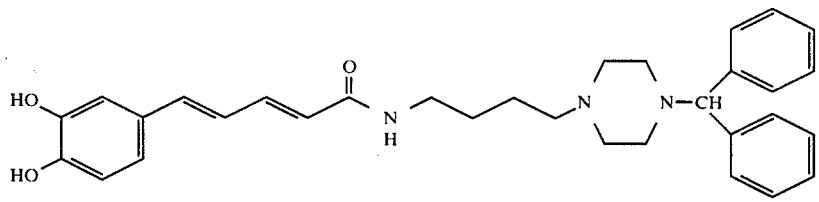

$^1$H-NMR (CDCl$_3$)δ(ppm):
1.48 (4H, m), 2.42 (10H, m), 4.17 (1H, s), 5.98 (1H, d (J=15.5 Hz)), 6.52–7.50 (16H, m).

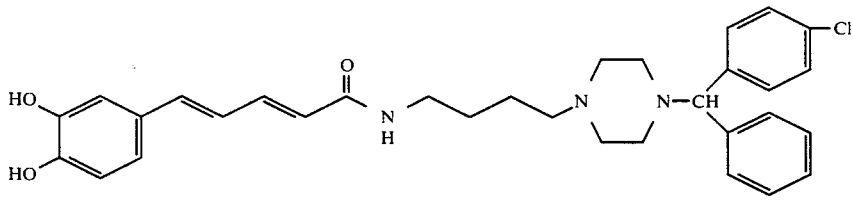

IRν$_{max}$$^{KBr}$ (cm$^{-1}$) : 3300,. 1660, 1600.

IRν$_{max}$ $^{KBr}$ (cm$^{-1}$): 2880, 1760, 1655, 1600.

EXAMPLE 83

To a solution of 0.05 g of N-benzhydryl-N'-(4-phthalylaminobutyl) piperazine in ethanol (10 ml) was added 137.8 mg of 80% aqueous solution of hydrazine hydrate, and the mixture was heated and refluxed for 2.5 hours under argon atmosphere. The reaction mixture was filtered and the filtrate was concentrated by evaporation under reduced pressure. The residue was suspended in dry tetrahydrofuran (5 ml), a solution of 571.1 mg of N-[5-(3,4-di-β-methoxyethoxymethoxy)phenyl-2,4-pentadienoyl)-thiazolidine-2-thione in dry tetrahydrofuran (5 ml) was added, and the mixture was stirred at room temperature for 20 hours under argon atmosphere. The reaction mixture was concentrated by evaporation under reduced pressure and diluted with chloroform. The mixture was filtered and the filtrate was concentrated by evaporation under reduced pressure. The residue was subjected to silica gel column chromatography, eluted with chloroform - methanol (70:1–50:1), to give 622.6 mg of N-benzhydryl-N'-5-(3,4-di-β-methoxyethoxymethoxy)phenyl -2,4-pentadienoylaminobutylpiperazine.

To a solution of 622.6 mg of the amide compound in methanol (15 ml) was added 392.5 mg of p-toluenesulfonic acid monohydrate, and the mixture was heated and refluxed for 1 hour. The reaction mixture was concentrated by evaporation under reduced pressure, a saturated aqueous solution of sodium hydrogencarbonate was added to the residue, and the mixture was extracted with chloroform. The organic layer was con-

EXAMPLE 84

To a solution of 690 mg (2.33 mmol) of N-(2- benzhydroxyethyl)piperazine in dry dimethylformamide (2 ml) was added 1.75 g (3.26 mmol) of N-[5-[3,4-bis(βmethoxyethoxymethoxy)phenyl]-2,4-pentadienoyl]thiazolidine-2-thione, and the mixture was reacted at room temperature 18 hours under argon atmosphere. The reaction mixture was concentrated by evaporation under reduced pressure and the residue was subjected to silica gel column chromatography. There was obtained from fractions eluted with chloroform - methanol (100:1) 856 mg (1.30 mmol) of N-[5-[3,4-bis(β-methoxyethoxymethoxy)phenyl]-2,4-pentadienoyl]-N'-(2-benzhydroxyethyl)piperazine. To a solution of 856 mg (1.30 mmol) of the amide compound in methanol (17 ml) was added 257 mg (1.35 mmol) of p-toluenesulfonic acid monohydrate, and the mixture was refluxed for 4 hours. A saturated aqueous solution of sodium chloride was added to the reaction mixture, which was adjusted to a pH value of 10 by the addition of an aqueous solution of sodium carbonate, and then extracted with ethyl acetate. The organic layer was washed with water and concentrated by evaporation under reduced pressure. The residue was subjected to Sephadex column chromatography, eluted with methanol, to give 439 mg (0.906 mmol) of N-[5-(3,4-dihydroxyphenyl)-2,4-pentadienoyl]--N'-(2-benzhydroxyethyl)piperazine. Spectrophotometric data of the product support the structure shown below.

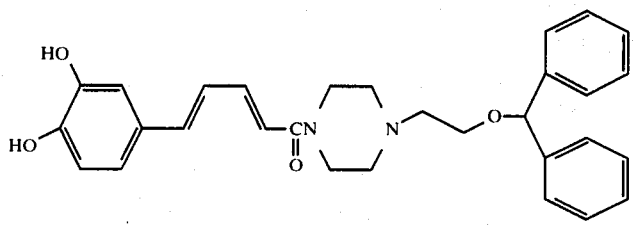

IR$\nu_{max}^{KBr}$ (cm$^{-1}$): 3200, 1640, 1610, 1590.
$^1$H-NMR (deutero methanol) δ: 2.43 (6H, m), 3.52 (6H, m), 5.30 (1H, s), 6.35 (1H, d, J=15 Hz), 6.67-7.57 (16H, m).

EXAMPLE 85

To a solution of 650 mg (1.2 mmol) of N-(3-benzhydroxypropyl)piperazine in dry tetrahydrofuran (5 ml) was added a solution of 966 mg (2.0 mmol) of N-[5-[3,4-di(β-methoxyethoxymethoxy)phenyl]2,4-pentadienoyl]thiazolidine-2-thione in dry tetrahydrofuran (6 ml), and the mixture was reacted at room temperature for 14 hours. The reaction mixture was concentrated by evaporation under reduced pressure, diluted with chloroform and washed, in turn, with 2N aqueous solution of sodium hydroxide and water. The organic layer was dried over anhydrous sodium sulfate and concentrated by evaporation under reduced pressure. The residue was subjected to silica gel column chromatography, eluted with 1% methanol in chloroform, to give 1.09 g (1.6 mmol) of N-[5-[3,4-di(β-methoxyethoxy)phenyl)-2,4-pentadienoyl]-N'-(3-benzhydroxypropyl)piperazine.

A solution of 901 mg (1.33 mmol) of the amide compound in methanol was added, under argon atmosphere, 279 mg (1.47 mmol) of p-toluenesulfonic acid monohydrate, and the mixture was refluxed for 1.5 hours. The reaction mixture was concentrated by evaporation under reduced pressure, a saturated aqueous solution of sodium hydrogencarbonate was added to the residue, and then the mixture was extracted with ethyl acetate. The organic layer dried over anhydrous sodium sulfate and concentrated by evaporation under reduced pressure. The residue was subjected to silica gel column chromatography, eluted with 5% methanol in chloroform, to give 330 mg (0.66 mmol) of N-[5,[3,4-hydroxyphenyl]-2,4-pentadienoyl]-N'-(3-benzhydroxypropyl)-piperazine.

Spectrophotometric data of the product support the structure shown below.

$^1$H-NMR [deutero chloroform-deutero pyridine (1:1)]δ: 1.50-2.05 (2H, m), 2.10-2.67 (6H, m), 3.30 -3.80 (6H, m), 5.30 (1H, s), 6.30 (1H, d, J=15Hz), 6.50-7.50 (1H, m).

EXAMPLE 86

To a solution of 527 mg (1.08 mmol) of N-(p-chlorobenzhydryl) -N'-(4-phthalylaminobutyl)piperazine in 95% ethanol (10.5 ml) was added 82 mg (1.31 mmol) of 80% aqueous solution of of hydrazine hydrate, and the mixture was refluxed for 3 hours under argon atmosphere.

The reaction mixture was concentrated by evaporation under reduced pressure and dry dimethylformamide (2 ml) was added to the residue. To the mixture was added a solution of 475 mg (1.16 mmol) of N-[5-[3-methoxy-4-(β- methoxyethoxymethoxy)phenyl]-2,4-pentadienoyl]thiazolidine-2-thione in dry dimethylformamide (2 ml), and the whole mixture was reacted at room temperature for 4 hours. The reaction mixture was concentrated by evaporation under reduced pressure and the residue was subjected to silica gel column chromatography. There was obtained from fractions eluted with chloroform-methanol (50:1) 464 mg (0.716 mmol) of N-(p-chlorobenzhydryl) -N'-[4-[5-[3-methoxy-4-(β-methoxyethoxymethoxy)phenyl]-2,4-pentadienoyl]aminopropyl]piperazine.

To a solution of 464 mg (0.716 mmol) of the amide compound in methanol (10 ml) was added 137 mg (0.720 mmol) of p-toluenesulfonic acid monohydrate, and the mixture was refluxed for 2 hours. The reaction mixture was concentrated by evaporation under reduced pressure, water was added to the residue, and the mixture was adjusted to a pH value of 10 by the addition of an aqueous solution of sodium carbonate. The mixture was extracted with chloroform and the organic layer was concentrated by evaporation under reduced pressure. The residue was subjected to Sephadex column chromatography, eluted with methanol, to give 289 mg (0.516 mmol) of N-(p-chlorobenzhydryl)-N'-[4-[5-(3-

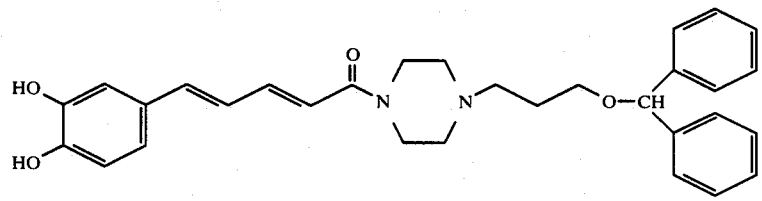

IR$\nu_{max}^{KBr}$ (cm$^{-1}$): 3190, 1630, 1565.

methoxy-4-hydroxy)phenyl]-2,4-pentadienoyl-]aminobutyl]piperazine. Spectrophotometric data of the product support the structure shown below.

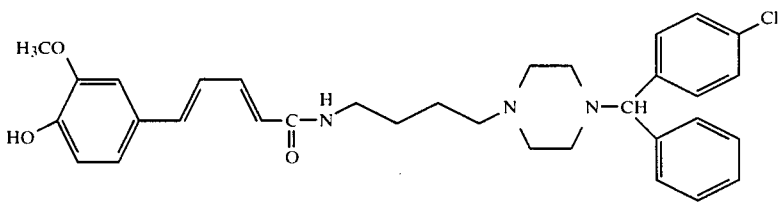

IR$\nu_{max}^{KBr}$ (cm$^{-1}$):3220, 1660, 1600.

$^1$H-NMR (deutero chloroform)δ: 1.55 (4H, bs), 2.45 (10H, bs), 3.32 (2H, bs), 3.83 (3H, s), 4.17 (1H, bs), 5.83 (1H, d, J=15 Hz), 6.50–7.53 (15H, m).

EXAMPLE 87

To a solution of 500 mg (1.1 mmol) of N-benzhydryl-N'-(4-phthalylaminobutyl)piperazine in ethanol (10 ml) was added 128 mg (2.21 mmol) of 80% aqueous solution of hydrazine hydrate, and the mixture was heated and refluxed for 2.5 hours under argon atmosphere. The reaction mixture was filtered, the filtrate was concentrated by evaporation under reduced pressure, and 5 ml of dry tetrahydrofuran was added to the residue. To the resulting solution was added a solution of 475 mg (1.16 mmol) of N-[5-[3-methoxy-4-(β-methoxyethoxymethoxy)phenyl]-2,4-pentadienoyl]thiazolidine-2-thione in dry tetrahydrofuran (6 ml), and the mixture was reacted at room temperature overnight. The solvent was distilled off under reduced pressure and the residue was subjected to silica gel column chromatography. There was obtained from fractions eluted with chloroform-methanol (50:1) 450 mg (0.73 mmol) of N-benzhydryl-N'-[4-[5-[3-methoxy-4-(β-methoxyethoxymethoxy)phenyl]-2,4-pentadienoyl]aminopropyl]piperazine.

To a solution of 450 mg (0.73 mmol) of the amide compound in methanol (10 ml) was added 152 mg (0.8 mmol) of p-toluenesulfonic acid monohydrate, and the mixture was heated and refluxed for 2 hours. The reaction mixture was concentrated by evaporation under reduced pressure, water was added to the residue, and the mixture was adjusted to a pH value of 10 by the addition of an aqueous solution of sodium carbonate. The mixture was extracted with chloroform and the extract was concentrated by evaporation under reduced pressure. The residue was subjected to Sephadex LH-20 column chromatography, eluted with methanol, to give 236 mg (0.45 mmol) of N-benzhydryl-N'-[4-[5-(3-methoxy-4-hydroxyphenyl)-2,4-pentadienoyl]aminobutyl]piperzine, Spectrophotometric data of the product support the structure shown below.

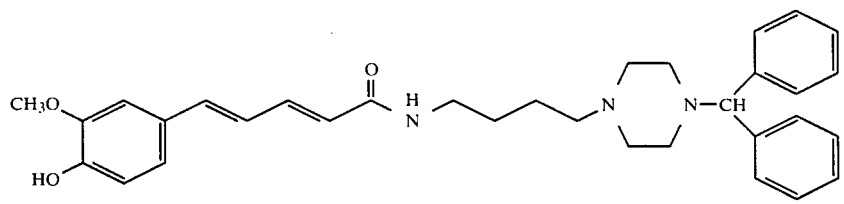

IR$\nu_{max}^{KBr}$ (cm$^{-1}$):3300, 1655, 1600.

EXAMPLE 88

To a solution of 706 mg (2 mmol) of 7-(2-phthalylaminoethyl)theopylline in 50 ml of ethanol was added 500 mg (8 mmol) of 80% hydrazine hydrate, and the mixture was refluxed for 2 hours under argon atmosphere. To the reaction mixture was added 100 ml of n-butanol and the mixture was allowed to cool. Crystals precipitated were filtered and the filtrate was concentrated by evaporation under reduced pressure. The residue was dissolved in 10 ml of dimethylformamide, a solution of 820 mg (2 mmol) of N-[5-(3-methoxy-4-β-methoxyethoxymethoxyphenyl)-2,4-pentadienoyl]-thiazolidine-2-thione in dimethylformamide (5 ml) was added, and the mixture was reacted at room temperature for 2 hours. The reaction mixture was concentrated by evaporation under reduced pressure and the residue was subjected to silica gel column chromatography, eluted with chloroform-methanol (50:1), to give 660 mg (1.28 mmol) of 7-[2-[5-(3-methoxy-4-β-methoxyethoxymethoxyphenl)-2,4-pentadienoyl]aminoethyl]theopylline.

To a solution of 660 mg (1.28 mmol) of the amide compound in 50 ml of methanol was added 500 mg (2.63 mmol) of p-toluenesulfonic acid monohydrate, and the mixture was refluxed for 39 minutes. After allowing the reaction mixture to cool, a saturated aqueous solution of of sodium hydrogencarbonate was added to adjust the pH value at 10, and the water was added to give crystals. These crystals were collected by filtration and recrystallized form methanol, affording 340 mg (0.80 mmol) of of 7-[2-[4-(3-methoxy-4-hydroxyphenyl)-2,4-pentadienoyl]aminoethyl]theophylline.

Spectrophotometric data of the product support the structure shown below.

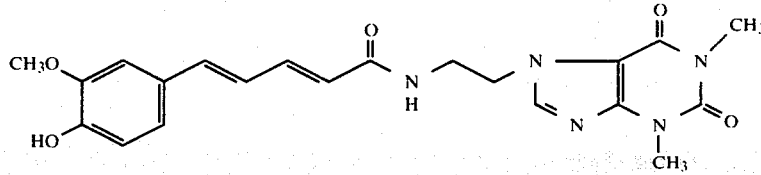

$^1$H-NMR (d$_6$-DMSO)δ: 3.23 (3H, s), 3.42 (3H, s), 3.62 (2H, m), 3.80 (3H, s), 4.35 (2H, m), 5.92 (1H, d, J=15 Hz), 6.56–7.28 (6H, m), 7.86 (1H, s), 7.98 (1H, t, J=4 Hz), 9.17 (1H, s).

IRν$_{max}^{KBr}$ (cm$^{-1}$): 3302, 1710, 1660, 1650, 1610.

EXAMPLE 89

To a mixture of 261 mg (0.88 mmol) of N-(2-benzhydroxyethyl)piperazine in dry dimethylformamide (5 ml) was added 480 mg (1.17 mmol) of N-[5-[3-methoxy-4-(β-methoxyethoxymethoxy)phenyl]-2,4-pentadienoyl]-thiazolidine-2-thione, and the mixture was reacted at room temperature for 19 hours under argon atmosphere. The reaction mixture was concentrated by evaporation under reduced pressure and the residue was subjected to silica gel column chroxtography. There was obtained from fractions eluted with chloroform-methanol (100:1) 515 mg (0.878 mmol) of N-[5-[3-methoxy-4-(β-methoxyethoxymethoxy)phenyl]-2,4-pentadienoyl]-N′-(2-benzhydroxyethyl)piperazine. To a solution of 515 mg (0.878 mmol) of the amide compound in methanol (10 ml) was added 178 mg (0.936 mmol) of p-toluenesulfonic acid monohydrate, and the mixture was refluxed for 1 hour. The reaction mixture was concentrated by evaporation under reduced pressure, water was added to the residue and the mixture was adjusted to a pH value of 10 by the addition of an aqueous solution of sodium hydrogencarbonate.

The mixture was extracted with ethyl acetate and the organic layer was washed with water and concentrated by evaporation under reduced pressure. The residue was subjected to Sephadex column chromatography, eluted with methanol, to give 386 mg (0.774 mmol) of N-[5-(3-methoxy-4-hydroxyphenyl)-2,4-pentadienoyl]-N′-(2-benzhydroxyethyl)piperazine. Spectrophotometric data of the product support the structure shown below.

$^1$ H-NMR (deutero chloroform)δ: 2.57 (6H, m), 3.58 (6H, m), 3.83 (3H, m), 5.30 (1H, s), 6.32 (1H, d; J=15 Hz), 6.63–7.60 (16H, m).

EXAMPLE 90

To a solution of 650 mg (2.1 mmol) of N-(3-benzhydroxypropyl)piperazine in dry tetrahydrofuran (5 ml) was added a solution of 818 mg (2.1 mmol) of N-[5-[3methoxy-4-(β-methoxyethoxymethoxy)phenyl]-2,4-pentadienoyl]thiazolidihe-2-thione in dry tetrahydrofuran (6 ml) and the mixture was reacteed at room temperature for 14 hours. The reaction mixture was concentrated by evaporation under reduced pressure and the residue was diluted with chloroform. The mixture was washed, in turn, with 2N aqueous solution of sodium hydroxide and water and the organic layer was dried over anhydrous sodium sulfate and then concentrated by evaporation under reduced pressure. The residue was subjected to silica gel column chromatography, eluted with 1% methanol in chloroform, to give 1.106 g (1.8 mmol) of N-[5-[3-methoxy-4-(β-methoxyethoxymethoxy)phenyl]-2,4-pentadienoyl]-N′-(3-benzhydroxypropyl)piperazine. To a solution of 1.064 (2.1 mmol) of the amide compound in methanol (10 ml) was added 370 mg (1.95 mmol) of p-toluenesulfonic acid monohydrate, and the mixture was refluxed for 1.5 hous under argon atmosphere. The mixture was concentrated by evaporation under reduced pressure, diluted with chloroform and washed, in turn, with a saturated aqueous solution of sodium hydrogencarbonate and water. The organic layer was dried over anhydrous sodium sulfate and concentrated by evaporation under reduced pressure. The residue was subjected to silica gel column chromatography, eluted with a 1 to 2% methanol in chloroform, to give 730 mg (1.42 mmol) of N-[5-(3-methoxy-4-hydroxyphenyl)-2,4-pentadienoyl]-N′-(3-benzhydroxypropyl)piperazine.

Spectrophotometric data of the product support the structure shown below.

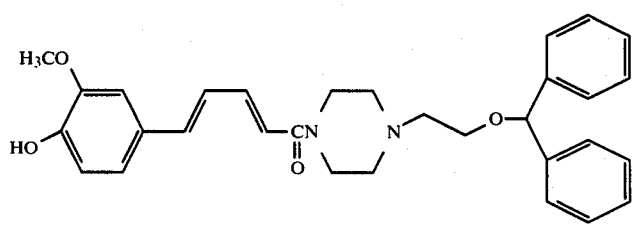

IRν$_{max}^{KBr}$ (cm$^{-1}$): 3350, 1640, 1585

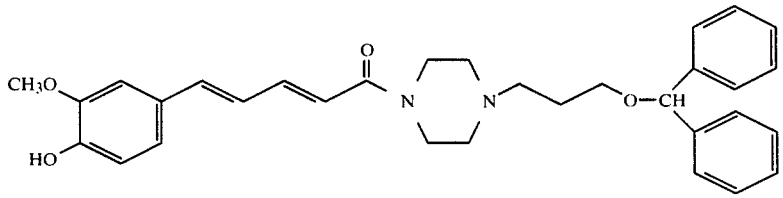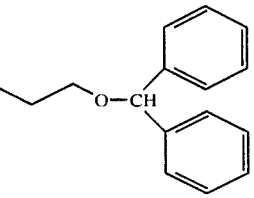

IR$\nu_{max}^{KBr}$ (cm$^{-1}$): 1635, 1580

$^1$H-NMR (deutero chloroform)δ: 1.50–2.10 (2H, m), 2.20–2.66 (6H, m), 3.31–3.73 (6H, m), 3.82 (3H, s), 5.27 (1H, s), 6.30 (1H, d, J=16 Hz), 6.52–7.70 (16H, m).

EXAMPLE 91

To a solution of 697 mg of benzhydryl 2-phthalylaminoethyl ether in methanol (10 ml) was added 195 mg of 80% aqueous solution of hydrazine hydrate, and the mixture was heated under reflux for 1.5 hours. The reaction mixture was concentrated by evaporation under reduced pressure and the residue was suspended in 20 ml of dry tetrahydrofuran. To the suspension was added 533 mg of N-5-(3-methoxy-4-β-methoxyethoxymethoxy)phenyl-2,4-pentadienoyl-thiazolidine-2-thione, and the mixture was stirred at room temperature for 18 hours under argon atmosphere. The reaction mixture was concentrated by evaporation under reduced pressure, 2N aqueous solution of sodium hydroxide was added to the residue, and the mixture was extracted with chloroform. The organic layer was concentrated by evaporation under reduced pressure and the residue was subjected to silica gel column chromatography. There was obtained from fractions eluted with chloroform 623 mg of 2-[5-(3-methoxy-4-β-methoxyethoxymethoxy)phenyl-2,4-pentadienoyl]aminoethyl benzhydryl ether.

To a solution of 620 mg of the amide compound in methanol (15 ml) was added 23 mg of p-toluenesulfonic acid monohydrate, and the mixture was heated under refluxed for 1 hour. A saturated aqueous solution of sodium hydrogencarbonate was added to the reaction mixture, which was then extracted with ethyl acetate. The residue was subjected to silica gel column chromatography. There was obtained from fractions eluted with chloroform-methanol (100:1) 342.3 mg of 2-[5-(3-methoxy -4-hydroxy)phenyl-2,4-pentadienoyl]aminoethyl benzhydryl ether. Spectrophotometric data of the product support the structure shown below.

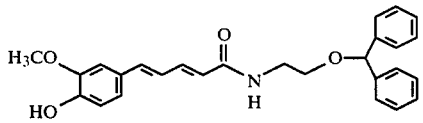

$^1$H-NMR (CDCl$_3$) δ (ppm): 3.55 (4H, m), 3.77 (6H, s), 5.32 (1H, s), 5.89 (1H, d (J=15 Hz)), 6.40 (1H, bs), 6.53–7.77 (17H, m).

IR$\nu_{max}^{KBr}$ (cm$^{-1}$): 3300, 1650, 1585, 1508, 1280.

EXAMPLE 92

To a solution of 371 mg (1 mmol) of benzhydryl 3-phthalaminoethyl ether in ehtanol (10 ml) was added 125 (2 mmol) of 80% aqueous solution of hydrazine hydrate, and the mixture was heated under refluxed for 2 hours under argon atmosphere. The reaction mixture was concentrated by evaporation under reduced pressure and the residue was suspended in 10 ml of dry tetrahydrofuran. To the suspension was added a solution of 490 mg (1.2 mmol) of N-[5-[3-methoxy-4-(β-methoxyethoxymethoxy)phenyl]-2,4-pentadienoyl]-thiazolidine-2-thione in dry tetrahydrofuran (10 ml), and the mixture was reacted at room temperature for 18 hours under argon atmosphere. The reaction mixture was concentrated by evaporation under reduced pressure, chloroform was added to the residue, and the mixture was washed with 2N aqueous solution of sodium hydroxide. The organic layer was concentrated by evaporation under reduced pressure and the residue was subjected to silica gel column chromatography. There was obtained from fractions eluted with chloroform 362 mg (0.68 mmol) of 3-[5-[3-methoxy-4-(β-methoxyethoxymethoxy)phenyl]-2,4-pentadienoyl-]aminopropyl benzhydryl ether.

To a solution of 362 mg (0.68 mmol) of the amide compound in methanol (10 ml) was added 19 mg (0.1 mmol) of p-toluenesulfonic acid monohydrate, and the mixture was heated under reflux for 1 hour. A saturated aqueous solution of sodium hydrogencarbonate was added to the reaction mixture, which was then extracted with ethyl acetate. The organic layer was concentrated by evaporation under reduced pressure and the residue was subjected to silica gel column chromatography. There was obtained from fraction eluted with chloroform-methanol (50:1) 200 mg (0.45 mmol) of 3-[5-[3-methoxy-4-hydroxyphenyl)-2,4-pentadienoyl-]aminopropyl benzhydryl ether. Spectrophotometric data of the product support the structure shown below.

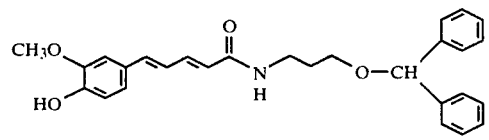

IR$\nu_{max}^{KBr}$ (cm$^{-1}$): 3300, 1660, 1610.

EXAMPLE 93

To a solution of 500 mg (1.10 mmol) of of N-benzhydryl-N'-(4-phthalylaminobutyl)piperazine in ethanol (10 ml) was added 138 mg (2.21 mmol) of 80% hydrazine hydrate, and the mixture was heated under refluxe for 3 hours under argon atmosphere. The reaction mixture was filtered and the filtrate was concentrated by evaporation under reduced pressure. The residue was dissolved in 5 ml of dry tetrahydrofuran, a solution of 402 mg (1.2 mmol) of N-[5-(3,4-dimethoxyphenyl)-2,4-pentadienoyl]thiazolidine-2-thione in dry tetrahydrofuran (6 ml) was added, and the mixture was allowed to react at room temperature for overnight. The reaction mixture was concentrated by evaporation under reduced pressure and the residue was subjected to silica gel column chromatography. There was obtained from fractions eluted with chloroform-methanol (50:1) 460 mg (0.85 mmol) of N-benzhydryl-N'-[4-[5-(3,4-dimethoxyphenyl)-2,4-pentadienoyl]aminobutyl])piperazine.

Spectrophotometric data of the product support the structure shown below:

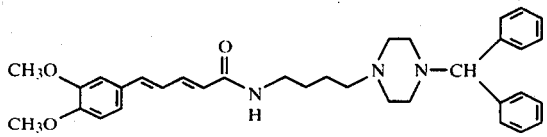

IR$\nu_{max}^{KBr}$(cm$^{-1}$): 1660, 1600.

EXAMPLE 94

To a solution of 310 mg (1 mmol) of N-(3-benzhydroxypropyl)piperazine in dry tetrahydrofuran (5 ml) was added a solution of 483 mg (1 mmol) of N-[5-(3,4-dimethoxyphenyl)-2,4-pentadienoyl]thiazolidine-2-thione in dry tetrahydrofuran (5 ml), and the mixture was allowed to react at room temperature for overnight under argon atmosphere. The reaction mixture was concentrated by evaporation under reduced pressure, diluted with chloroform and washed; in turn, with 2N aqueous solution of sodium hydroxide and water. The organic layer was dried over anhydrous sodium sulfate and concentrated by evaporation under reduced pressure. The residue was subjected to silica gel column chromatography, eluted with chloroform-methanol (50:1), to give 470 mg (0.89 mmol) of N-[5-(3,4-dimethoxyphenyl)-2,4-pentadienoyl]-N'-(3-benzhydroxypropyl)piperazine. Spectrophotometric data of the product support the structure shown below.

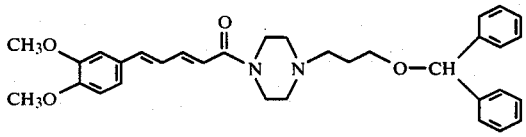

IR$\nu_{max}^{KBr}$ (cm$^{-1}$): 1635, 1575.

EXAMPLE 95

To a suspension of 176 mg (0.5 mmol) of 7-(2-phthalylaminoethyl)theophylline in 20 ml of ethanol was added 125 mg (2 mmol) of 80% hydrazine hydrate, and the mixture was heated under reflux for 2 hours under argon atmosphere. To the reaction mixture was added 25 ml of n-butanol and, after cooling, crystals precipitated were filtered off. The filtrate was concentrated by evaporation under reduced pressure and the residue was dissolved in 3 ml of dimethylformamide. To the solution was added a 183 mg (0.5 mmol) of N-(5-(3,4,5-trimethoxyphenyl)-2,4-pentadienoyl)thiazolidine-2-thione, and the mixture was reacted at room temperature for 2 hours. The reaction mixture was concentrated by evaporation under reduced pressure and the residue was subjected to silica gel column chromatography.

There was obtained from fractions eluted with chloroform-methanol (50:1) 210 mg (0.45 mmol) of 7-[2-[5-(3,4,5-trimethoxyphenyl)-2,4-penta product support the structure shown below.

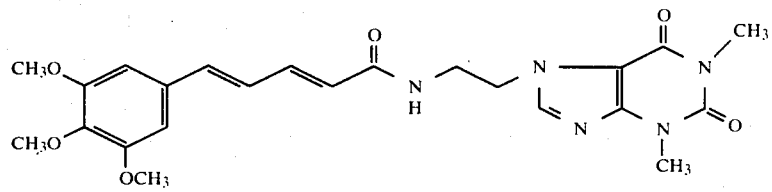

$^1$H-NMR (deutero methanol) δ: 3.25 (3H, s), 3.40 (3H, s), 3.72 (3H, s), 3.80 (6H, s), 3.75 (2H, m), 4.38 (2H, m), 5.91 (1H, d, J=14 Hz), 6.50–7.30 (5H, m), 7.70 (1H, s).
IR$\nu_{max}^{KBr}$ (cm$^{-1}$): 3260, 1702, 1665, 1610.

EXAMPLE 96

To a solution of 550 mg of N-(p-chlorobenzhydryl)-N'-4-phthalylaminbutylpiperazine in ethanol (5 ml) was added 85 mg of 80% aqueous solution of of hydrazine hydrate, and the mixture was heated under reflux for 3 hours under argon atmosphere. The reaction mixture was concentrated by evaporation under reduced pressure and the residue was dissolved in dry dimethylformamide (20 ml). To the solution was added 594.4 mg of N-5-(3,5-dimethoxy-4-β-methoxyethoxymethoxy)phenyl-2,4-pentadienoylthiazolidine-2-thione, and the mixture was allowed to react at room temperature for 16 hours under argon atmosphere. The reaction mixture was concentrated by evaporation under reduced pressure and the residue was subjected to silica gel column chromatography, eluted with chloroform-methanol (50:1), to give 346.8 mg of N-p-chlorobenzhydryl-N'-5-(3,5-dimethoxy-4-β-methoxyethoxymethoxy)phenyl-2,4-pentadienoyl-aminobutylpiperazine. To a solution of 346.8 mg of the amide compound in methanol (15 ml) was added 205.4 mg of p-toluenesulfornic acid monohydrate, and the mixture was heated under reflux for 1.5 hours. The reaction mixture was concentrated by evaporation under reduced pressure, a saturated aqueous solution of sodium hydrogencarbonate was added to the residue, and the mixture was extracted with ethyl acetate. The organic layer was concentrated by evaporation under reduced pressure and the residue was subjected to silica gel column chromatography.

There was obtained from fractions eluted with chloroform-methanol (50:1, 30:1) 304.0 mg of N-p-chlorobenzhydryl-N'-5-(3,5-dimethoxy-4-hydroxy)phenyl-2,4-pentadienlylaminobutylpiperazine. Spectrophotometric data of the product support the structure shown below.

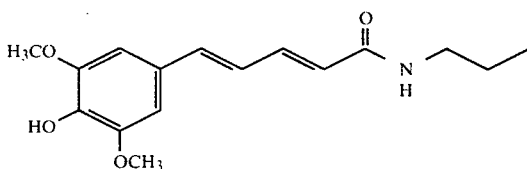
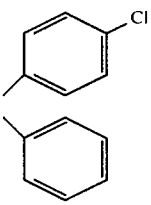

¹H-NMR (CDCl₃) δ: 1.53 (4H, m), 2.42 (1H, m), 3.30 (2H, m), 3.83 (6H, s), 4.15 (1H, s), 4.33 (2H, bs), 5.86 (1H, d (J=15 Hz)), 6.62 (4H, m), 7.23 (10H, m).

IR$\nu_{max}^{KBr}$ (cm⁻¹): 3220, 2880, 2760, 1650, 1620, 1518.

EXAMPLE 97

To a solution of 500 mg (1.10 mmol) of N-benzhydryl-N'-(4-phthalylaminobutyl)piperazine in ethanol (10 ml) was added 138 mg (2.21 mmol) of 80% hydrazine hydrate, and the mixture was heated under reflux for 3 hours under argon atmosphere. The reaction mixture was filtered and the filtrate was concentrated by evaporation under reduced pressure to leave residue, which was dissolved in 5 ml of dry tetrahydrofuran. To the solution was added a sclution of 527 mg (1.2 mmol) of N-[5-(3,5-dimethoxy-4-β-methoxyethoxymethoxy)phenyl-2,4-pentadienoyl]thiazolidine-2-thione, and the mixture was allowed to react at room temperature overnight. The reaction mixture was concentrated by evaporation under reduced pressure and the residue was subjected to silica gel column chromatography, eluted with chloroform-methanol (50:1), to give 580 mg (0.90 mmol) of N-benzhydryl-N'-[4-[5-(3,5-dimethoxy-4-β-methoxyethoxymethoxy)phenyl-2,4-pentadienoyl-]aminobutyl]piperizine. To a solution of 580 mg (0.90 mmol) of the amide compound in methanol (10 ml) was added 380 mg (2.0 mmol) of p-toluenesulfonic acid monohydrate, and the mixture was heated under reflux for 1 hour. The reaction mixture was concentrated by evaporation under reduced pressure, water was added to the residue, and then the mixture was adjusted to a pH value of 10 by the addition of a saturated aqueous solution of sodium carbonate. The mixture was extracted with chloroform and the organic layer was concentrated by evaporation under reduced pressure.

The residue wa subjected to Sephadex LH-20 column chromatography, eluted with methanol, to give 420 mg (0.75 mmol) of N-benzhydryl-N'-[4-[5-(3,5-dimethoxy-4-hydroxy)phenyl-2,4-pentadienoyl]aminobutyl]Spectrophotometric data of the product support the structure shown below.

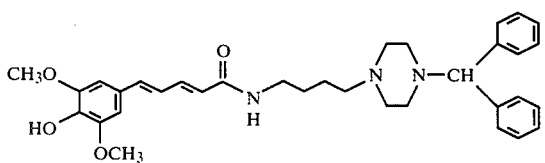

IR$\nu_{max}^{KBr}$ (cm⁻¹): 3220, 1660, 1600.

EXAMPLE 98

To a solution of 794 mg (2.68 mmol) of N-(2-benzhydroxyethyl)piperazine in dry dimethylformamide (4 ml) was added, under argon atmosphere, a solution of 1.15 g (2.61 mmol) of N[5-[3,5-dimethoxy-4-(β-methoxyethoxymethoxy)phenyl]-2,4-pentadienoyl)thiazolidine in dry dimethylformamide (4 ml), and the mixture was allowed to react at room temperature for 17 hours. At the end of this time, the reaction mixture was concentrated by evaporation under reduced pressure and the residue was subjected to silica gel column chromatography, eluted with chloroform-methanol (100:1), to give 413 mg (0.670 mmol) of N-[5-[3,5-dimethoxy-4-(β-methoxyethoxymethoxy)phenyl]-2,4-pentadienoyl]-N'-(2-benzhydroxyethyl)piperazine.

To a solution of 413 mg (0.670 mmol) of of the amide compound in methanol (10 ml) was added 148 mg (0.778 mmol) of p-toluenesulfonic acid monohydrate, and the mixture was refluxed for 1 hour. A saturated aqueous solution of sodium chloride was added to the reaction mixture, which was adjusted to a pH value of 10 by the addition of an aqueous solution of sodium carbonate, and then extracted with ethyl acetate. The organic layer was washed with water and concentrated by evaporation under reduced pressure. The residue was subjected to Sephadex column chromatography, eluted with methanol, to give 194 mg (0.367 mmol) of N-[5-(3,5-dimethoxy-4-hydroxyphenyl)-2,4-pentadienoyl)-N'-(2-benzhydroxyethyl)piperazine. Spectrophotometric data of the product support the structure shown below.

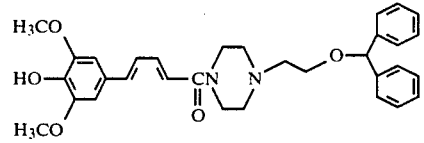

IR$\nu_{max}^{KBr}$ (cm⁻¹): 3300, 1640, 1620, 1590.

¹H-NMR (deutero methanol) δ: 2.50 (6H, m), 3.53 (6H, m), 3.80 (3H, s), 5.33 (1H, s), 6.42 (1H, d, J=14 Hz), 6.75–7.42 (15H, m).

EXAMPLE 99

To a solution of 310 mg (1 mmol) of N-(3-benzhydroxypropyl)piperazine in dry tetrahydrofuran (5 ml) was added, under argon atmosphere, a solution of 440 mg (1 mmol) of N-[5-[3,5-dimethoxy-4-(β-methoxyethoxymethoxy)phenyl]-2,4-pentadienoyl]thiazolidine-2-thione in dry tetrahydrofuran (5 ml), and the mixture was allowed to react at room temperature overnight. The reaction mixture was concentrated by evaporation under reduced pressure, diluted with chloroform, and washed, in turn, with 2N aqueous solution of sodium hydroxide and water. The organic layer was dried over anhydrous sodium sulfate and concentrated by evaporation under reduced pressure. The residue was subjected to silica gel column chromatography, eluted with chloroform-methanol (50:1), to give 540 mg (0.85 mmol) of N-[5-[3,5-dimethoxy -(β-methoxyethoxymethoxy)-phenyl]-2,4-pentadienoyl]-N'-(3-benzhydroxypropyl)-piperazine.

To a solution of 540 mg (0.85 mmol) of the amide compound in 10 ml of methanol was added 190 mg (1 mmol) of p-toluenesulfonic acid monohydrate and, under argon atmosphere, the mixture was heated under reflux for 1 hour. The reaction mixture was concentrated by evaporation under reduced pressure, a saturated aqueous solution of sodium hydrogencarbonate was added to the residue, and the mixture was extracted with ethyl acetate. The organic layer was dried over anhydrous sodium sulfate and concentrated by evaporation under reduced pressure. The residue was subjected to silica gel column chromatography, eluted with chloroform-methanol (20:1), to give 350 mg (0.65 mmol) of N-[5- (3,5-dimethoxy-4-hydroxyphenyl)-2,4-pentadienoyl[-N∝ of the product support the structure shown below.

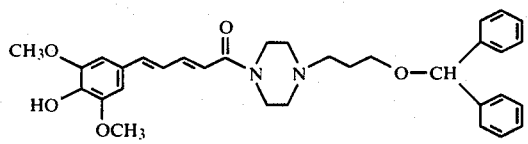

IR$\nu_{max}^{KBr}$ (cm$^{-1}$): 3300, 1640, 1600.

EXAMPLE 100

To a solution of 440 mg of benzhydryl 2-phthalylaminoethyl ether in ethanol (6 ml) was added 123.2 mg of 80% aqueous solution of hydrazine hydrate, and the mixture was heated under reflux for 1.5 hours. The reaction mixture was concentrated by evaporation under reduced pressure and the residue was suspended in 20 ml of dry tetrahydrofuran. To the suspension was added 491 mg of N-5-(3,5-dimethoxy-4-β-methoxyethoxymethoxy)phenyl-2,4 -pentadienoylthiazolidine-2-thione and, under argon atmosphere, the mixture was stirred at room temperature for 18 hours. The reaction mixture was concentrated by evaporation under reduced pressure, 2N aqueous solution of sodium hydroxide was added to the residue, and then the mixture was extracted with chloroform. The organic layer was concentrated by evaporation under reduced pressure and the residue was subjected to silica gel column chromatography. There was obtained from fractions eluted with chloroform-methanol (50:1) 593 mg of 2-[5-(3,5-dimethoxy-4-β-methoxyethoxymethoxy)phenyl-2,4-pentadienoyl]aminoethyl benzhydryl ether. To a solution of 590 mg of the amide compound in methanol (20 ml) was added 41 mg of p-toluenesulfonic acid monohydrate, and the mixture was heated under reflux for 1 hour. A saturated aqueous solution of sodium hydrogencarbonate was added to the reaction mixture, which was extracted with ethyl acetate. The residue was subjected to silica gel column chromatography, eluted with chloroform-methanol (50:1), to give 249 mg of 2-[5-(3,5-dimethoxy-4-hydroxy)phenyl-2,4-pentadienoyl]aminoethyl benzhydryl ether. Spectrophotometric data of the product support the structure shown below.

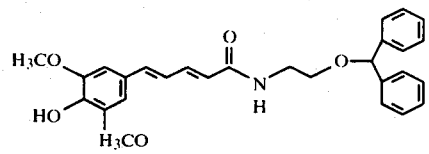

$^1$H-NMR (CDCl$_3$) δ (ppm): 3.57 (4H, m), 3.83 (6H, s), 5.32 (1H, s), 6.23 (1H, d (J=15 Hz)), 6.60–6.75 (3H, m), 7.10–7.63 (11H, m).

IR$\nu_{max}^{KBr}$ (cm$^{-1}$) : 3300, 1650, 1610, 1508, 1340, 1110.

EXAMPLE 101

To 37 ml of a 2M solution of phenylmagnesium bromide in tetrahydrofuran was added, under argon atmosphere, 5.24 g (33.9 mmol) of p-chloroacetophenone, and the mixture was allowed to react at 0° C. for 3 hours. At the completion of this reaction, a saturated aqueous solution of ammonium chloride was added to the reaction mixture, which was then extracted with chloroform. The organic layer was washed with water and then concentrated by evaporation under reduced pressure. The residue was subjected to silica gel column chromatography, eluted with chloroform, to give 6.99 g (30.0 mmol) of 1-phenyl-1-(p-chlorophenyl)ethanol. To a solution of 6.99 g (30.0 mmol) of the alcohol compound in ethanol (80 ml) was added 5.00 ml (93.8 mmol) of conc. sulfuric acid, and the mixture was reacted for 1 hour.

Water was added to the reaction mixture, which was extracted with chloroform. The organic layer was washed with water and concentrated by evaporation under reduced pressure.

The residue was subjected to silica gel column chromatography, affording 6.14 g (28.6 mmol) of 1-phenyl-1-(p-chlorophenyl)ethylene. To a solution of 1.87 g (8.70 mmol) of the ethylene compound in 3-chloropropanol (21 ml) was added 7.04 g (22.1 mmol) of mercuric acetate and, under argon atmosphere, the mixture was reacted at room temperature for 27 hours.

To the reaction mixture was added 45 ml of 3.4N aqueous solution of potassium hydroxide, followed by 831 mg (22.0 mmol) of sodium borohydride in small portions. The mixture was allowed to react at room temperature for 2 hours, after which it was extracted with benzene. The organic layer was washed with water and concentrated by evaporation under reduced pressure.

The residue was subjected to silica gel column chromatography, eluted with chloroform-hexane (1:1), to give 2.32 g (7.50 mmol) of 1-phenyl-1-(p-chlorophenyl)ethyl 3-chloropropyl ether. To 2.32 g (7.50 mmol) of the ether compound was added 2.50 ml (17.1 mmol) of ethyl N-piperazinocarboxylate, and the mixture was reacted at 150° C. for 2 hours. Water was added to the reaction mixture, which was adjusted to a pH value of 11 by the addition of an aqueous solution of sodium carbonate and then extracted with chloroform. The organic layer was washed with water and concentrated by evaporation under reduced pressure. The residue was subjected to silica gel column chromatography, eluted with chloroform, to give 3.23 g (7.50 mmol) of N-[3-[1-phenyl-1-(p-chlorophenyl)ethoxy]propyl]-N'-(eth To a solution of 3.23 g (7.50 mmol) of the amine compound in ethanol (12 ml) and water (6 ml) was added 9.34 g (166 mmol) of potassium hydroxide, and the mixture was refluxed for 25 hours. Water was added to the reaction mixture, which was then extracted with n-butanol. The organic layer was washed with water and concentrated by evaporation under reduced pressure. The residue was subjected to Sephadex column chromatography, eluted with methanol, to give 2.36 g (6.58 mmol) of N-[3-[1-phenyl-1-(p-chlorophenyl)ethoxy]propyl]piperazine.

To a solution of 400 g of the piperazine compound in dry tetrahydrofuran (5 ml) was added a solution of 510 mg of N-[3-[3,4-di-(p-methoxyethoxymethoxy)phenyl]-2-propenoyl]thiazolidine-2-thione in dry tetrahydrofuran (10 ml) and, under argon atmosphere, the mixture was allowed to react at room temperature for 2 hours. The reaction mixture was concentrated by evaporation under reduced pressure, 2N aqueous solution of sodium hydroxide was added to the residue, and the mixture was extracted with chloroform. The organic layer concentrated by evaporation under reduced pressure and the residue was subjected to silica gel column chromatography. There was obtained from fractions eluted with chloroform-methanol (50:1) 335 mg of N-[3-[3,4-di-(β-methoxyethoxymethoxy)phenyl-2-propenoyl]-N'-[3-1-phenyl-1-(p-chlorophenyl)ethoxy]propyl]piperazine.

To a solution of 335 mg of the amide compoun in methanol (10 ml) was added 186 mg of p-toluenesulfonic acid monohydrate, and the mixture was stirred at room temperature for 1.7 hours. A saturated aqueous solution of sodium hydrogencarbonate was added to the reaction mixture, which was then extracted with ethyl acetate. The solvent was distilled off under reduced pressure and the residue was subjected to silica gel column chromatography. There was obtained from fractions eluted with chloroform-methanol (20:1) 50 mg of N-[3-(3,4-dihydroxyphenyl)-2-propenoyl]-N'-[3-[1-phenyl-1-(p-chlorophenyl)ethoxy]propyl]piperazine. Spectrophotometric data of the product support the structure shown below.

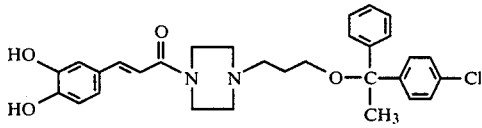

IR$\nu_{max}^{KBr}$ (cm$^{-1}$): 3400, 1935, 1635, 1580.

EXAMPLE 102

To a solution of 1.11 g (5.18 mmol) of 1-phenyl-1-(p-chlorophenyl)ethylene in 2-chloroethanol (10 ml) wa added, under argon atmosphere, 4.04 g (12.7 mmol) of mercuric acetate, and the mixture was reacted at room temperature for 29 hours. To the reaction mixture was added 25 ml of 3.4N aqueous solution of potassium hydroxide, followed by 592 mg (15.7 mmol) of sodium borohydride in small portions.

The mixture was allowed to react at room temperature for 30 minutes and then extracted with benzene. The organic layer was washed with water and concentrated by evaporation under reduced pressure. The residue was subjected tosilica gel column chromatography, eluted with chloroform-hexane (1:1), to give 1.39 g (4.72) of 1-phenyl-1-(p-chlorophenyl)ethyl 2-chloroethyl ether. A mixture of 848 mg (2.87 mmol) of the ether compound and 1.00 ml (6.83 mmol) of of ethyl N-piperazinocarboxylate was reacted at 150° C. for 2 hours. Water was added to the reaction mixture, which was adjusted to a pH value of 11 by the addition of an aqueous solution of sodium carbonate, and then extracted with chloroform. The crganic layer was washed with water and concentrated by evaporation under reduced pressure. The residue was subjected to silica gel column chromatography, eluted with chloroform-methanol (100:1), to give 1.19 g (2.85 mmol) of N-[2-[1-phenyl-1-(p-chlorophenoxy)ethoxy]ethyl]-N'-(ethoxycarbonyl)piperazine.

To a solution of 1.19 g (2.85 mmol) of the amine compound in ethanol (4 ml) and water (2 ml) was added 3.37 g (60.1 mmol) of potassium hydroxide, and the mixture was refluxed for 42 hours. Water was added to the reaction mixture, after whgich it was extracted with n-butanol. The organic layer was was washed with water and concentrated by evaporation under reduced pressure. The residue was subjected to Sephadex column chromatography, eluted with methanol, to give 878 mg (2.55 mmol) of N-[2-[1-phenyl-1-(p-chlorophenyl)ethoxy]ethyl]piperazine. To a solution of 293 mg (0.850 mmol) of the piperazine compound in dry dimethylformamide (5 ml) was added under argon atmosphere a solution of 630 mg (1.64 mmol) of N-[3-[3-methoxy-4-(β-methoxyethoxymethoxy)phenyl]-2-propenoyl]thiazolidine in dry dimethylformamide (5 ml) and the mixture was allowed to react at room temperature for 17 hours. The reaction mixture was concentrated by evaporation under reduced pressure and the residue was subjected to silica gel column chromatography, eluted with chloroform-methanol (100:1), to give 486 mg (0.798 mmol) of N-[3-[3-methoxy-4--(β-methoxyethoxymethoxy)phenyl-2-propenoyl]-N'-[2-[1-pheny-1-1-(p-chlorophenyl)ethoxy]ethyl]piperazine.

To a solution of 486 mg (0.789 mmol) of the amide compound in methanol (10 ml) was added 153 (0.804 mmol) of p-toluenesulfonic acid monohydrate, and the mixture was refluxed for 30 minutes. Water was added to the reaction mixture, which was adjusted to a pH value of 11 by the addition of an aqueous solution of sodium carbonate and then extracted with ethyl acetate. The organic layer was was washed with water and concentrated by evaporation under reduced pressure. The residue was subjected to silica gel column chromatography, eluted with chloroform-methanol (50:1), to give 293 mg (0.562 mmol) of N-[3-[3-methoxy-4-hydroxyphenyl)-2-propenoyl]-N'-[2-[1-phenyl-1-(p-chlorophenyl)ethoxy]ethyl]piperazine.

Spectrophotometric data of the product support the structure shown below.

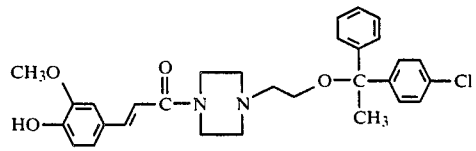

IR$\nu_{max}^{KBr}$ (cm$^{-1}$): 3400, 1642, 1590.
$^1$H-NMR (deutero chloroform) δ: 1.80 (3H, s), 2.3–2.83 (6H, m), 3.17–3.97 (6H, m), 3.80 (3H, s), 6.62 (1H, d, J=15 Hz), 6.88–7.32 (12H, m), 7.55 (1H, d, J=15 Hz).

EXAMPLE 103

After 400 mg (60%, 10 mmol) of sodium hydride had been washed, under argon atmosphere, with dry hexane, it was dissolved in 5 ml of dimethyl sulfoxide. The mixture was stirred at 70°–75° C. for 30 minutes, and then it was cooled to room temperature. To the mixture was added a suspension of 1.8 g (10 mmol) of theophylline in 5 ml of dimethyl sulfoxide, and the whole mixture was stirred for 30 minutes. Further, a solution of 20 g (200 mmol) of 1,2-dichloroethane in 10 ml of dimethyl sulfoxide was added dropwise to the mixture over 15 minutes.

The mixture was stirred at room temperature for a further 16 hours, after which water was added, and then the mixture was extracted with chloroform. The organic layer was dried over anhydrous sodium sulfate and concentrated by evaporation under reduced pressure. The residue was subjected to silica gel column chromatography, eluted with chloroform-methanol (100:1), to give 1.62 g (6.68 mmol) of 7-(2-chloroethyl)-theophylline.

A mixture of 1.00 g (4.66 mmol) of the theophylline derivative and 1.28 g of formylpiperazine was stirred at 80° C. for 13 hours under argon atmosphere. The reaction mixture was subjected to silica gel column chromatography, eluted with chloroform-methanol (20:1), to give 1.38 g (4.65 mmol) of 7-[2-[4-(1 formyl)-piperazine] ethyl]thophylline. 240 mg (0.81 mmol) of the piperazine compound was dissolved, under argon atmosphere, in 10 ml of ethanol, followed by 507 mg (8.1 mmol) of 80% hydrazine hydrate, and then the mixture was heated under reflux for 36 hours. The reaction mixture was allowed to cool to room temperature for and concentrated by evaporation under reduced pressure. The residue was dissolved in 10 ml of dimethylformamide and 330 mg (0.81 mmol) of N-[3-[3-methoxy-4-($\beta$-methoxyethoxymethoxy)-phenyl]-2-propenoyl]-2-thiothiazoline was added to the solution. The mixture was stirred at 80° C. for 1 hour, after which it was concentrated by evaporation under reduced pressure. The residue (450 mg) was subjected to silica gel column chromatography, eluted with chloroform-methanol (100:3), to give 276 mg (0.50 mmol) of 7-[2-[4-[3-[3-methoxy-4-($\beta$-methoxyethoxymethoxy)-phenyl]-2-propenoyl]piperazin-1-yl]-ethyl]theophylline.

To a solution of 276 mg (0.50 mmol) of the theophylline derivative in 10 ml of methanol was added, under argon atmosphere, 242 mg (1.28 mmol) of p-toluenesulfonic acid monohydrate, and the mixture was heated under reflux for 2 hours. The reaction mixture was cooled to room temperature, adjusted to a pH value of 8 by the addition of a saturated aqueous solution of sodium hydrogencarbonate, and then extracted with chloroform.

The organic layer was dried over anhydrous sodium sulfate and concentrate by evaporation under reduced pressure. The residue (200 mg) was subjected to silica gel column chromatography, eluted with chloroform-methanol (50:1), to give 100 mg (0.22 mmol) of 7-[2-[4-[3(3-methoxy-4-hydroxyphenyl)-2-propenoyl]piperazin-1-yl]-ethyl]theophilline. Spectrophotometric data of the product support the structure shown below.

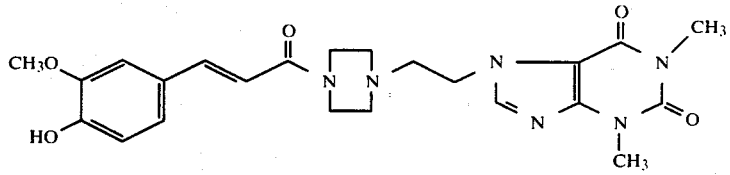

IR$\nu_{max}$ $^{cm}$$_{-1}$ (CHCl$_3$): 3540, 1705, 1660.

$^H$-NMR (deutero chloroform) $\delta$: 2.3–2.8 (4H, m), 2.80 (2H, t, J=6 Hz), 3.3–3.9 (4H, m), 3.39 (3H, s), 3.57 (3H, s), 3.88 (3H, s), 4.40 (2H, t, J=6 Hz), 6.60 (1H, d, J=16 Hz), 6.7–7.3 (3H, m), 7.53 (1H, d, J=16 Hz), 7.58 (1H, s).

EXAMPLE 104

To a solution of 100 mg of N-[3-(3,4-dimethoxy)phenyl-2-propenoyl]thiazolidine-2-thione in dry tetrahydrofuran (5 ml) was added a solution of 115 mg of 1-[3-[1-phenyl-1-(p-chlorophenyl)ethoxy]propyl]piperazine in dry tetrahydrofuran (2 ml), and the mixture was stirred at room temperature for 1.5 hours under argon atmosphere. The reaction mixture was concentrated by evaporation under reduced pressure, 2N aqueous solution of sodium hydroxide was added to the residue, and the mixture was extracted with chloroform.

The organic layer was concentrated by evaporation under reduced pressure and the residue was subjected to silica gel column chromatography. There was obtained from fractions eluted with chloroform-methanol (50:1) 175 mg of N-[3-(3,4-dimethoxy)phenyl-2-propenoyl]-N'-[3-[1-phenyl-1-(p-chlorophenyl)ethoxy]-propyl]piperazine.

Spectrophotometric data of the product support the structure shown below.

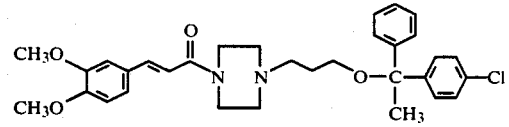

$^1$H-NMR (deutero chloroform) $\delta$ (ppm): 1.83 (3H, s), 1.83 (2H, m), 2.47 (6H, m), 3.27 (2H, t (J=6 Hz)), 3.67 (4H, m), 3.88 (6H, s), 6.73 (1H, d (J=15 Hz)), 7.0–7.43 (12H, m), 7.58 (1H, d (J-15 Hz)).

IR$\nu_{max}$$^{KBr}$ (cm$^{-1}$): 2940, 1645, 1600, 1513.

EXAMPLE 105

To a solution of 343 mg (0.995 mmol) of N-[2-[1-phenyl-1-(p-chlorophenyl)ethoxy]ethyl]piperazine in dry dimethylformamide (3 ml) was added 656 mg (1.59 mmol) of N-[3-[3,5-dimethoxy-4-($\beta$-methoxyethoxymethoxy)phenyl]-2-propenoyl]thiazolidine, and the mixture was allowed to react at room temperature for 16 hours under argon atmosphere.

The reaction mixture was concentrated by evaporation under reduced pressure and the residue was subjected to silica gel column chromatography. There was obtained from fraction eluted with chloroform-methanol (50:1) 412 mg (0.645 mmol) of N-[3-[3,5-dimethoxy-4-($\beta$-methoxyethoxymethoxy)phenyl]-2- propenoyl]-N'-[2-[1-phenyl-1-(p-chlorophenyl)ethoxy]ethyl]piperazine.

To a solution of 412 mg (0.645 mmol) of the amide compound in methanol (8 ml) was added 101 mg (0.531 mmol) of p-toluenesulfonic acid monohydrate, and the mixture was refluxed for 30 minutes. Water was added to the reaction mixture, which was adjusted to a pH value of 11 by the adition of an aqueous solution of sodium carbonate, and then the mixture was extracted with ethyl acetate. The organic layer was washed with water and concentrated by evaporation under reduced pressure. The residue was subjected to silica gel column chromatography, eluted with chloroform-methanol (50:1), to give 371 mg (0.673 mmol) of N-[3-(3,5-dimethoxy-4-hydroxyphenyl)-2-propenoyl]-N'-[2-[1-phenyl-1-(p-chlorophenyl)ethoxy]ethyl]piperazine. Spectrophotometric data of the product support the structure shown below.

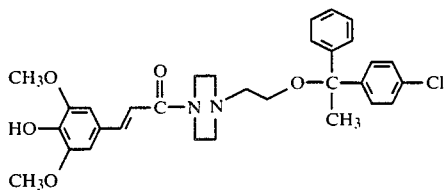

IR$\nu_{max}^{KBr}$ (cm$^{-1}$): 3540, 1647, 1615

$^1$H-NMR (deutero chloroform) δ: 1.80 (3H, s), 2.28–2.78 (6H, m), 3.12–4.02 (6H, m), 3.82 (6H, s), 6.60 (1H, d, J=15 Hz), 6.65 (2H, s), 6.97–7.35 (11H, m), 7.50 (1H, d, J=15 Hz).

EXAMPLE 106

To a solution of 574.8 mg of N-[3-(3,5-dimethoxy-4-β-methoxyethoxymethoxy)phenyl-2-propenoyl]-thiazalidine-2-thione thione in dry tetrahydrofuran (10 ml) was added a solution of 500 mg of 1-[3-[1-phenyl-1-(p-chlorophenyl)ethyl]propyl]piperazine in dry tetrahydrofuran (5 ml), and the mixture was stirred at room temperature for 2 hours under argon atmosphere. The reaction mixture was concentrated by evaporation under reduced pressure, 2N aqueous solution of sodium hydroxide was added to the residue, and the mixture was extracted with chloroform. The organic layer was concentrated by evaporation under reduced pressure and the residue was subjected to silica gel column chromatography. There was obtained from fractions eluted with chloroform-methanol (50:1) 960 mg of N-[3-(3,5-dimethoxy-4-β-methoxyethoxymethoxy)phenyl-2-propenoyl]-N'-[3-[1-phenyl-1-(p-chlorophenyl)ethoxy]-propyl]piperazine.

To a solution of 960 mg of the amide compound in methanol (10 ml) was added 280 mg of p-toluenesulfonic acid monohydrate, and the mixture was heated under reflux for 0.17 hour. A saturated aqueous solution of sodium hydrogencarbonate was added to the reaction mixture, after which it was extracted with ethyl acetate. The solvent was distilled off under reduced pressure and the residue was subjected to silica gel column chromatography. There was obtained from fractions eluted with chloroform-methanol (50:1) 563 mg of N-[3-(3,5-dimethoxy-4-hydroxy)phenyl-2-propenoyl]-N'-[3-[1-phenyl-1-(p-chlorophenyl)ethoxy]-propyl]piperazine.

Spectrophotometric data of the product support the structure shown below.

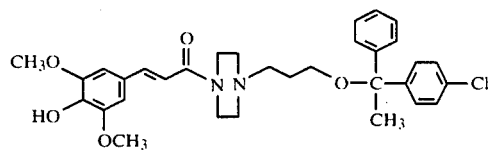

$^1$H-NMR (deutero chloroform) δ(ppm): 1.80 (3H, s), 1.80 (2H, m), 2.43 (6H, m), 3.23 (2H, t (J=6 Hz), 3.63 (4H, m), 3.83 (6H, s), 6.65 (1H, d (J=15 Hz)), 6.70 (2H, s), 7.17–7.33 (10H, m), 7.55 (1H, d (J=15 Hz)).

IR$\nu_{max}^{cm-1}$(KBr): 3420, 2940, 1640, 1600, 1513.

EXAMPLE 107

To a solution of 314 mg (0.910 mmol) of N-[2-[1-phenyl-1-(p-chlorophenyl)ethoxy]ethyl]piperazine in dry dimethylformamide (5 ml) was added 741 (1.53 mmol) of N-[5-[3,4-bis(β-methoxyethoxymethoxy)phenyl]-2,4-pentadienoyl]thiazoline, and the mixture was allowed to react at room temperature for 3 hours under argon atmosphere. The reaction concentrated by evaporation under reduced pressure and the residue was subjected to silica gel column chromatography. There was obtained from fractions eluted with chloroform-methanol (50:1) 620 mg (0.874 mmol) of N-[5-[3,4-bis(β-methoxyethoxymethoxy)phenyl]-2,4-pentadienoyl]-N'-[2-[1-phenyl-1-(p-chlorophenyl)ethoxy]ethyl]piperazine.

To a solution of 620 mg (0.874 mmol) of the amide compound in methanol (7 ml) was added 185 mg (0.973 mmol) of p-toluenesulfonic acid monohydrate, and the mixture was refluxed for 20 minutes. Water was added to the reaction mixture, which was adjusted to a pH value of 11 by the addition of an aqueous solution of sodium carbonate, and then the mixture was extracted with ethyl acetate. The organic layer was washed with water, concentrated by evaporation under reduced pressure and the residue was subjected to silica gel column chromatography. There was obtained from fractions eluted with chloroform-methanol (20:1) 279 mg (0.523 mmol) of N-[5-(3,4-dihydroxyphenyl)-2,4-pentadienoyl]-N-[2-[1-phenyl-1-(p-chlorophenyl)-ethoxy]ethyl]piperazine.

Spectrophotometric data of the product support the structure shown below.

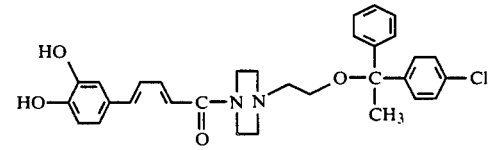

IR$\nu_{max}^{cm-1}$ (KBr): 3300, 1635, 1610, 1580

$^1$H-NMR (deutero chloroform) δ: 1.78 (3H, s), 2.25–2.82 (6H, m), 3.12–3.88 (6H, m), 6.20 (1H, d, J=14 Hz), 6.47–7.62 (15H, m).

EXAMPLE 108

To a solution of 536.8 mg of N-[5-(3,4-di-β-methoxyethoxymethoxy)phenyl-2,4-pentadienoyl]thiazolidine-2-thione in dry tetrahydrofuran (10 ml) was added a solution of 400 mg of 1-[3-[1-phenyl-1-(p-chlorophenyl)ethoxy]-propyl]piperazine in dry tetrahydrofuran (5 ml), and the mixture was stirred at room temperature for 1.5 hours under argon atmosphere. The reaction mixture was concentrated by evaporation under reduced pressure, 2N aqueous solution of sodium hydroxide was added to the residue, and the mixture was extracted with chloroform. The organic layer concentrated by evaporation under reduced pressure and the residue was subjected to silica gel column chromatography. There was obtained from fractions eluted with chloroform-methanol (50:1) 354.5 mg of N-[5-(3,4-di-β-methoxyethoxymethoxy)phenyl-2,4-pentadienoyl]-N'-[3-[1-phenyl-1-(p-chlorophenyl)ethoxy]propyl]piperazine.

To a solution of 354 mg of the amide compound in methanol (10 ml) was added 186 mg of 1-toluenesulfonic acid monohydrate, and the mixture was stirred at room temperature for for 1.7 hours. A saturated aqueous solution of sodium hydrogencarbonate was added to the reaction mixture, which was then ectracted with ethyl acetate. The solvent was distilled off under reduced pressure and the residue was subjected to silica gel column chromatography.

There was obtained from fractions eluted with chloroform-methanol (20:1) 46 mg of N-[5-(3,4-dihydroxy)-phenyl-2,4-pentadienoyl]-N'-[3-[1-phenyl-1-(p-chlorophenyl)ethoxy]propyl]piperazine.

Spectrophotometric data of the product support the structure shown below.

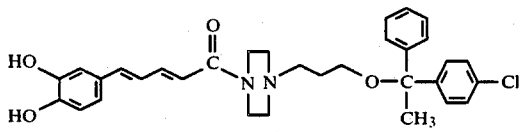

$^1$H-NMR (deutero chloroform) δ(ppm):
1.80 (3H, s), 1.80 (2H, m), 2.42 (6H, m), 3.23 (2H, bt), 3.60 (4H, m), 6.33–7.33 (18H, m).
IR$\nu_{max}^{KBr}$ (cm$^{-1}$): 3400, 2940, 1638, 1580.

EXAMPLE 109

In 3 ml of ethanol was dissolved 690 mg (2.33 mmol) of 7-[2-[4-(1-formyl)piperazine]ethyl]theophylline, under argon atmosphere, then 2.92 g (46.6 mmol) of 80% hydrazine hydrate was added, and the mixture was heated under reflux for 8 hours. The reaction mixture was allowed to cool to room temperature and concentrated by evaporation under reduced pressure. The residue was dissolved in 10 ml of dimethylformamide, 1.13 g (2.33 mmol) of N-[5-[3,4-di(β-methoxyethoxymethoxy)phenyl]-2,4-pentadienoyl]-2-thiothiazoline was added to the solution, and the mixture was stirred at 80° C. for 2 hours. The reaction mixture was concentrated by evaporation under reduced pressure and 2 g of the residue was subjected to silica gel column chromatography. There was obtained from fractions eluted with chloroform-methanol (100:3) 790 mg (1.20 mmol) of 7-[2-[4-[5-[3,4-di(β-methoxyethoxymethoxy)phenyl-2,4-pentadienoyl]piperazin-1-yl]ethyl]theophylline.

To a solution of 790 mg (1.20 mmol) of the theophylline derivative in 12 ml of methanol was added 685 mg (3.6 mmol) of p-toluenesulfonic acid monohydrate, and the mixture was heated under reflux for 2 hours under argon atmosphere. The reaction mixture was allowed to cool to room temperature, adjusted to a pH value of 9 by the addition of a saturated aqueous solution of sodium hydrogencarbonate and extracted with chloroform. The organic layer was dried over anhydrous sodium sulfate and concentrated by evaporation under reduced pressure. The residue (310 mg) was subjected to silica gel column chromatography, eluted with chloroform-methanol (100:9), to give 59 mg (0.12 mmol) of 7-[2-[4-[5-(3,4-dihydroxyphenyl)-2,4-pentadienoyl]piperazin-1-yl]theophylline.

Spectrophotometric data of the product support the structure shown below.

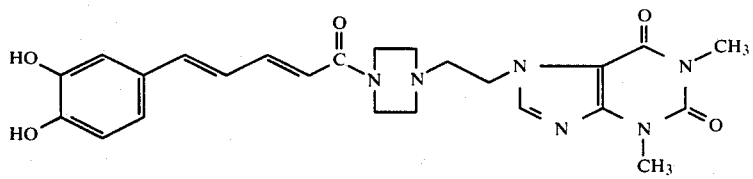

IR $\nu_{max}^{cm-1}$(KBr): 3400, 1705, 1660.
$^1$H-NMR (deutero pyridine) δ: 2.2–2.7 (4H, m), 2.78 (2H, t, J=6 Hz), 3.2–3.8 (4H, m), 3.43 (3H, s), 3.53 (3H, s), 4.50 2H, t, J=6 Hz), 6.5–7.7 (7H, m), 7.50 (1H, s).

EXAMPLE 110

To a solution of 466 mg (1.35 mmol) of N-[2-[1-phenyl-1-(p-chlorophenyl)ethoxy]ethyl]piperazine in dry dimethylformamide (7 ml) was added, under argon atmosphere, 618 mg (1.51 mmol) of N-[5-[3-methoxy-4-(β-methoxyethoxymethoxy)phenyl-2,4-pentadienoyl]-thiazolidine, and the mixture was allowed to react at room temperature for 68 hours, after which it was concentrated by evaporation under reduced pressure. The residue was subjected to silica gel column chromatography, eluted with chloroform-methanol (100:1), to give 736 mg (1.16 mmol) of of N-[5-[3-methoxy-4-(β-methoxyethoxymethoxy)phenyl]-2,4-pentadieoyl]-N'-[2-[1-phenyl-1-(p-chlorophenyl)ethoxy]ethyl]piperazine.

To a solution of 736 mg (1.16 mmol) of the amide compound in methanol (15 ml) was added 225 mg (1.18 mmol) of p-toluenesulfonic acid monohydrate, and the mixture was refluxed for 15 minutes.

Water was added to the reaction mixture, which was adjusted to a pH value of 11 by the addition of an aqueous solution of sodium carbonate, and extracted with ethyl acetate. The organic layer was washed with water and concentrated by evaporation under reduced pressure. The residue was subjected to silica gel column chromatography, eluted with chloroform-methanol (50:1), to give 363 mg (0.664 mmol) of N-[5-(3-methoxy-4-hydroxyphenyl)-2,4-pentadienoyl]-N'-[2-[1-phenyl-1-(p-chlorophenyl)ethoxy]ethyl]piperazine. Spectrophotometric data of the product support the structure shown below.

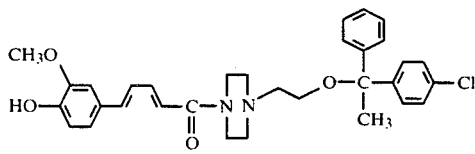

IR $\nu_{max}{}^{cm-1}$ (KBr): 3400, 1635, 1615, 1580.

1H-NMR (deutero chloroform) δ: 1.80 (3H, s), 2.3–2.77 (6H, m), 3.20–3.80 (6H, m), 3.83 (3H, s), 6.32 (1H, d, J=14 Hz), 6.60–7.57 (15H, m).

EXAMPLE 111

To a solution of 553 mg of N-[5-(3-methoxy-4-β-methoxyethoxymethoxy)phenyl-2,4-pentadienoyl]-thiazolidine-2-thione in dry tetrahydrofuran (15 ml) was added a solution of 500 mg of 1-[3-[1-phenyl-1-(p-chlorophenyl)ethoxy]propyl]piperazine in dry tetrahydrofuran (5 ml), and the mixture was stirred at room temperature for 4 hours under argon atmosphere. The reaction mixture was concentrated by evaporation under reduced pressure, 2N aqueous solution of sodium hydroxide was added to the residue, and the mixture was extracted with chloroform. The organic layer was concentrated by evaporation under reduced pressure and the residue was subjected to silica gel column chromatography. There was obtained from fractions eluted with chloroform-methanol (50:1) 900 mg of N-[5-(3-methoxy-4-β-methoxyethoxymethoxy)phenyl-2,4-pentadienoyl]-N'-[3-[1 phenyl-1-(p-chlorophenyl)ethoxy-]propyl]piperazine.

To a solution of 900 mg of the amide compound in methanol (10 ml) was added 263 mg of p-toluenesulfonic acid monohydrate, and the mixture was heated under reflux for 0.17 hour. A saturated aqueous solution of sodium hydrogencarbonate was added to the reaction mixture, which was extracted with ethyl acetate. The solved was distilled off under reduced pressure and the residue was subjected to silica gel column chromatography. There was obtained from fractions eluted with chloroform-methanol (50:1) 328 mg of N-[5-(3-methoxy-4-hydroxy)phenyl-2,4-pentadienoyl]-N'-[3-[1-phenyl-1-(p-chlorophenyl)ethoxy]propyl]piperazine. Spectrophotometric data of the product support the structure shown below.

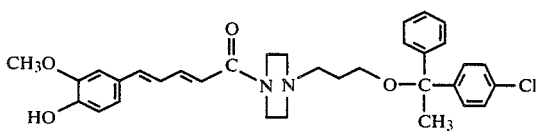

1H-NMR (deutero chloroform) δ(ppm): 1.83 (3H, m), 1.83 (2H, m), 2.45 (6H, m), 3.26 (2H, t (J=6 Hz)), 3.63 (4H, m), 3.87 (3H, s), 6.35 (1H, d (J=15 Hz)), 6.76–7.50 (16H, m).

IR $\nu_{max}{}^{cm-1}$ (KBr): 3400, 2940, 1640, 1580, 1513.

EXAMPLE 112

To 8 ml of ethanol was added, under argon atmosphere, 564 mg (1.90 mmol) of 7-[2-[4-(1formyl)-piperazino]ethyl]theophylline. To a solution was added 596 mg (9.52 mmol) of 80% hydrazine hydrate, and the mixture was heated under reflux for 15 hours. After being allowed to cool to room temperature, the reaction mixture was concentrated by evaporation under reduced pressure. To the residue thus obtained was added 10 ml of dimethylformamide, and 778 mg (1.90 mmol) of N-[5-[3-methoxy-4-(β-methoxyethoxymethoxy)-phenyl]-2,4-pentadienoyl]-2-thiothiazoline was added to the solution. The mixture was stirred at 80° C. for 2 hours, after which it was concentrated by evaporation under reduced pressure. The residue (1.22 g) was subjected to silica gel column chromatography, eluted with chloroform-methanol (100:3), to give 502 mg (0.86 mmol) of 7-[2-[4-[5-[3-methoxy-4-(β-methoxyethoxymethoxy)phenyl]-2, 4-pentadienoyl]piperazin-1-yl]ethyl]theophylline.

To a solution of 502 mg (0.86 mmol) of the theophylline derivative in 8 ml of methanol was added, under argon atmosphere, 360 mg (1.90 mmol) of p-toluenesulfonic acid monohydrate, and the mixture was heated under reflux for 4 hours. The reaction mixture was cooled to room temperature, adjusted to a pH value of 10 by the addition of a saturated aqueous solution of sodium hydrogencarbonate, and then extracted with chloroform. The organic layer was dried over anhydrous sodium sulfate and concentrated by evaporation under reduced pressure. The residue (540 mg) was subjected to silica gel column chromatography, eluted with chloroform-methanol (50:1), to give 225 mg (0.45 mmol) of 7-[2-[4-[5-(3-methoxy-4-hydroxyphenyl)-2,4]-pentadienoyl]piperazin-1-yl]ethyl]theophylline.

Spectrophotometric data of the product support the structure shown below.

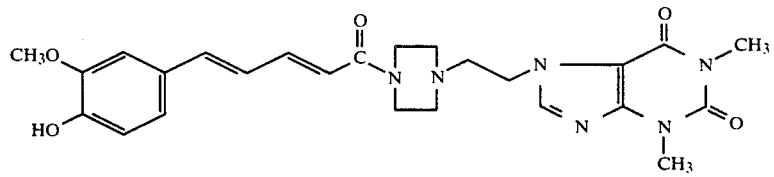

IR $\nu_{max}{}^{cm-1}$ (KBr) 3400, 1700, 1655.

1H-NMR (deutero chloroform) δ: 2.3–3.0 (6H, m), 3.3–3.9 (4H, m), 3.37 (3H, s), 3.55 (3H, s), 3.85 (3H, s), 4.2–4.6 (2H, m), 6.3–7.8 (7H, m), 7.57 (1H, s).

EXAMPLE 113

To a solution of 527 mg (1.53 mmol) of N-[2-[1-phenyl-1-(p-chlorophenyl)ethoxy]ethyl]piperazine in dry dimethylformamide (10 ml) was added, under argon atmosphere, 760 mg (1.73 mmol) of N-[5-[3,5-dimethoxy-4-(β-methoxyethoxymethoxy)phenyl]-2,4-pentadienoyl]thiazolidine, and the mixture was allowed to react at room temperature for 67 hours. The reaction mixture was concentrated by evaporation under reduced pressure and the residue was subjected to silica gel column chromatography, eluted with chloroform-methanol (100:1), to give 618 mg (0.929 mmol) of N-[5-[3,5-dimethoxy-4-(β-methoxyethoxymethoxy)phenyl]-

2,4-pentadienoyl]-N'-[2-[1-phenyl-1-(p-chlorophenyl)ethoxy]ethyl]piperazine.

To a solution of 618 mg (0.929 mmol) of the amide compound in methanol (10 ml) was added 181 (0.952 mmol) of p-toluenesulfonic acid monohydrate, and the mixture was refluxed for 15 hours. Water was added to the reaction mixture, which was adjusted to a pH value of 11 by the addition of an aqueous solution of sodium carbonate, and then extracted with chloroform. The organic layer was washed with water and concentrated by evaporation under reduced pressure. The residue was sujected to silica gel column chromatography, eluted with chloroform-methanol (100:1), to give 422 mg (0.766 mmol) of N-[5-(3,5-dimethoxy-4-hydroxyphenyl]-2,4-pentadienoyl]-N'-[2-[1-phenyl-1-(p-chlorophenyl)ethoxy]ethyl]piperazine. Spectrophotometric data of the product support the structure shown below.

oxy)-phenyl]-2,4-pentadienoyl]piperazin-1-yl]ethyl] theophylline.

To a solution of 394 mg (0.67 mmol) of the theophylline derivative in 12 ml of methanol was added, under argon atmosphere, 320 mg (1.68 mmol) of p-toluenesulfonic acid monohydrate, and the mixture was heated under refluxed for 2 hours, after which it was cooled to room temperature. The reaction mixture was adjusted to a pH value of 8 by the addition of a saturated aqueous solution of sodium hydrogencarbonate, and extracted with chloroform. The organic layer was dried over anhydrous sodium sulfate and concentrated by evaporation under reduced pressure.

The residue (400 mg) was subjected to silica gel column chromatography, eluted with chloroform-methanol (50:1), to give 252 mg (0.48 mmol) of 7-[2-[4-[5-(3,5-dimethoxy-4-hydroxyphenyl)-2,4-pentadienoyl]ethyl]theophylline. Spectrophotometric data of the product support the structure shown below.

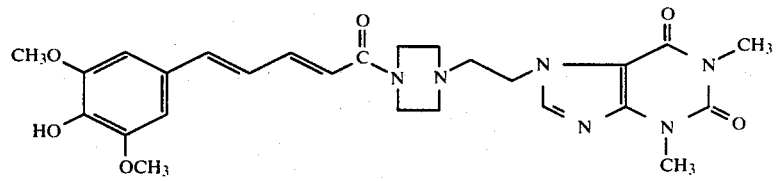

IR $\nu_{max}^{cm-1}$ (chloroform): 3535, 1705, 1660.

$^1$H-NMR (deutero chloroform) δ: 2.4–2.7 (4H, m), 2.80 (2H, t, J=6 Hz), 3.4–3.9 (4H, m), 3.40 (3H, s), 3.58 (3H, s), 3.89 (6H, s), 4.40 (2H, t, J=6 HZ), 6.0–7.5 (6H, m), 7.57 (1H, s).

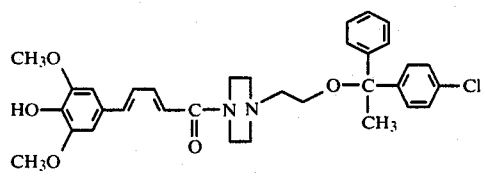

IR $\nu_{max}^{cm-1}$ (KBr): 3400, 1640, 1615, 1585.

$^1$H-NMR (deutero chloroform) δ: 1.85 (3H, s), 2.37–2.83 (6H, m), 3.20–3.93 (6H, m), 3.87 (6H, s), 6.33 (1H, d, J=14 Hz), 6.53–7.67 (14H, m).

EXAMPLE 114

To a solution of 455 mg (1.54 mmol) of 7-[2-[4-(1-formyl)piperazino]ethyl]theophylline in 10 ml of ethanol was added 960 mg (15.4 mmol) of 80% hydrazine hydrate, and the mixture was heated under reflux for 23 hours under argon atmosphere. The reaction mixture was cooled to room temperature and concentrated by evaporation under reduced pressure. Ten (10) ml of dimethylformamide was added to the residue thus obtained. To the solution was added 680 mg (1.45 mmol) of N-[5-[3,5-dimethoxy-4-(β-methoxyethoxymethoxy)-phenyl]-2,4-pentadienoyl]-2-thiothiazoline, and the mixture was stirred at 80° C. for 4 hours. The reaction mixture was concentrated by evaporation under reduced pressure and 1.20 g of the residue was subjected to silica gel column chromatography, eluted with chloroform-methanol (100:3), to give 394 mg (0.76 mmol) of 7-[2-[4-[5-[3,5-dimethoxy-4-(β-methoxyethoxymeth-

EXAMPLE 115

To a solution of 118 mg (0.40 mmol) of 7-[2-[4-(1-formyl)piperazino]ethyl]theophylline in 5 ml of ethanol was added, under argon atmosphere, 250 mg (4.0 mmol) of 80% hydrazine hydrate, and the mixture was heated under reflux for 36 hours, after which it was cooled to room temperature. The reaction mixture was concentrated by evaporation under reduced pressure and 5 ml of dimethylformamide was added to the residue. To the solution was added 153 mg (0.50 mmol) of N-[5-(3,4,5-torimethoxyphenyl)-2,4-pentadienoyl)-2-thiothiazoline, and the mixture was stirred at 80° C. for 1 hour. The reaction mixture was concentrated by evaporation under reduced pressure and the residue was subjected to silica gel column chromatography, eluted with chloroform-methanol (50:1), to give 50 mg (0.09 mmol) of 7-[2-[4-[5-(3,4,5-trimethoxyphenyl)-2,4-pentadienoyl]-piperazin-1-yl]ethyl]theophylline.

Spectrophotometric data of the product support the structure shown below.

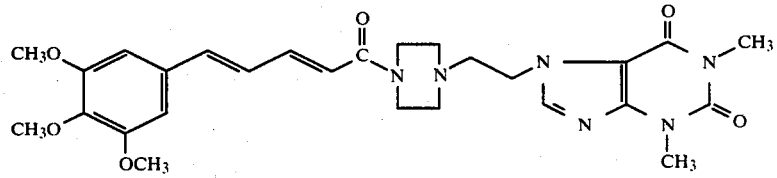

IR $\nu_{max}^{cm-1}$ (chloroform); 1705, 1660

$^1$H-NMR (deutero chloroform) δ: 2.3–2.8 (4H, m), 2.80 (2H, t, J=6 Hz), 3.3–3.9 (4H, m), 3.38 (3H, s), 3.57

(3H, s), 3.84 (9H, s), 4.39 (2H, t, J=6 Hz), 6.0–7.5 (6H, m), 7.58 (1H, s).

EXAMPLE 116

A mixture of 5.71 g (56.5 mmol) of 4-hydroxypiperidine and 5.28 g (20.8 mmol) of N-(2-bromoethyl)phthalimide was reacted at 150° C. for 1 hour under argon atmosphere. The reaction mixture was allowed to cool, water was added, and then the mixture was extracted with chloroform. The organic layer was concentrated by evaporation under reduced pressure and the residue was subjected to silica gel column chromatography, eluted with chloroform-methanol (20:1), to give 3.60 g (13.1 mmol) of 1-(2-phthaloylaminoethyl)-4-hydroxypiperidine.

To 3.60 g (13.1 mmol) of the alcohol compound were added 10 ml (56.3 mmol) of benzhydryl chloride and 3.47 g (25.1 mmol) of potassium carbonate, and the mixture was reacted at 135° C. for 4 hours. Water was added to the reaction mixture, which was then extracted with chloroform. The organic layer was washed with water and concentrated by evaporation under reduced pressure. The residue was subjected to silica gel column chromatography, eluted with chloroform, to give 2.48 g (5.64 mmol) of 1-(2-phthaloylaminoethyl)-4-benzhydroxypiperidine.

To a solution of 224 mg (0.509 mmol) of the piperidine compound in ethanol (5 ml) was added, under argon atmosphere, 50 mg (0.999 mmol) of hydrazine hydrate, and the mixture was refluxed for 1 hour, after which it was concentrated by evaporation under reduced pressure. To the residue was added 2 ml of dry dimethylformamide. A solution of 527 mg (1.37 mmol) of N-[3-[3-methoxy-4-($\beta$-methoxyethoxymethoxy)phenyl]-2-propenoyl]thiazolidine-2-thione in dry dimethylformamide (8 ml) was added to the above solution, and the mixture was allowed to react at room temperature for 14 hours. The reaction mixture was concentrated by evaporation under reduced pressure and the residue was subjected to silica gel column chromatography, eluted with chloroform-methanol (50:1), to give 292 mg (0.508 mmol) of 1-[2-[3-[3-methoxy-4-($\beta$-methoxyethoxymethoxy)phenyl]-2-propenoyl]aminoethyl]-4-benzhydroxypiperidine.

To a solution of 292 mg (0.508 mmol) of the amide compound in methanol (8 ml) was added 112 mg (0.589 mmol) of p-toluenesulfonic acid monohydrate, and the mixture was refluxed for 20 minites. Water was added to the reaction mixture, which was adjusted to a pH value of 11 by the addition of an aqueous solution of sodium carbonate and then extracted with ethyl acetate. The organic layer was washed with water and concentrated by evaporation under reduced pressure. The residue was subjected to silica gel column chromatography, eluted with chloroform-methanol (50:1), to give 164 mg (0.337 mmol) of 1-[2-[3-(3-methoxy-4-hydroxyphenyl)-2-propenoyl]aminoethyl]-4-benzhydroxypiperidine.

Spectrophotometric data of the product support the structure shown below.

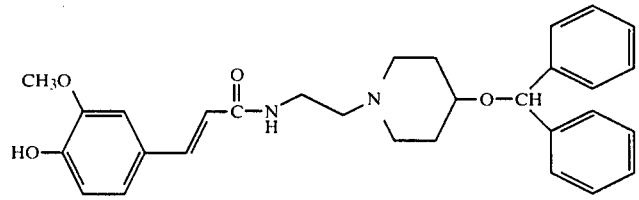

IR $\nu_{max}^{cm-1}$ (KBr): 3300, 1660, 1620, 1600
$^1$H-NMR (deutero chloroform) δ: 1.57–3.0 (10H, m), 3.43 (3H, m), 3.72 (3H, s), 5.42 (1H, s), 5.98 (1H, d, J=15 Hz), 6.38–7.47 (15H, m).

EXAMPLE 117

To a solution of 228 mg (0.518 mmol) of 1-(2-phthaloylaminoethyl)-4-benzhydroxypiperidine in ethanol (5 ml) was added 50 mg (0.999 mmol) of hydrazine hydrate, and the mixture was refluxed for 1 hour under argon atmosphere. The reaction mixture was concentrated by evaporation under reduced pressure and to the residue thus obtained was added 6 ml of dry dimethylformamide. To the solution was added 369 mg (0.892 mmol) of N-[3-[3,5-dimethoxy-4-($\beta$-methoxyethoxymethoxy)phenyl]-2-propenoyl]thiazolidine-2-thione, and the mixture was allowed to react at room temperature for 40 hours. The reaction mixture was concentrated by evaporation under reduced pressure and the residue was subjected to silica gel column chromatography, eluted with chloroform-methanol (50:1), to give 276 mg (0.456 mmol) of 1-[2-[3-[3,5-dimethoxy-4-($\beta$-methoxyethoxymethoxy)phenyl]-2-propenoyl]aminoethyl]-4-benzhydroxypiperidine.

To a solution of 276 mg (0.456 mmol) of the amide compound in methanol (6 ml) was added 79 mg (0.415 mmol) of p-toluenesulfonic acid monohydrate, and the mixture was refluxed for 20 minutes. Water was added to the reaction mixture, which was adjusted to a pH value of 11 by the addition of an aqueous solution of sodium carbonate and then extracted with ethyl acetate. The organic layer was washed with water and concentrated by evaporation under reduced pressure. The residue was subjected to silica gel column chromatography, eluted with chloroform-methanol (20:1), to give 162 mg (0.299 mmol) of 1-[2-[3-(3,5-dimethoxy-4-hydroxyphenyl)-2-propenoyl]aminoethyl]-4-benzhydroxypiperidine.

Spectrophotometric data of the product support the structure shown below.

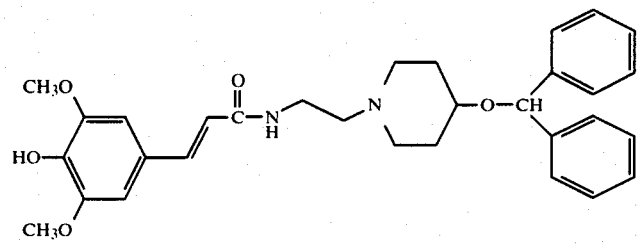

IR $\nu_{max}{}^{cm-1}$ (KBr): 3400, 1660, 1620, 1600

¹H-NMR (deutero chloroform) δ: 1.50–3.03 (10H, m), 3.47 (3H, m), 3.78 (6H, s), 5.38 (1H, s), 5.47 (1H, s), 6.07 (1H, d, J=15 Hz), 6.37–7.50 (14H, m).

EXAMPLE 118

To a solution of 777 mg (1.76 mmol) of 1-(2-phthaloylaminoethyl)-4-benzhydroxypiperidine in ethanol (16 ml) was added 148 mg (2.96 mmol) of hydrazine hydrate, and the mixture was refluxed for 1 hour under argon atmosphere. The reaction mixture was concentrated by evaporation under reduced pressure. To the residue was added 4 ml of dry dimethylformamide, followed by the addition of a solution of 1.33 g (2.75 mmol) of N-[5-[3,4-(β-methoxyethoxymethoxy)phenyl]-2,4-pentadienoyl]thiazolidine-2-thione in dry dimethylformamide (10 ml) and the mixture was allowed to react at room temperature for 14 hours. The reaction mixture was concentrated by evaporation under reduced pressure and the residue was subjected to silica gel column chromatography, eluted with chloroform-methanol (50:1), to give 500 mg (0.741 mmol) of 1-2-[5-[3,4-bis(β-methoxyethoxymethoxy)phenyl]-2,4-pentadienoyl]amioethyl]-4-benzhydroxypiperidine.

To a solution of 500 mg (0.741 mmol) of the amide compound in methanol (10 ml) was added 144 mg (0.757 mmol) of p-toluenesulfonic acid monohydrate, and the mixture was refluxed for 35 minutes. Water was added to the reaction mixture, which was adjusted to a pH value of 11 by the addition of an aqueous solution of sodium carbonate, and then extracted with ethyl acetate. The organic layer was washed with water and concentrated by evaporation under reduced pressure. The residue was subjected to silica gel column chromatography, eluted with chloroform-methanol (10:1), to give 185 mg (0.353 mmol) of 1-[2-[5-(3,4-dihydroxyphenyl)-2,4-pentadienoyl]aminoethyl-4-benzhydroxypiperidine. Spectrophotometric data of the product support the structure shown below.

IR $\nu_{max}{}^{cm-1}$(KBr): 3300, 1650, 1590

¹H-NMR (deutero pyridine) δ: 1.67–2.93 (10H, m), 3.57 (3H, m), 5.60 (1H, s), 6.25 (1H, d, J=15 Hz), 6.73–7.67 (17H, m).

EXAMPLE 119

To a solution of 508 mg (1.15 mmol) of 1-(2-phthaloylaminoethyl)-4-benzhydroxypiperidine in ethanol (10 ml) was added, under argon atmosphere 89 mg (1.78 mmol) of hydrazine hydrate, and the mixture was refluxed for 1 hour. The reaction mixture was concentrated by evaporation under reduced pressure. To the residue was added 5 ml of dry dimethylformamide, followed by addition of a solution of 856 mg (2.11 mmol) of N-[5-[3-methoxy-4-(β-methoxyethoxymethoxy)phenyl]-2,4-pentadienoyl]thiazolidine-2-thione in dry dimethylformamide (5 ml) and the mixture was reacted at room temperature for 1.5 hours. The reaction mixture was concentrated by evaporation under reduced pressure and the residue was subjected to silica gel column chromatography, eluted with chloroform-methanol (50:1), to give 690 mg (1.15 mmol) of 1-[2-[5-[3-methoxy-4-(β-methoxyethoxymethoxy)phenyl]-2,4-pentadienoyl]aminoethyl]-4-benzhydroxypiperidine.

To a solution of 690 mg (1.15 mmol) of the amide compound in methanol (14 ml) was added 212 mg (1.12 mmol) of p-toluenesulfonic acid monohydrate, and the mixture was refluxed for 25 minutes. Water was added to the reaction mixture, which was adjusted to a pH value of 11 by the addition of an aqueous solution of sodium carbonate, and then extracted with ethyl acetate. The organic layer was washed with water and concentrated by evaporation under reduced pressure. The residue was subjected to silica gel column chromatography, eluted with chloroform-methanol (50:1), to give 393 mg (0.730 mmol) of 1-[2-[5-(3-methoxy-4-hydroxyphenyl)-2,4-pentadienoyl]aminoethyl]4-benzhydroxypiperidine.

Spectrophotometric data of the product support the structure shown below.

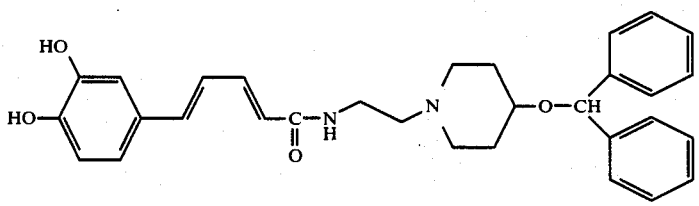

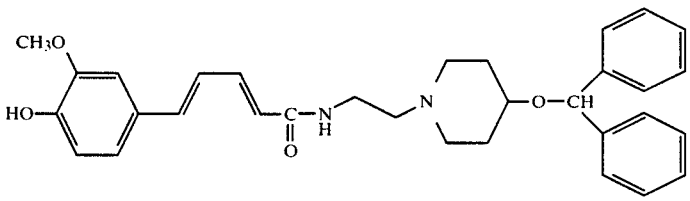

IR $\nu_{max}^{cm-1}$ (KBr): 3300, 1650, 1590
$^1$H-NMR (deutero pyridine) δ: 1.53–2.88 (10H, s), 3.58 (3H, m), 3.67 (3H, s), 5.63 (1H, s), 6.33 (1H, d, J=15 Hz), 6.75–7.63 (17H, m).

EXAMPLE 120

To a solution of 508 mg (1.15 mmol) of 1-(2-phthaloylaminoethyl)-4-benzhydroxypiperidine in ethanol (10 ml) was added, under argon atmosphere, 86 mg (1.72 mmol) of hydrazine hydrate, and the mixture was refluxed for 1 hour. The reaction mixture was concentrated by evaporation under reduced pressure. To the residue was added 4 ml of dry dimethylformamide, followed by addition of a solution of 895 mg (2.04 mmol) of N-[5-[3,5-dimethoxy-4-(β-methoxyethoxymethoxy)phenyl]-2,4-pentadienoyl]thiazolidine-2-thione in dry dimethylformamide (6 ml), and the mixture was reacted at room temperature for 2 hours. The reaction mixture was concentrated by evaporation under reduced pressure and the residue was subjected to silica gel column chromatography, eluted with chloroform-methanol (50:1), to give 374 mg (0.593 mmol) of 1-[2-[5-[3,5-dimethoxy-4-(β-methoxyethoxymethoxy)phenyl]-2,4-pentadienoyl]aminoethyl]-4-benzhydroxypiperidine.

To a solution of 374 mg (0.593 mmol) of the amide compound in methanol (9 ml) was added 120 mg (0.631 mmol) of p-toluenesulfonic acid monohydrate, and the mixture was refluxed for 30 minutes. Water was added to the reaction mixture, which was adjusted to a pH value of 11 by the addition of an aqueous solution of sodium carbonate, and then extracted with ethyl acetate. The organic layer was washed with water, concentrated by evaporation under reduced pressure, and the residue was subjected to silica gel column chromatography. There was obtained from fractions eluted with chloroform-methanol (50:1) 314 mg (0.552 mmol) of 1-[2-[5-(3,5-dimethoxy-4-hydroxyphenyl)-2,4-pentadienoyl]aminoethyl]-4-benzhydroxypiperidine.

Spectrophotometric data of the product support the structure shown below.

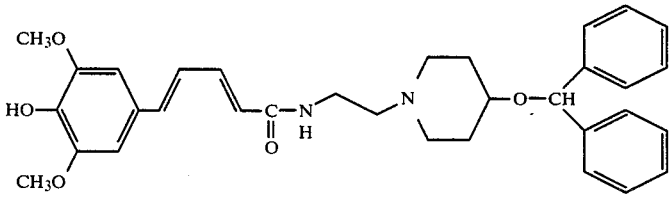

IR $\nu_{max}^{cm-1}$ (KBr): 3350, 1610, 1590
$^1$H-NMR (deutero chloroform) δ: 2.55–2.92 (10H, m), 3.42 (3H, m), 3.78 (6H, s), 5.42 (1H, s), 5.80 (1H, d, J=15 Hz), 6.38–7.40 (16H, m).

EXAMPLE 121

To 0.8 mg (20 mmol) of a 60% sodium hydride, after washed several times with n-hexane, was added 10 ml of dimethyl sulfoxide, and the mixture was reacted in an argon atmosphere at 75° C. for 45 minutes. The reaction mixture was added in small portions to 50 g (400 mmol) of 1,4-dichlorobutane in 20 ml of dimethyl sulfoxide, and the resulting mixture was reacted at room temperature overnight. To the reaction mixture was added water, and the mixture was extracted with chloroform. The organic layer was dried over sodium sulfate and then concentrated under reduced pressure, and the residue obtained was subjected to silica gel column chromatography. There was obtained from a fraction eluted with chloroform-methanol (100:1) 5.27 g (19.5 mmol) of 7-(4-chlorobutyl)-theophylline.

To a solution of 1.7 g (20 mmol) of piperazine in 20 ml of water was added 20 ml of tetrahydrofuran. To the resulting solution was added a solution of 914 mg (2 mmol) of N-[3-{3,4-di-(β-methoxyethoxymethoxy)phenyl}-2-propenoyl]thiazolidine-2-thione in tetrahydrofuran (20 ml), and the mixture was reacted at room temperature for 1 hour. To the reaction mixture was added 2N-aqueous sodium hydroxide solution, and the mixture was extracted with chloroform. The organic layer was concentrated under reduced pressure, and the residue obtained was subjected to silica gel column chromatography. There was obtained from a fractions eluted with chloroform-methanol (20:1) 650 mg (1.5 mmol) of 1-[3-{3,4-di-(β-methoxyethoxymethoxy)phenyl}-2-propenoyl]piperazine.

To the pieperazine compound obtained above was added 5 ml of toluene. To the resulting mixture were added 406 mg (1.5 mmol) of 7-(4-chlorobutyl)-theophylline and 5 ml of triethylamine, and the mixture was heated under reflux overnight. To the reaction mixture was added ethyl acetate, and the mixture was washed with water and then concentrated. The residue obtained was subjected to silica gel column chromatography. There was obtained from a fraction eluted with chloroform-methanol (96:4) 290 mg (0.44 mmol) of 7-[4-[4-[3-{3,4-di-(β-methoxyethoxymethoxy)phenyl}-2-propenoyl]piperazi-1-nyl]butyl]theophylline.

To a solution of 290 mg (0.44 mmol) of the amide compound obtained above in 10 ml of methanol was added 190 mg (1 mmol) of p-toluenesulfonic acid hydrate, and the mixture was heated under reflux for 1 hour. The reaction mixture was adjusted to pH 10 with saturated aqueous solution of carbonate solution and then extracted with chloroform. The organic layer was concentrated under reduced pressure, and the residue obtained from a fraction eluted with chloroform-methanol (20:1) 80 mg (0.16 mmol) of 7-[4-[4-{3-(3,4-dihydroxyphenyl)-2-propenoyl}piperazi-1-nyl]butyl]-theophylline. Spectrophotometric data of the product support the structure shown below.

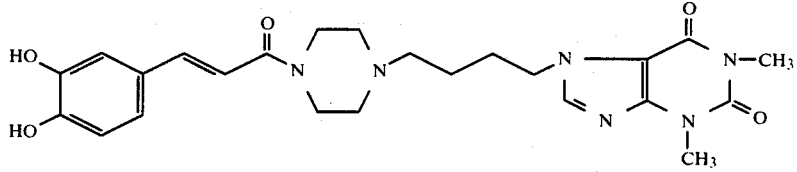

IR $\nu_{max}^{cm-1}$ (KBr): 3300, 1710, 1660, 1600
$^1$H-NMR (deutero pyridine) δ: 1.2–2.5 (10H), 3.40 (3H, s), 3.53 (3H, s), 3.67 (4H), 4.30 (2H, t, J=7 Hz), 6.8–8.0 (5H), 7.95 (1H, s).

EXAMPLE 122

In 10 ml of benzene were heated under reflux for 1 hour 5.36 g (20 mmol) cf N-(3-bromopropyl)-phthalimide and 4.04 g (40 mmol) of 4-hydroxypiperidine. To the reaction mixture was added water, and the mixture was extracted with n-butanol. The organic layer was concentrated under reduced pressure, and the residue obtained was subjected to silica gel column chromatography. There was obtained from a fractions eluted with chloroform-methanol (20:1) 3.18 g (11.7 mmol) of 1-(3-phthaloylaminopropyl)-4-hydroxypiperidine.

In 10 ml of toluene were heated overnight under reflux in the presence of 3.45 g (25 mmol) of potassium carbonate 3.18 g (11.7 mmol) of the piperidine compound obtained above and 5.06 g (25 mmol) of of benzhydryl chloride. To the reaction mixture was added water, and the mixture was extracted with chloroform. The chloroform layer was concentrated under reduced pressure, and the residue obtained was subjected to silica gel column chromatography. There was obtained from a fraction eluted with chloroform-methanol (50:1) 3.14 mg (6.92 mmol) of 1-(3-phthaloylaminopropyl)-4-benzhydroxypiperidine.

To a solution of 500 mg (1.10 mmol) of the piperidine compound obtained above in 10 ml of ethanol was added in an argon atmosphere 138 mg (2.20 mmol) of a 80% hydrazine hydrate. The mixture was heated under reflux for 2 hours and 30 minutes. To the residue obtained was added 10 ml of dimethylformamide. To the resulting solution was added a solution of 503 mg (1.10 mmol) of N-[3-[3,4 -di(β-methoxyethoxymethoxy)-phenyl]-2-propenoyl]thiazolidine-2-thione in N,N-dimethylformamide solution (10 ml), and the mixture was reacted at room temperature for 15 hours. The reaction mixture was concentrated under reduced pressure. and the residue obtained was subjected to silica gel column chromatography. There was obtained from a fraction eluted with chloroform-methanol (50:1) 559 mg (0.84 mmol) of 1-[3-[3-[3,4-di(β-methoxyethoxymethoxy)phenyl]-2-propenoyl]aminopropyl]-4-benzhydroxypiperidine.

To a solution of 559 mg (0.84 mmol) of the amide compound obtained above in 12 ml of methanol was added 191 mg (1.01 mmol) of p-tolenesulfonic acid monohydrate, and the mixture was heated under reflux for 20 minutes. To the reaction mixture was added saturated aqueous solution of bicarbonate solution to adjust the pH to 10, and the mixture was extracted with chloroform. The organic layer was dried over anhydrous sodium sulfate and then concentrated under reduced pressure, and the residue obtained was subjected to silica gel column chromatography. There was obtained from a fraction eluted with chloroform-methanol (100:9) 323 mg (0.66 mmol) of 1-[3-[3-(3,4-dihydroxyphenyl)-2-propenoyl]aminopropyl]-4-benzhydroxypiperidine. Spectrophotometric data of the product support the structure shown below.

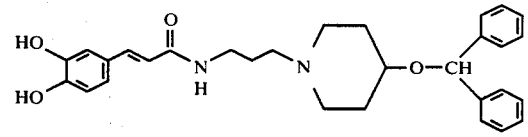

IR $\nu_{max}^{cm-1}$ (CHCl$_3$) 3630, 3300, 1660, 1600
$^1$H-NMR (CD$_3$OD) δ: 1.5–3.6 (15 H, m), 5.51 (1H, s), 6.32 (1H, d, J=15 Hz, 6.6–7.7 (14H, m).

EXAMPLE 123

In 14 ml of dimethyl sulfoxide was dissolved in an argon atmosphere 1.06 g (60% 26.4 mmol) of sodium hydride after having been washed with dry hexane. The solution was stirred at 75° C. for 40 minutes and then allowed to cool to room temperature. To this solution was added a suspension of 3.96 g (22 mmol) of theophylline in dimethyl sulfoxide (10 ml), and the mixture was stirred for 30 minutes. To the resulting mixture was added dropwise with a dropping funnel in 15 minutes a solution of 50 g (440 mmol) of 1,3-dichloropropane in dimethyl sulfoxide (20 ml). The mixture was stirred at room temperature for 15 hours and then extracted with chloroform. The organic layer was dried over anhydrous sodium sulfate and then concentrated under reduced pressure. The residue obtained was subjected to silica gel column chromatography. Recrystallization from methanol of 4.5 g of the residue obtained from a fraction eluted with chloroform yielded 2.89 g (11.24 mmol) of 7-[1-(3-chloro)propyl]theophylline.

To a solution of 2.15 g (25 mmol) of piperazine in water (50 ml) was added 25 ml of tetrahydrofuran. To the mixture was added with a dropping funnel a solution of 959 mg (2.5 mmol) of N-[3-[3-methoxy-4-(β-methoxyethoxymethoxy)phenyl]-2-propenoyl]thiazolidine-2-thione in tetrahydrofuran (25 ml). To the mixture, after stirred at room temperature for 30 minutes, was added 50 ml of 2N-aqueous sodium hydroxide solution, and the mixture was extracted with chloroform. The organic layer was dried over anhydrous sodium sulfate and then concentrated under reduced pressure. The residue obtained was subjected to silica gel column chromatography. There was obtained from a fractions eluted with chloroform-methanol (100:9) 777 mg (2.22 mmol) of 1-[3-[3-methoxy-4 -2-propenoyl]piperazine.

In N,N-dimethylformamide (8 ml) and diisopropylethylamine (4 ml) was dissolved in an argon atmosphere 777 mg (2.22 mmol) of the piperazine derivative obtained above. To the resulting solution was added 570 mg (2.22 mmol) of 7-[1-[3-chloro)propyl]theophylline, and the mixture was stirred at 100° C. for 26 hours and 30 minutes. To the mixture, after having been allowed to cool to room temperature, was added water, and the resulting mixture was extracted with ethyl acetate. After having been dried over anhydrous sodium sulfate, the organic layer was concentrated under reduced pressure. The residue (1.2 g) obtained was subjected to silica gel column chromatography. There was obtained from a fractions eluted with chloroform-methanol (50:1) 457 (0.80 mmol) of 7-[3-[4-[3-[-2-propenoyl]piperazi-1-nyl]-1-propyl]ethophylline.

To a solution of 475 mg (0.80 mmol) of the theophylline derivative obtained above in methanol (5 ml) was added 380 mg (2.00 mmol) of para-toluenesulfonic acid hydrate, and the resulting mixture was heat under reflux for 3 hours. To the mixture, after having been allowed to cool to room temperature, was added saturated aqueous solution of bicarbonate solution, and the mixture was extracted with chloroform. The organic layer was dried over anhydrous sodium sulfate and then concentrated under reduced pressure. The residue obtained was subjected to silica gel column chromatography. There was obtained from a fractions eluted with chloroform-methanol (20:1) 333 mg (0.69 mmol) of 7-[3-[4-[3-(2-propenoyl]piperazi-1-nyl]-1-propyl]theophylline.
Spectrophotometric data of the product support the structure shown below.

raphy. There was obtained from a fraction eluted with chloroform-methanol (20:1) 7.91 g (26.2 mmol) of 1-(4-phthaloylaminobutyl)-4-hydroxypiperidine.

To 7.91 g (26.2 xmol) of the alcohol compounds obtained above were added 10.0 ml (56.3 mmol) of benzhydryl chloride and 4.36 g (31.6 mmol) of potassium carbonate, and the resulting mixture was reacted at 135° C. for 4 hours. To the reaction mixture, after cooled, was added 30 ml of a chloroform-methanol (2:1) solution, and the resulting mixture was subjected to silica gel column chromatography. There was obtained from a fractions eluted with chloroform 8.56 g (18.3 mmol) of 1-(4-phthaloylaminobutyl)-4-benzhydroxypiperidine.

To a solution of 356 mg (0.760 mmol) of the piperidine compound obtained above in ethanol (7 ml) was added 72 mg (1.15 mmol) of hydrazine hydrate, and the mixture was refluxed fcr 1 hour in an argon atmosphere. To the residue obtained by concentration under reduced pressure was added dry dimethylformamide (3 ml). To the resulting mixture was further added a solution of 507 mg (1.32 mmol) of N-[3-[3-methoxy-4-(β-methoxyethoxymethoxy)phenyl]-2-propenoyl]thiazolidine-2-thione in dimethylformamide (5 ml), and the resulting mixture was reacted at room temperature for 4 hours. The residue obtained by concentration under reduced pressure was subjected to silica gel column chromatography. There was obtained from a fractions eluted with chloroform-methanol (50:1) 382 mg (0.634 mmol) of 1-[4-[3-[3-methoxy-4-(β-methoxyethoxymethoxy)phenyl]-2-propenoyl]aminobutyl]-4-benzhydroxypiperidine.

To a solution of 382 mg (0.634 mmol) of the amide compound obtained above in methanol (8 ml) was added 125 mg (0.657 mmol) of p-toluenesulfonic acid

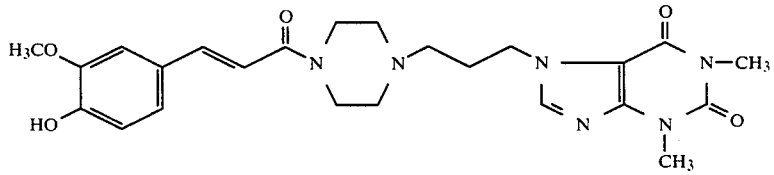

IR $\nu_{max}^{cm-1}$ (chloroform): 3550, 1710, 1660, 1600
$^1$H-NMR (deutero chloroform) δ: 1.8-2.8 (8H), 3.2-4.0 (4H), 3.42 (3H, s), 3.61 (3H, s), 3.92 (3H, s), 4.40 (2H, t, J=6), 6.67 (1H, d, J=16), 6.7-7.3 (3H), 7.58 (1H, s), 7.60 (1H, d, J=16).

EXAMPLE 124

A solution of 7.34 g (72.6 mmol) of 4-hydroxypiperidine and 10.3 g (36.5 mmol) of N-(4-bromobutyl)phthalimide in 150 ml of benzene was refluxed in an argon atmosphere for 8 hours. To the reaction mixture, after cooled, was added water, and the resulting mixture was extracted with ethyl acetate. The organic layer was concentrated under reduced pressure, and the residue obtained was subjected to silica gel column chromatogmonohydrate, and the mixture was refluxed for 30 minutes. To the reaction mixture was added water, and the mixture was adjusted to pH 11 with an aqueous sodium carbonate solution and then extracted with ethyl acetate. The organic layer was washed with water and then concentrated under reduced pressure. The residue obtained was subjected to silica gel column chromatography. There was obtained from a fraction eluted with chloroform-methanol (20:1) 206 mg (0.400 mmol) of 1-[4-[3-(3-methoxy-4-hydroxyphenyl)-2-propenoyl-]aminobutyl]-4-benzhydroxypiperidine. Spectrophotometric data of the product support the structure shown below.

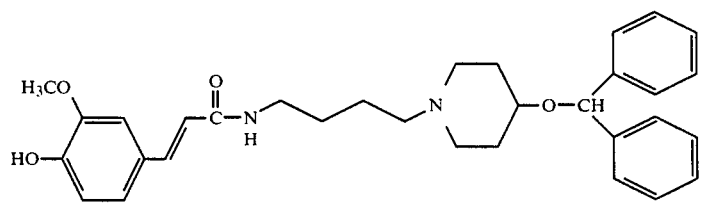

IR $\nu_{max}{}^{cm-1}$ (KBr): 3350, 1660, 1600

$^1$H-NMR (deutero chloroform) δ: 1.37–3.55 (17H, m), 3.72 (3H, s), 5.43 (1H, s), 6.17 (1H, d, J=16 Hz), 6.62–7.57 (14H, m).

EXAMPLE 125

To a solution of 1.12 g (13 mmol) of piperazine in water (25 ml) was added 12 ml of tetrahydrofuran. To the resulting solution was added a solution of 538 mg (1.3 mmol) of N-[3-{3,5-dimethoxy-4-(β-methoxyethoxymethoxy)phenyl}-2-propenoyl]thiazolidine-2-thione in tetrahydrofuran (20 ml), and the mixture was reacted at room temperature for 1 hour. To the reaction mixture was added 2N-aqueous sodium hydroxide solution, and the mixture was extracted with chloroform. The organic layer was concentrated under reduced pressure, and the residue obtained was subjected to silica gel column chromatography. There was obtained from a fraction eluted with chloroform-methanol (20:1) 421 mg (1.1 mmol) of 1-[3-{3,5-dimethoxy-4-(β-methoxyethoxymethoxy)phenyl}-2-propenoyl]piperazine.

To the piperazine compound obtained above in 2 ml of toluene were added 300 mg (1.1 mmol) of 7-(4-chlorobutyl)-theophylline and 1 ml of triethylamine, and the resulting mixture was heated under reflux overnight. To the reaction mixture was added ethyl acetate, and the mixture was washed with water and then concentrated. The residue obtained was subjected to silica gel column chromatography. There was obtained from a fraction eluted with chloroform-methanol (96:4) 324 mg (0.53 mmol) of 7-[4-[4-[3-{3,5-dimethoxy-4-(β-methoxyethoxymethoxy)phenyl}-2-propenoyl]-piperazi-1-nyl]butyl]theophylline.

To a solution of 324 mg (0.53 mmol) of the amide compound obtained above in 10 ml of methanol was added 380 mg (2 mmol) of p-tolenesulfonic acid hydrate, and the mixture was heated under reflux for 1 hour. The reaction mixture was adjusted to pH 10 with saturated aqueous sodium carbonate solution and then extracted with chloroform. The organic layer was concentrated under reduced pressure, and the residue obtained was subjected to silica gel column chromatography. There was obtained from a fraction eluted with chloroform-methanol (20:1) 245 mg (0.46 mmol) of 7-[4-[4-{3-(3,5-dimethoxy-4-hydroxyphenyl)-2-propenoyl}piperazi-1-nyl]butyl]theophylline. Spectrophotometric data of the product support the structure shown below.

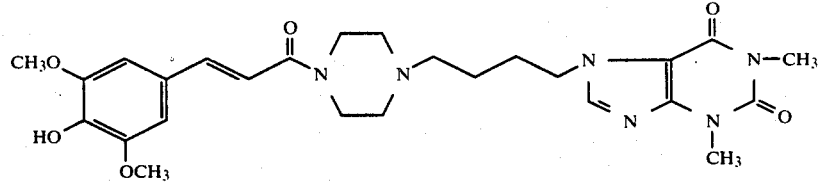

IR $\nu_{max}{}^{cm-1}$ (KBr): 3400, 1710, 1660, 1605

$^1$H-NMR (deutero methanol) δ: 1.3–2.6 (10H), 3.30 (3H, s), 3.46 (3H, s), 3.68 (4H), 3.85 (6H, s), 4.27 (2H, t, J=6 Hz), 6.82 (2H, s), 6.85 (1H, d, J=15 Hz), 7.42 (1H, d, J=15 Hz), 7.82 (1H, s).

EXAMPLE 126

To a solution of 454 mg (1 mmol) of 1-(3-phthaloylaminopropyl)-4-benzhydroxypiperidine in 10 ml of ethanol was added in an argon atmosphere 125 mg (2 mmol) of a 80% hydrazine hydrate, and the mixture was heated under reflux for 1 hour. The reaction mixture was concentrated under reduced pressure. To the residue obtained was added 10 ml of tetrahydrofuran. To the resulting solution was added a solution of 413 mg (1 mmol) of N-[3-{3,4-dimethoxy-4-(β-methoxyethoxymethoxy)phenyl}-2-propenoyl]thiazolidine-2-thione in tetrahydrofuran (10 ml), and the mixture was reacted at room temperature for 2 hours. The reaction mixture was concentrated under reduced pressure, and the residue obtained was subjected to silica gel column chromatography. There was obtained from a fraction eluted with chloroform - methanol (50:1) 400 mg (0.65 mmol) of 1-[3-[3-{3,5-dimethoxy-4-(β-methoxyethoxymethoxy)phenyl}-2-propenoyl]aminopropyl]-4-benzhydroxypiperidine.

To a solution of 400 mg (0.65 mmol) of the amide compound obtained above in 10 ml of methanol was added 133 mg (0.7 mmol) of p-toluenesulfonic acid monohydrate, and the resulting mixture was heated under reflux for 20 minutes. The reaction mixture was adjusted to pH 10 with saturated aqueous sodium bicarbonate solution and then extracted with chloroform. The chloroform layer was concentrated under reduced pressure, and the residue obtained was subjected to silica gel column chromatography. There was obtained from a fraction eluted with chloroform - methanol (20:1) 320 mg (0.60 mmol) of 1-[3-{3-(3,5-dimethoxy-4-hydroxyphenyl)-2-propenoyl}aminopropyl]-4-benzhydroxypiperidine. Spectrophotometric data of the product support the structure shown below.

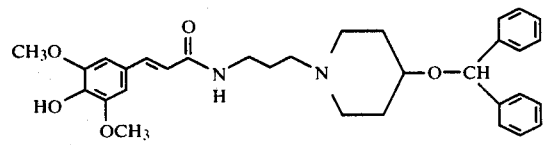

IR $\nu_{max}{}^{cm-1}$ (KBr): 3300, 1660, 1620

$^1$H-NMR (CDCl$_3$) δ (ppm): 1.5–3.7 (15H, m), 3.73(6H, s), 5.47 (1H, s), 6.22 (1H, d, J-16 Hz), 6.67 (2H, s), 7.25 (10H), 7.43 (1H, d, J-16 Hz).

EXAMPLE 127

To a solution of 2.46 g (28.6 mmol) of piperazine in 50 ml of water was added 25 ml of tetrahydrofuran. To the resulting solution was added with a dropping funnel a solution of 970 mg (2.86 mmol) of N-[3-(3,4,5-trimethoxyphenyl)-2-propenoyl]thiazolidine-2-thione in 25 ml of tetrahydrofuran. The mixture was stirred at room temperature for 30 minutes followed by addition of 50 ml of 2N-aqueous sodium hydroxide solutiqn thereto, and the resulting mixture was extracted with chloroform. The organic layer was dried over anhydrous sodium sulfate and then concentrated under reduced pressure. The residue obtained was subject to silica gel column chromatography. There was obtained from a fraction eluted with chloroform - methanol (100:9) 727 mg (2.37 mmol) of 1-[3-(3,4,5-trimethoxyphenyl)-2-propenoyl]piperazine.

In an argon atmosphere, 727 mg (2.37 mmol) of the piperazine derivative obtained above was dissolved in 5 ml of toluene and 3.3 ml (23.7 mmol) of triethylamine. To the resulting solution was added 608 mg (23.7 mmol) of 7-[1-(3-chloro)propyl]theophylline, and the mixture was stirred at 100° C. for 13 hours. The mixture was allowed to cool to room temperature followed by addition of water thereto, and the mixture was extracted with chloroform. The organic layer was dried over anhydrous sodium sulfate and then concentrated under reduced pressure. The residue (1.2 g) obtained was subjected to silica gel column chromatography. There was obtained from a fractions eluted with chloroform - methanol (100:3) 560 mg (1.06 mmol) of 7-[3-[4-[3-(3,4,5-trimethoxyphenyl)-2-propenoyl]piperazi-1-nyl]-1-propyl]theopylline. Spectrophotometric data of the product support the structure shown below.

with ethyl acetate. The organic layer was dried over anhydrous sodium sulfate and the concentrated under reduced pressure. The residue obtained was subjected to silica gel column chromatography. There was obtained from a fraction eluted with chloroform - methanol (50:1) 220 mg (0.33 mmol) of 7-[3-[4-[5-[3,4-di($\beta$-methoxyethoxymethoxy)phenyl]-2,4-pentadienoyl]-piperazi-1-nyl]-1-propyl]theophylline.

To a solution of 220 mg (0.33 mmol) of the theophylline derivative obtained above in 6 ml of methanol was added 156 mg (0.82 mmol) of p-toluenesulfonic acid hydrate, and the mixture was heated under reflux for 3 hours. The mixture was allowed to cool to room temperature followed by addition of saturated aqueous sodium bicarbonate solution, and extracted with chloroform. The organic layer was dried over anhydrous sodium sulfate and then concentrated under reduced pressure. The residue (250 mg) obtained was subjected to silica gel column chromatography. There was ob-

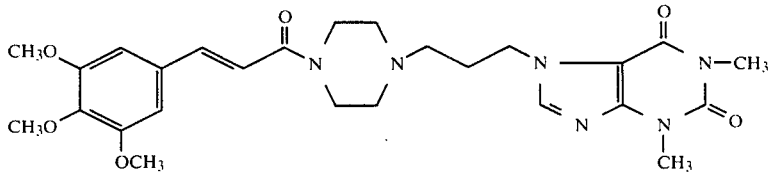

IR $\nu_{max}^{cm-1}$ (CHCl$_3$): 1710, 1660, 1590

$^1$H-NMR (deutero chloroform) $\delta$: 1.8 O 2.7 (8H), 3.3–4.0 (4H), 3.46 (3H, s), 3.64 (3H, s), 3.92 (3H, s), 3.95 (6H, s), 4.44 (2H, t, J=6), 6.78 (H, s), 6.80 (1H, d, J=16), 7.62 (1H, d, =16), 7.64 (1H, s).

tained from a fraction eluted with chloroform - methanol (20:1) 49 mg (0.10 mmol) of 7-[3-[4-[5-(3,4-dihydroxyphenyl)-2,4-pentadienoyl]piperazi-1-propyl]-theophylline. Spectrophotometric data of the product support the structure shown below.

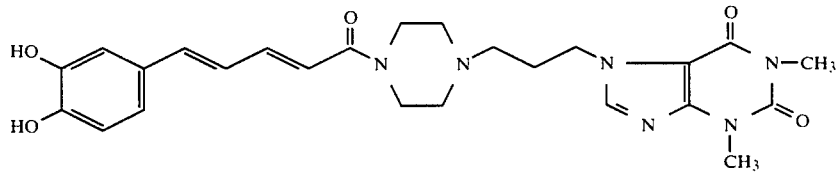

EXAMPLE 128

To a solution of 1.72 g (20 mmol) of piperazine in 50 ml of water was added 25 ml of tetrahydrofuran. To the solution was added with a dropping funnel a solution of 967 mg (2.00 mmol) of N-[5-[3,4-di($\beta$-methoxyethoxymethoxy)phenyl]-2,4-pentadienoyl]thiazolidine-2-thione in 25 ml of tetrahydrofuran. The resulting mixture was stirred at room temperature, followed by addition of 50 ml of 2N-aqueous sodiuxm hydroxide solution, was extracted with chloroform. The organic layer was dried over anhydrous sodium sulfate and then concentrated under reduced pressure. The residue obtained was subjected to silica gel column chromatography. There was obtained from a fractions eluted with chloroform - methanol (100:9) 599 mg (1.33 mmol) of 1-[5-[3,4-di($\beta$-methoxyethoxymethoxy)phenyl]-2,4-pentadienoyl]piperazine.

In an argon atmosphere, 599 mg (1.22 mmol) of the piperazine derivative obtained above was dissolved in 6 ml of N,N-dimethylformamide and 2.3 ml of diisopropylethylamine. To the resulting solution was added 342 mg (1.33 mmol) of 7-[1-(3-chloro)propyl]theopylline, and the mixture was stirred at 100° C. for 22 hours. The mixture was allowed to cool to room temperature followed by addition of water thereto, and extracted IR $\nu_{max}^{cm-1}$ (KBr): 3350, 1710, 1660, 1600

$^1$H-NMR (deutero methyl sulfoxide) $\delta$: 1.6–2.6 (8H), 3.0–3.8 (4H), 3.23 (3H, s), 3.47 (3H, s), 4.28 (2H, t, J=6), 6.3–7.3 (7H), 8.00 (1H, s).

EXAMPLE 129

To a solution of 367 mg (0.783 mmol) of 1-(4-phthaloylaminobutyl)-4-benzhydroxypiperidine in ethanol (10 ml) was added 75 mg (1.20 mmol) of hydrazine hydrate, and the mixture was refluxed for 2 hours. To the residue obtained by concentration of the reaction mixture under reduced pressure was added 3 ml of dry dimethylformamide. To the residue was further added a solution of 751 mg (1.55 mmol) of N-[5-[3,4-bis($\beta$-methoxyethoxymethoxy)phenyl]-2,4-pentadienoyl]-thiazolidine-2-thione in dry dimethylformamide (6 ml), and the mixture was reacted at room temperature for 2 hours. The reaction mixture was concentrated under reduced pressure, and the residue obtained was subjected to silica gel column chromatography. There was obtained from a fraction eluted with chloroform - methanol (50:1) 391 mg (0.556 mmol) of 1-[4-[5-3,4-bis($\beta$-methoxyethoxymethoxy)phenyl]-2,4-pentadienoyl-]aminobutyl]-4-benzhydroxypiperidine.

To a solution of 391 mg (0.556 mmol) of the amide compound obtained above in methanol (10 ml) was added 107 mg (0.563 mmol) of p-toluenesulfonic acid monohydrate, and the mixture was refluxed for 1 hour. To the reaction mixture was added water, and the mixture was adjusted to pH 11 with an aqueous sodium carbonate solution and then extracted with ethyl acetate. The organic layer was washed with water and then concentrated under reduced pressure, and the residue obtained was subjected to silica gel column chromatography. There was obtained from a fraction eluted with chloroform - methanol (10:1) 149 mg (0.270 mmol) of added 380 mg (2 mmol) of p-toluenesulfonic acid hydrate, and the mixture was heated under reflux for 1 hour. The reaction mixture was adjusted to pH 10 with saturated aqueous sodium carbonate solution and then extracted with chloroform. The organic layer was concentrated under reduced pressure, and the residue obtained was subjected to silica gel column chromatography. There was obtained from a fractions eluted with chloroform - methanol (20:1) 245 mg (0.47 mmol) of 7-[4-[4-{5-4-hydroxyphenyl)-2,4-pentadienoyl}piperazil-nyl]butyl]theophylline. Spectrophotometric data of the product support the structure shown below.

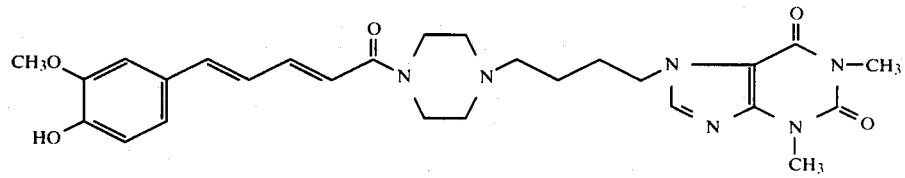

1-[4-[5-(3,4-dihydroxyphenyl)-2,4-pentadienoyl-]aminobutyl]-4-benzhydroxypiperidine. Spectrophotometric data of the product support the structure shown below.

IR $\nu_{max}^{cm-1}$ (KBr): 3400, 1705, 1660, 1580
1H-NMR (deutero methanol) δ: 1.3-2.7 (10H), 3.32 (3H, s), 3.48 (3H, s), 3.63 (4H), 3.83 (3H, s), 4.28 (2H, t, J=7Hz), 6.46 (1H, d, J=16 Hz), 6.6-7.5 (6H), 7.82 (1H,

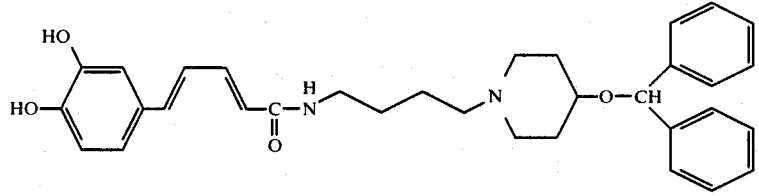

IR $\nu_{max}^{cm-1}$ (KBr): 3300, 1650, 1590
1H-NMR (deutero chloroform) δ: 1.30-3.53 (17H, m), 5.47 (1H, s), 5.97(1H, d, J=14 Hz), 6.53-7.40 (16H, m).

s).

EXAMPLE 130

To a solution of 1.7 g (20 mmol) of piperazine in 20 ml of water was added 20 ml of tetrahydrofuran. To the solution was added a solution of 820 mg (2 mmol) of N-[5-{3-methoxy-4-(β-methoxyethoxymethoxy)-phenyl}-2,4-pentadienoyl]thiazolidine-2-thione in tetrahydrofuran (10 ml), and the mixture was reacted at room temperature for 1 hour. To the reaction mixture was added 2N-aqueous sodium hydroxide solution, and the mixture was extracted with chloroform. The residue obtained was subjected to silica gel column chromatography. There was obtained from a fractions eluted with chloroform - methanol (20:1) 576 mg (1.5 mmol) of 1-[5-{3-methoxy-4β-methoxyethoxymethoxy)phenyl}-2,4-pentadienoyl]piperazine.

To the piperazine compound obtained above in 5 ml of toluene were added 405 mg (1.5 mmol) of 7-(4-chlorobutyl)-theophylline and 5 ml of triehtylamine, and the mixture was heated under reflux overnight. To the reaction mixture was added ethyl acetate, and the mixture was washed with water and then concentrated. The residue obtained was subjected to silica gel column chromatography. There was obtained from a fractions eluted with chloroform - methanol (96:4) 490 mg (0.8 mmol) of 7-[4-[4-[5-{3-methoxy-4-(β-methoxyethoxymethoxy)phenyl}-2,4-pentadienoyl]piperazi-1-nyl]butyl]theophylline.

To a solution of 490 mg (0.8 mmol) of the amide compound obtained above in 10 ml of methanol was

EXAMPLE 131

To a solution of 500 mg (1.10 mmol) of 1-(3-phthaloylaminopropyl)-4-benzhydroxypiperidine in 10 ml of ethanol was added 138 mg (2.20 mmol) of a 80% hydrazine hydrate in an argon atmosphere, and the solution was heated under reflux for 2 hours and 30 minutes. The reaction mixture was concentrated under reduced pressure. To the residue obtained was added 10 ml of N,N-dimethylformamide. To the resulting solution was added a solution of 450 mg (1.10 mmol) of N-[5-[3-methoxy-4-(β-methoxyethoxymethoxy)-phenyl]-2,4-pentadienoyl]thiazolidine-2-thione in N,N-dimethylformamide (10 ml), and the mixture was reacted at room temperature for 15 hours. The reaction mixture was concentrated under reduced pressure, and the residue obtained was subjected to silica gel column chromatography. There was obtained from a fractions eluted with chloroform - methanol (50:1) 484 mg (0.79 mmol) of 1-[3-[5-[3-m -(β-methoxyethoxymethoxy)-phenyl]-2,4-pentadienoyl]aminopropyl]-4-benzhydroxypiperidine.

To a solution of 484 mg (0.79 mmol) of the amide compound obtained above in 12 ml of methanol was added 180 mg (0.95 mmol) of p-toluenesulfonic acid mono hydrate, and the mixture was heated under reflux for 30 minutes. The reaction mixture was adjusted to pH 10 with saturated aqueous sodium bicarbonate solution and then extracted with ethyl acetate. The organic layer was dried over anhydrous sodium sulfate and then concentrated under reduced pressure. The residue obtained was subjected to silica gel column chromatography. There was obtained from a fraction eluted with tadienoyl]piperazi-1-nyl]butyl]theophylline. Spectrophotometric data of the product support the structure shown below.

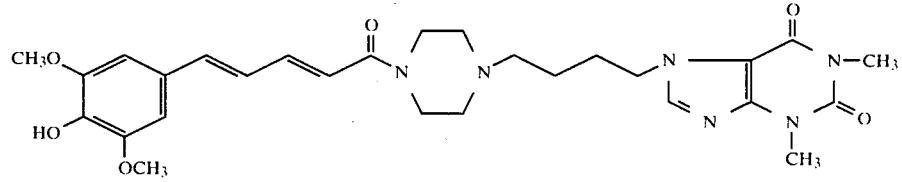

chloroform - methanol (20:1) 408 mg (0.77 mmol) of 1-[3-[5-[3-me 2,4-pentadienoyl]aminopropyl]-4-benzhydroxypiperidine. Spectrophotometric data of the product support the structure shown below.

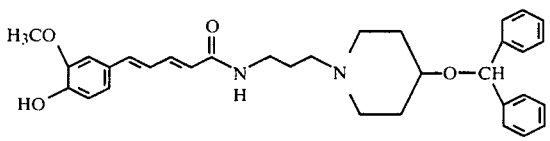

IR $\nu_{max}^{cm-1}$ (KBr): 3300, 1650, 1590

1H-NMR (CDCl$_3$) δ (ppm): 1.5–3.7 (15H, m), 3.86 (3H, s), 5.51 (1H, s), 5.82 (1H, d,J=15Hz), 6.5–7.6 (17H, m),

EXAMPLE 132

To a solution of 0.86 g (10 mmol) of piperazine in 10 ml of water was added 10 mlg of tetrahydrofuran. To the solution was added a solution of 440 mg (1 mmol) of N-[5-{3,5-dimethoxy-4-(β-methoxyethoxymethoxy)-phenyl}-2,4-pentadienoyl]thiazolidine-2-thione in tetrahydrofuran (5 ml), and the mixture was reacted at room temperature for 1 hour. To the reaction mixture was added 2N-aqueous sodium hydroxide solution, and the mixture was extracted with chloroform. The organic layer was concentrated under reduced pressure, and the residue obtained was subjected to silica gel column chromatography. There was obtained from a fraction eluted with chloroform-methanol (20:1) 190 mg (0.46mmol) of 1-[5-{3,5-dimethoxy-4-(β-methoxyethoxymethoxy)phenyl}-2,4-pentadienoyl]piperazine.

To the piperazine compound obtained above in 2 ml of toluene were added 130 mg (0.48 mmol) of 7-(4-chlorobutyl)-theophylline and 1 ml of triethylamine, and the mixture was heated under reflux overnight. To the reaction mixture was added ethyl acetate, and the mixture was washed with water and then concentrated. The residue obtained was subjected to silica gel column chromatography. There was obtained from a fraction eluted with chloroform - methanol (96 : 4) 136 mg (0.21 mmol) of 7-[4-[4-[5-{3,5-dimethoxy-4-(β-methoxyethoxymethoxy)phenyl}-2,4-pentadienoyl]piperazi-1-nyl]butyl]theophylline.

To 136 mg (0.21 mmol) of the amide compound obtained above in 10 ml of methanol was added 190 mg (1 mmol) of p-toluenesulfonic acid hydrate, and the mixture was heated under reflux for 1 hour. The reaction mixture was adjusted to pH 10 with saturated aqueous sodium carbonate solution and then extracted with chloroform. The organic layer was concentrated under reduced pressure, and the residue obtained was subjected to silica gel column chromatography. There was obtained from a fraction eluted with chloroform - methanol (20:1) 70 mg (0.12 mmol) of 7-[4-[4-[5-(2,4-pentadienoyl]piperazi-1-nyl]butyl]theophylline. Spectrophotometric data of the product support the structure shown below.

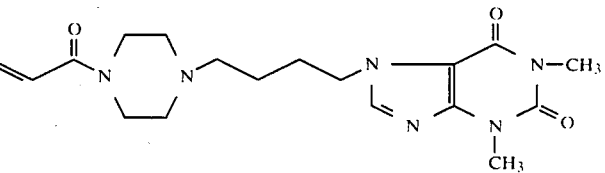

IR $\nu_{max}^{cm-1}$ (KBr): 3400, 2710, 2660, 1580

1H-NMR (deutero methanol) δ: 1.2–2.6 (10H), 3.33 (3H, s), 3.45 (3H, s), 3.62 (4H), 3.83 (6H, s), 4.25 (2H, t, J=6Hz), 6.3–7.5 (3H), 6.70 (2H, s), 7.73 (1H, s).

EXAMPLE 133

To a solution of 500 mg (1.07 mmol) of 1-(4-phthaloylaminobutyl)-4-benzhydroxypiperidine in 10 ml of ethanol was added 134 mg (2.14 mmol) of a 80% hydrazine hydrate, and the mixture was heated under reflux for 3 hours. The reaction mixture was concentrated under reduced pressure. To the residue obtained was added 10 ml of dimethylformamide. To the resulting solution was added a solution of 470 mg (1.07 mmol) of N-[5-[3,5-dimethoxy-4-(β-methoxyethoxymethoxy)-phenyl]-2,4-pentadienoyl]thiazolidine-2-thione in N,N-dimethylformamide (10 ml), and the mixture was reacted at room temperature for 15 hours. The reaction mixture was concentrated under reduced pressure, and the residue obtained was subjected to silica gel column chromatography. There was obtained from a fraction eluted with chloroform - methanol (50:1) 464 mg (0.70 mmol) of 1-[4-[5-[3,5-dimethoxy-4-(β-methoxyethoxymethoxy)phenyl]aminobutyl]-4-benzhydroxypiperidine.

To a solution of 464 mg (0.70 mmol) of the amide compound obtained above in 12 ml of methanol was added 160 mg (0.84 mmol) of p-toluenesulfonic acid mono hydrate, and the mixture was heated under reflux for 20 minutes. The reaction mixture was adjusted to pH 10 with saturated aqueous sodium bicarbonate solution and then extracted with ethyl acetate. The organic layer was dried over anhydrous sodium sulfate and then concentrated under reduced pressure. The residue obtained was subjected to silica gel column chromatography. There was obtained from a fraction eluted with chloroform - methanol (20:1) 298 mg (0.52 mmol) of 1-[4-[5-(3,5-dimethoxy-4-hydroxyphenol)-2,4-pentadienoylo]aminobutyl]-4-benzydroxypiperidine. Spectrophotometric data of the product support the structure shown below.

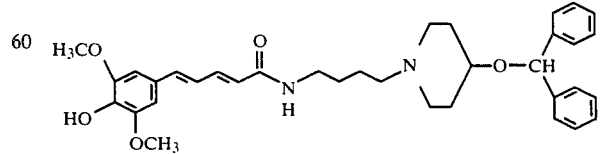

IR $\nu_{max}^{cm-1}$ (CHCl$_3$): 3630, 3540, 3450, 1660, 1620.

1H-NMR (CD$_3$OD$_3$) δ: 1.3–3.5 (17H,m), 3.80 (6H, s), 4.30 (1H, s), 5.95 (1H, d, J=15Hz), 6.5–7.6 (16H, m).

EXAMPLE 134

To a solution of 4.31 g (50 mmol) of piperazine in 50 ml of tetrahydrofuran. To the resulting solution was added with a dropping funnel a solution of 1.83 mg (5 mmol) of N-[5-(3,4,5-trimethoxyphenyl)-2,4-pentadienoyl]thiazolidine-2-thione in 25 ml of tetrahydrofuran, followed by stirring at room temperature for 30 minutes. To the mixture was added 60 ml of 2N-aqueous sodium hydroxide solution, and the mixture was extracted with chloroform. The organic layer was dried over anhydrous sodium sulfate and then concentrated under reduced pressure. The residue obtained was subjected to silica gel column chromatography. There was obtained from a fraction eluted with chloroform - methanol (100:9) 900 mg (2.71 mmol) of 1-[5-(3,4,5-trimethoxyphenyl)-2,4-pentadienoyl]piperazine.

In an argon atmosphere, 900 mg (2.71 mmol) of the piperazine derivative obtained above was dissolved in a mixture comprising 5 ml of toluene and 3.8 ml (27.1 mmol) of triethylamine. To the resulting mixture was added 695 mg (2.71 mmol) of 7-1-(3-chloro)propyl theophylline, and the mixture was stirred at 100° C. for 19 hours and 30 minutes. To the mixture, after allowed to cool to room temperature, was added water, and the mixture was extracted with chloroform. The organic layer was dried over anhydrous sodium sulfate and then concentrated under reduced pressure. The residue (1.7 g) obtained was subjected to silica gel column chromatography. There was obtained from a fraction eluted with chloroform - methanol (50:1) 309 mg (0.56 mmol) of 7-[3-[4-[5-(3,4,5-trimethoxyphenyl)-2,4-pentadienoyl]piperazi-1-nyl]-1-propyl]theophylline. Spectrophotometric data of the product support the structure shown below.

above-prepared enzyme solution and 0.1 ml of 8 mM CaCl$_2$ (calcium chloride). The mixture is reacted at 37° C. for 5 min. After cooled with ice, 60 μl of 1N-HCl (hydrochloric acid is added to the reaction mixture, which is then extracted with 8 ml of ethyl acetate. The extract is concentrated, and the concentrate is developed by spotting on a silica gel thin layer plate (Merck 60F $_{254}$). Measurement of the inhibitory activity is made by collecting fractions corresponding to lipoxygenase products 5-HETE (5(s)-hydroxy-6,8,11,14-eicosatetraenic acid) and LTB$_4$ (leucotriene B$_4$) and determining the radioactivity by a liquid scintillation counter. The lipoxygenase inhibiting activity is determined by decrease in the amount of the above-mentioned 5-lipoxygenase products. There have been found remarkeable 5-lipoxygenase-inhibiting activities as shown in Table I below. It has also been found that the amide derivatives of the invention other than those shown in Table I possess 5-lipoxygenase-inhibiting activities. 50% inhibitory concentration or 30% inhibitory concentration as indicated in the table means the concentration of an amide derivative required for reducing the amount of the above-mentioned 5-lipoxygenase products (5-HETE and LTB$_4$) to 50% or 30% of the amount when the amount of 5-HETE and LTB$_4$ produced in the absenced of the amide derivative is 100%.

Acute Toxicity

An acute toxicity test was run in ICR male mice (5-week old) by oral administration. LD$_{50}$'s with all of the compounds of the invention were 100 mg/kg body weight or higher, by which the high safety as compared with the efficacy was demonstrated.

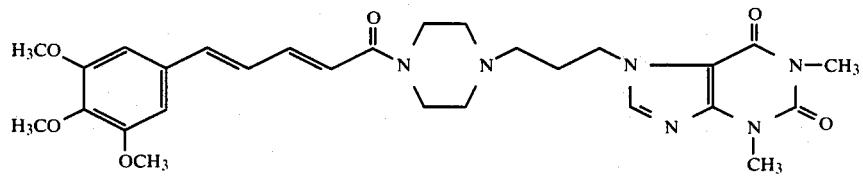

IR $\nu_{max}^{cm-1}$ (CHCl$_3$): 1710, 1660, 1585
1H-NMR (deutero chloroform) δ: 1.8–2.7 (8H), 3.2–4.1 (4H), 3.38 (3H, s), 3.56 (3H, s), 3.83 (3H, s), 3.86 (6H, s), 4.34 (2H, t, J=6 Hz), 6.3–7.5 (5H), 6.40 (1H, d, J=16 Hz), 7.42 (1H, s).

TEST EXAMPLE

5-Lipoxygenase-inhibiting Activity

Mouse mastcytoma cells P-815 are diluted in a culture solution, containing 90% Eagle Basic Medium (manufactured by Gibco Laboratories) to 5×10$^4$ cells/ml. The diluted solution is cultivated with shaking in air at 37° C. for 48 hours. Then, the culture solution is cooled with ice and centrifuged to collect the cells. The cells are suspended in a phosphate buffer solution at pH 7.4 at a concentration of 2×10$^7$ cells/ml. The suspension is treated in a ultrasonic cell disintegrater and then centrifuged at 10,000 r.p.m. for 10 min. The supernatant is used as a 5-lipogenase enzyme solution. In test tubes are placed 20 μl of radiolabelled arachidonic acid (10 Ci/ml), indomethacin (2×10$^{-8}$ mol) and an amide derivative to be tested, respectively. To each of the test tubes are added 0.45 ml of a phosphate buffer solution, 0.45 ml of the above-prepared suspension, 0.45 ml of the

TABLE

| | 5-Lipoxygenase-inhibiting activities | | |
|---|---|---|---|
| Examples No. | 50% Inhibitory concentration IC$_{50}$ (mmol) | Examples No. | 50% Inhibitory concentration IC$_{50}$ (mmol) |
| 1 | 5 × 10$^{-7}$ | 68 | 4 × 10$^{-8}$ |
| 2 | 6 × 10$^{-7}$ | 69 | 6 × 10$^{-6}$ |
| 3 | 9 × 10$^{-7}$ | 70 | 6 × 10$^{-7}$ |
| 4 | 2 × 10$^{-6}$ | 71 | 6 × 10$^{-7}$ |
| 5 | 1 × 10$^{-6}$ | 72 | 9 × 10$^{-7}$ |
| 6 | 6 × 10$^{-8}$ | 73 | 7 × 10$^{-7}$ |
| 7 | 5 × 10$^{-7}$ | 74 | 8 × 10$^{-6}$ |
| 8 | 1 × 10$^{-7}$ | 75 | 2 × 10$^{-5}$ |
| 9 | 1 × 10$^{-7}$ | 76 | 2 × 10$^{-5}$ |
| 10 | 3 × 10$^{-8}$ | 77 | 1 × 10$^{-5}$ |
| 11 | 4 × 10$^{-8}$ | 78 | 3 × 10$^{-8}$ |
| 12 | 8 × 10$^{-8}$ | 79 | 4 × 10$^{-8}$ |
| 13 | 6 × 10$^{-7}$ | 80 | 3 × 10$^{-8}$ |
| 14 | 1 × 10$^{-7}$ | 81 | 5 × 10$^{-8}$ |
| 15 | 9 × 10$^{-8}$ | 82 | 2 × 10$^{-8}$ |
| 16 | 6 × 10$^{-8}$ | 83 | 4 × 10$^{-8}$ |
| 17 | 4 × 10$^{-6}$ | 84 | 3 × 10$^{-8}$ |
| 18 | 6 × 10$^{-6}$ | 85 | 3 × 10$^{-8}$ |
| 19 | 2 × 10$^{-7}$ | 86 | 4 × 10$^{-8}$ |
| 20 | 1 × 10$^{-6}$ | 87 | 6 × 10$^{-8}$ |
| 21 | 3 × 10$^{-8}$ | 88 | 4 × 10$^{-6}$ |
| 22 | 4 × 10$^{-8}$ | 89 | 6 × 10$^{-8}$ |
| 23 | 2 × 10$^{-8}$ | 90 | 6 × 10$^{-8}$ |
| 24 | 1 × 10$^{-7}$ | 91 | 6 × 10$^{-8}$ |

TABLE-continued

5-Lipoxygenase-inhibiting activities

| Examples No. | 50% Inhibitory concentration IC$_{50}$ (mmol) | Examples No. | 50% Inhibitory concentration IC$_{50}$ (mmol) |
|---|---|---|---|
| 25 | $8 \times 10^{-8}$ | 92 | $9 \times 10^{-8}$ |
| 26 | $4 \times 10^{-8}$ | 93 | $3 \times 10^{-6}$ |
| 27 | $7 \times 10^{-9}$ | 94 | $4 \times 10^{-6}$ |
| 28 | $1 \times 10^{-8}$ | 95 | $9 \times 10^{-6}$ |
| 29 | $2 \times 10^{-5}$* | 96 | $2 \times 10^{-8}$ |
| 30 | $2 \times 10^{-6}$* | 97 | $4 \times 10^{-8}$ |
| 31 | $3 \times 10^{-6}$* | 98 | $9 \times 10^{-9}$ |
| 32 | $8 \times 10^{-6}$* | 99 | $3 \times 10^{-8}$ |
| 33 | $4 \times 10^{-6}$* | 100 | $1 \times 10^{-8}$ |
| 34 | $3 \times 10^{-7}$ | 101 | $1 \times 10^{-8}$ |
| 35 | $2 \times 10^{-5}$ | 102 | $2 \times 10^{-7}$ |
| 36 | $2 \times 10^{-4}$ | 103 | $3 \times 10^{-5}$ |
| 37 | $3 \times 10^{-8}$ | 104 | $1 \times 10^{-5}$ |
| 38 | $2 \times 10^{-7}$ | 105 | $1 \times 10^{-8}$ |
| 39 | $1 \times 10^{-7}$ | 106 | $1 \times 10^{-8}$ |
| 40 | $1 \times 10^{-5}$ | 107 | $1 \times 10^{-8}$ |
| 41 | $2 \times 10^{-7}$ | 108 | $8 \times 10^{-9}$ |
| 42 | $2 \times 10^{-6}$ | 109 | $2 \times 10^{-6}$ |
| 43 | $3 \times 10^{-7}$ | 110 | $1 \times 10^{-8}$ |
| 44 | $8 \times 10^{-8}$ | 111 | $1 \times 10^{-8}$ |
| 45 | $6 \times 10^{-8}$ | 112 | $2 \times 10^{-6}$ |
| 46 | $8 \times 10^{-8}$ | 113 | $2 \times 10^{-8}$ |
| 47 | $4 \times 10^{-6}$ | 114 | $2 \times 10^{-6}$ |
| 48 | $6 \times 10^{-8}$ | 115 | $2 \times 10^{-5}$ |
| 49 | $4 \times 10^{-8}$ | 116 | $4 \times 10^{-7}$ |
| 50 | $6 \times 10^{-6}$ | 117 | $2 \times 10^{-8}$ |
| 51 | $1 \times 10^{-6}$ | 118 | $3 \times 10^{-8}$ |
| 52 | $1 \times 10^{-5}$ | 119 | $9 \times 10^{-9}$ |
| 53 | $2 \times 10^{-8}$ | 120 | $1 \times 10^{-8}$ |
| 54 | $2 \times 10^{-8}$ | 121 | $5 \times 10^{-6}$ |
| 55 | $3 \times 10^{-8}$ | 122 | $1 \times 10^{-8}$ |
| 56 | $1 \times 10^{-6}$ | 123 | $1 \times 10^{-5}$ |
| 57 | $4 \times 10^{-7}$ | 124 | $2 \times 10^{-7}$ |
| 58 | $3 \times 10^{-6}$ | 125 | $7 \times 10^{-6}$ |
| 59 | $2 \times 10^{-6}$ | 126 | $1 \times 10^{-8}$ |
| 60 | $1 \times 10^{-4}$ | 127 | $3 \times 10^{-5}$ |
| 61 | $3 \times 10^{-6}$ | 128 | $1 \times 10^{-6}$ |
| 62 | $2 \times 10^{-6}$ | 129 | $2 \times 10^{-8}$ |
| 63 | $5 \times 10^{-8}$ | 130 | $1 \times 10^{-6}$ |
| 64 | $3 \times 10^{-8}$ | 131 | $7 \times 10^{-9}$ |
| 65 | $2 \times 10^{-6}$ | 132 | $1 \times 10^{-6}$ |
| 66 | $3 \times 10^{-8}$ | 133 | $2 \times 10^{-8}$ |
| 67 | $3 \times 10^{-8}$ | 134 | $2 \times 10^{-5}$ |

*In Examples Nos. 29-33, the data show 30% inhibitory concentration, IC$_{30}$ (mole).

What is claimed is:

1. An amide derivative having the formula

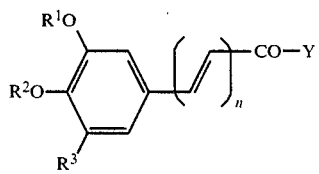

wherein

R$^1$ represents hydrogen or lower alkyl,

R$^2$ represents hydrogen, lower alkyl or toluoyloxy, or R$^1$ and R$^2$ taken together represent a lower alkylene group, R$^3$ represents hydrogen or lower alkoxy,, R$^2$ and R$^3$ both being hydrogen when R$^1$ is hydrogen, n is an integer of 1 or 2, and Y represents

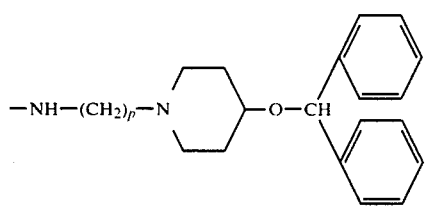

wherein p is an integer from 2 to 4.

2. The amide derivative of claim 1 wherein R$^1$ is lower alkyl, R$^2$ is hydrogen, R$^3$ is hydrogen, n is 2 and p is 2.

3. The amide derivative of claim 1 selected from the group consisting of

1-[2-[3-(3-methoxy-4-hydroxyphenyl)-2-propenoyl] aminoethyl]-4-benzhydryloxypiperidine, 1-[2-[3-(3,5-dimethoxy-4-hydroxyphenyl)-2-propenoyl] aminoethyl]-4-benzhydryloxypiperidine, 1-[2-[5-(3,4-dihydroxyphenyl)-2,4-pentadienoyl] aminoethyl]-4-benzhydryloxypiperidine, 1-[2-[5-(3-methoxy-4-hydroxyphenyl)-2,4-pentadienoyl] aminoethyl]-4-benzhydryloxypiperidine, 1-[2-[5-(3,5-dimethoxy-4-hydroxyphenyl)-2,4-pentadienoyl]aminoethyl]-4-benzhydryloxypiperidine, 1-[3-[3-(3,4-dihydroxyphenyl)-2-propenoyl]-aminopropyl]-4-benzhydryloxypiperidine, 1-[4-[3-(3-methoxy-4-hydroxyphenyl)-2-propenoyl] aminobutyl]-4-benzhydryloxypiperidine, 1-[3-[3-(3,5-dimethoxy-4-hydroxyphenyl)-2-propenoyl] aminopropyl]-4-benzhydryloxypiperidine, 1-[4-[5-(3,4-dihydroxyphenyl)-2,4-pentadienoyl] aminobutyl]-4-benzhydryloxypiperidine, 1-[3-[5-(3-methoxy-4-hydroxyphenyl)-2,4-pentadienoyl ] aminopropyl]-4-benzhydryloxypiperidine and 1-[4-[5-(3,5-dimethoxy-4-hydroxyphenyl)-2,4-pentadienoyl]aminobutyl]-4-benzhydryloxypiperidine.

4. A pharmaceutical composition for inhibiting 5-lipoxygenase activity comprising an effective amount of the amide derivative of claim 1 in a pharmaceutically acceptable carrier or diluent.

5. A method for inhibiting 5-lipoxygenase activity in a mammal comprising administering to said mammal an effective amount of the amide derivative of claim 1.

6. The method of claim 5 wherein said amide derivative is adminstered to said mammal at a dosage rate ranging from 30 to 200 mg/day.

7. The method of claim 5 wherein said amide derivative is administered to said mammal at a dosage rate of 50 to 600 mg/day.

8. A pharmaceutical composition for the treatment of allergic asthma comprising an effective amount of the amide derivative of claim 1 in a pharmaceutically acceptable carrier or diluent.

9. A method for treating allergic asthma in a mammal comprising administering to said mammal an effective amount of the amide derivative of claim 1.

* * * * *